(12) United States Patent
Wichelecki

(10) Patent No.: US 12,215,371 B2
(45) Date of Patent: *Feb. 4, 2025

(54) ENZYMATIC PRODUCTION OF HEXOSES

(71) Applicant: BONUMOSE, INC., Charlottesville, VA (US)

(72) Inventor: Daniel Joseph Wichelecki, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 823 days.

This patent is subject to a terminal disclaimer.

(21) Appl. No.: 17/287,240

(22) PCT Filed: Oct. 29, 2019

(86) PCT No.: PCT/US2019/058483
§ 371 (c)(1),
(2) Date: Apr. 21, 2021

(87) PCT Pub. No.: WO2020/092315
PCT Pub. Date: May 7, 2020

(65) Prior Publication Data
US 2021/0381014 A1     Dec. 9, 2021

Related U.S. Application Data

(60) Provisional application No. 62/857,543, filed on Jun. 5, 2019, provisional application No. 62/752,061, filed on Oct. 29, 2018.

(51) Int. Cl.
*C12P 19/02* (2006.01)
*C12N 9/10* (2006.01)
*C12N 9/90* (2006.01)

(52) U.S. Cl.
CPC ............ *C12P 19/02* (2013.01); *C12N 9/1051* (2013.01); *C12N 9/90* (2013.01); *C12Y 204/01001* (2013.01); *C12Y 204/01007* (2013.01); *C12Y 204/01025* (2013.01); *C12Y 504/02002* (2013.01)

(58) Field of Classification Search
CPC ......... C12P 19/02; C12N 9/1051; C12N 9/90; C12N 9/92; C12N 9/00; C12Y 204/01001; C12Y 204/01007; C12Y 204/01025; C12Y 504/02002
See application file for complete search history.

(56) References Cited

U.S. PATENT DOCUMENTS

| | | | |
|---|---|---|---|
| 2013/0029384 A1* | 1/2013 | Cerdobbel | C12N 11/089 435/174 |
| 2018/0057844 A1 | 3/2018 | Zhang et al. | |
| 2018/0142276 A1 | 5/2018 | Desmet et al. | |
| 2018/0216146 A1 | 8/2018 | Wichelecki | |
| 2020/0347424 A1 | 11/2020 | Koch et al. | |

FOREIGN PATENT DOCUMENTS

| | | | | |
|---|---|---|---|---|
| KR | 20050051055 A | * | 6/2005 | ............. C12N 15/70 |
| RU | 2017111853 A | | 10/2018 | |
| WO | 2016037720 A1 | | 3/2016 | |
| WO | WO-2017059278 A1 | * | 4/2017 | ............... C12N 9/16 |
| WO | 2017153420 A1 | | 9/2017 | |
| WO | 2018/112139 A1 | | 6/2018 | |
| WO | WO-2018129275 A1 | * | 7/2018 | ............. C12N 15/52 |
| WO | 2018/169957 A1 | | 9/2018 | |

OTHER PUBLICATIONS

Translation of Description from KR20050051055A; originally published 2005; translation generated using EPO Patent Translate. Translation downloaded Jan. 10, 2024. (48 pages total) (Year: 2005).*
Zhou, Wei, et al. "One-pot biosynthesis of high-concentration a-glucose 1-phosphate from starch by sequential addition of three hyperthermophilic enzymes." Journal of agricultural and food chemistry 64.8 (2016): 1777-1783. (Year: 2016).*
Pergolizzi, Giulia, et al. "Glycan Phosphorylases in Multi-Enzyme Synthetic Processes." Protein and Peptide Letters 24.8 (2017): 696. (Year: 2017).*
International Search Report and Written Opinion in International Application No. PCT/US2019/058483, dated Feb. 10, 2020.
Russian Office Action dated Mar. 21, 2023 issued in RU Application No. 2021115272.
Uniprot A0A0P6YKY9, Jan. 20, 2016. Accessed at: https://www.uniprot.org/uniprotkb/A0A0P6YKY9/entry.
Uniprot A0A023CRS6, Jun. 11, 2014. Accessed at: https://www.uniprot.org/uniprotkb/A0A023CRS6/entry.
Uniprot A0A023DI95, Jun. 11, 2014. Accessed at: https://www.uniprot.org/uniprotkb/A0A023DI95/entry.
Uniprot A0A150LLZ1, Jun. 8, 2016. Accessed at: https://www.uniprot.org/uniprotkb/A0A150LLZ1/entry.
Uniprot B0K7V8, Mar. 18, 2008. Accessed at: https://www.uniprot.org/uniprotkb/B0K7V8/entry.
Uniprot D1B926, Jan. 19, 2010. Accessed at: https://www.uniprot.org/uniprotkb/D1B926/entry.
Uniprot D7BF07, Aug. 10, 2010. Accessed at: https://www.uniprot.org/uniprotkb/D7BF07/entry.
Uniprot E4U8S9, Feb. 8, 2011. Accessed at:https://www.uniprot.org/uniprotkb/E4U8S9/entry.
Uniprot E8MXP8, Apr. 5, 2011. Accessed at: https://www.uniprot.org/uniprotkb/E8MXP8/entry.

(Continued)

*Primary Examiner* — Aaron J Kosar
*Assistant Examiner* — Andrew T Moehlman
(74) *Attorney, Agent, or Firm* — RAPHAEL BELLUM PLLC

(57) ABSTRACT

Disclosed herein are methods of producing hexoses from saccharides by improved enzymatic processes. The improved processes utilize enzymes with higher activities than those previously reported to convert starch or a starch derivative, cellulose or a cellulose derivative, or sucrose to a glucose 6-phosphate (G6P) intermediate.

19 Claims, 20 Drawing Sheets
Specification includes a Sequence Listing.

(56) References Cited

OTHER PUBLICATIONS

Uniprot E8N4Y6, Apr. 5, 2011. Accessed at: https://www.uniprot.org/uniprotkb/E8N4Y6/entry.
Uniprot G8NCC0, Feb. 22, 2012. Accessed at: https://www.uniprot.org/uniprotkb/G8NCC0/entry.
Uniprot Q5SJ42, Dec. 21, 2004. Accessed at: https://www.uniprot.org/uniprotkb/Q5SJ42/entry.
Uniprot R7RR04, U.S. Appl. No. 07/242,013. Accessed at: https://www.uniprot.org/uniprotkb/R7RR04/entry.
NCBI Database Accession WP_054521641.1, "phosphoglucomutase/phosphomannomutase family protein [Thermanaerothrix daxensis]", dated May 20, 2018.
NCBI Database Accession WP_043903625.1, "phospho-sugar mutase [*Parageobacillus genomo*sp. 1]," dated Jul. 4, 2017.

\* cited by examiner

Glucose 6-phosphate

↕ (PGI)

Fructose 6-phosphate

↕ (F6PE)

Tagatose 6-phosphate

↕ (S6PE)

Sorbose 6-phosphate

↕ (I6PI)

Idose 6-phosphate

↓ (I6PP)

Idose + P$_i$

FIG. 12

SEQUENCE LISTING

<160> NUMBER OF SEQ ID NOS: 26

<210> SEQ ID NO 1
<211> LENGTH: 456
<212> TYPE: PRT
<213> ORGANISM: Thermococcus kodakaraensis

<400> SEQUENCE: 1

Met Gly Lys Leu Phe Gly Thr Phe Gly Val Arg Gly Ile Ala Asn Glu
1               5                   10                  15

Glu Ile Thr Pro Glu Phe Ala Leu Lys Ile Gly Met Ala Phe Gly Thr
            20                  25                  30

Leu Leu Lys Arg Glu Gly Arg Glu Arg Pro Leu Val Val Gly Arg
        35                  40                  45

Asp Thr Arg Val Ser Gly Glu Met Leu Lys Asp Ala Leu Ile Ser Gly
    50                  55                  60

Leu Leu Ser Thr Gly Cys Asp Val Ile Asp Val Gly Ile Ala Pro Thr
65                  70                  75                  80

Pro Ala Ile Gln Trp Ala Thr Asn His Phe Asn Ala Asp Gly Gly Ala
                85                  90                  95

Val Ile Thr Ala Ser His Asn Pro Pro Glu Tyr Asn Gly Ile Lys Leu
            100                 105                 110

Leu Glu Pro Asn Gly Met Gly Leu Lys Lys Glu Arg Glu Ala Ile Val
            115                 120                 125

Glu Glu Leu Phe Phe Ser Glu Asp Phe His Arg Ala Lys Trp Asn Glu
    130                 135                 140

Ile Gly Glu Leu Arg Lys Glu Asp Ile Ile Lys Pro Tyr Ile Glu Ala
145                 150                 155                 160

Ile Lys Asn Arg Val Asp Val Glu Ala Ile Lys Lys Arg Arg Pro Phe
                165                 170                 175

Val Val Val Asp Thr Ser Asn Gly Ala Gly Ser Leu Thr Leu Pro Tyr
            180                 185                 190

Leu Leu Arg Glu Leu Gly Cys Lys Val Val Ser Val Asn Ala His Pro
        195                 200                 205

Asp Gly His Phe Pro Ala Arg Asn Pro Glu Pro Asn Glu Glu Asn Leu
    210                 215                 220

Lys Gly Phe Met Glu Ile Val Lys Ala Leu Gly Ala Asp Phe Gly Val
225                 230                 235                 240

Ala Gln Asp Gly Asp Ala Asp Arg Ala Val Phe Ile Asp Glu Asn Gly
                245                 250                 255

Arg Phe Ile Gln Gly Asp Lys Thr Phe Ala Leu Val Ala Asp Ala Val
            260                 265                 270

Leu Arg Glu Asn Gly Gly Leu Leu Val Thr Thr Ile Ala Thr Ser
        275                 280                 285

Asn Leu Leu Asp Asp Ile Ala Lys Arg Asn Gly Ala Lys Val Met Arg
    290                 295                 300

Thr Lys Val Gly Asp Leu Ile Val Ala Arg Ala Leu Leu Glu Asn Asn
305                 310                 315                 320

Gly Thr Ile Gly Gly Glu Glu Asn Gly Val Ile Phe Pro Asp Phe
                325                 330                 335

Val Leu Gly Arg Asp Gly Ala Met Thr Thr Ala Lys Ile Val Glu Ile
            340                 345                 350

Phe Ala Lys Ser Gly Lys Lys Phe Ser Glu Leu Ile Asp Glu Leu Pro
        355                 360                 365

```
Lys Tyr Tyr Gln Phe Lys Thr Lys Arg His Val Glu Gly Asp Arg Lys
    370                 375                 380
Ala Ile Val Ala Lys Val Ala Glu Leu Ala Glu Lys Lys Gly Tyr Lys
385                 390                 395                 400
Ile Asp Thr Thr Asp Gly Thr Lys Ile Ile Phe Asp Asp Gly Trp Val
                405                 410                 415
Leu Val Arg Ala Ser Gly Thr Glu Pro Ile Ile Arg Ile Phe Ser Glu
                420                 425                 430
Ala Lys Ser Glu Glu Lys Ala Arg Glu Tyr Leu Glu Leu Gly Ile Lys
            435                 440                 445
Leu Leu Glu Glu Ala Leu Lys Gly
    450                 455

<210> SEQ ID NO 2
<211> LENGTH: 582
<212> TYPE: PRT
<213> ORGANISM: Geobacillus stearothermophilus NUB3621

<400> SEQUENCE: 2

Met Asp Trp Lys Ser Lys Tyr Glu Gln Trp Leu Ala Tyr Lys Pro Leu
1               5                   10                  15
Asp Glu Glu Leu Lys Gln Leu Leu Gln Lys Arg Gln Asp Asp Trp Lys
                20                  25                  30
Trp Leu Glu Asp Gly Phe Tyr Lys Asn Leu Glu Phe Gly Thr Gly Gly
            35                  40                  45
Met Arg Gly Glu Ile Gly Pro Gly Thr Asn Arg Met Asn Ile Tyr Thr
        50                  55                  60
Val Arg Lys Ala Ser Glu Gly Leu Ala Arg Tyr Ile Gly Ser Phe Gly
65                  70                  75                  80
Glu Glu Ala Lys Lys Arg Gly Val Val Ile Ala Tyr Asp Ser Arg His
                85                  90                  95
Lys Ser Arg Glu Phe Ala Met Glu Ala Ala Lys Thr Leu Ala Thr His
                100                 105                 110
Gly Ile Gln Thr Tyr Val Phe Asp Glu Leu Arg Pro Thr Pro Glu Leu
            115                 120                 125
Ser Phe Ala Val Arg Tyr Leu His Ala Phe Ser Gly Ile Val Ile Thr
    130                 135                 140
Ala Ser His Asn Pro Pro Glu Tyr Asn Gly Tyr Lys Val Tyr Gly Glu
145                 150                 155                 160
Asp Gly Gly Gln Leu Pro Pro Glu Thr Ala Asp Ala Val Ile Arg Tyr
                165                 170                 175
Val Asn Glu Val Glu Asn Glu Leu Asp Ile His Val Glu Asp Glu Ala
                180                 185                 190
Ile Leu Lys Glu Lys Gly Leu Ile Gln Ile Ile Gly Glu Glu Val Asp
            195                 200                 205
Asn Ala Tyr Ile Glu Ala Val Lys Thr Val Ser Leu Gln Pro Lys Leu
        210                 215                 220
Ala Glu Glu Val Asp Ile Asn Ile Val Phe Thr Pro Leu His Gly Thr
225                 230                 235                 240
Ser Asn Lys Pro Val Arg Arg Ala Leu Lys Glu Leu Gly Tyr Arg Asn
                245                 250                 255
Val Phe Val Val Lys Glu Gln Glu Gln Pro Asp Pro Asn Phe Ser Thr
                260                 265                 270
Val Ala Ser Pro Asn Pro Glu Glu His Ala Ala Phe Ala Leu Ala Ile
            275                 280                 285
```

```
Glu Leu Gly Lys Gln Val Asn Ala Asp Leu Ile Ala Thr Asp Pro
    290                 295                 300
Asp Ala Asp Arg Leu Gly Ile Ala Val Lys Asn Glu Gln Gly Glu Tyr
305                 310                 315                 320
Ile Val Leu Thr Gly Asn Gln Thr Gly Gly Leu Leu Tyr Tyr Leu
                    325                 330                 335
Leu Ser Gln Lys Lys Glu Lys Gly Ile Leu Pro Glu Asn Gly Val Val
                    340                 345                 350
Leu Lys Thr Ile Val Thr Ser Glu Phe Gly Arg Val Ile Ala Gln Ser
                    355                 360                 365
Phe Gly Leu Asp Thr Val Asp Thr Leu Thr Gly Phe Lys Phe Ile Gly
370                 375                 380
Glu Lys Ile Lys Glu Tyr Glu Gln Thr Gly Gln Tyr Thr Phe Gln Phe
385                 390                 395                 400
Gly Tyr Glu Glu Ser Tyr Gly Tyr Leu Ile Gly Asp Phe Ala Arg Asp
                    405                 410                 415
Lys Asp Ala Val Gln Ala Ala Val Leu Ala Ala Glu Val Cys Ala Phe
                    420                 425                 430
Tyr Lys Lys Gln Gly Met Ser Leu Tyr Glu Gly Leu Ile Gln Leu Phe
                    435                 440                 445
Asp Gln Tyr Gly Tyr Arg Glu Gly Gln Gln Ser Leu Thr Leu Lys
450                 455                 460
Gly Lys Glu Gly Ala Glu Thr Ile Gln Ala Ile Leu Thr Ser Phe Arg
465                 470                 475                 480
Asn Glu Pro Pro Thr Glu Val Ala Gly Lys Lys Val Thr Val Ile Glu
                    485                 490                 495
Asp Tyr Lys Thr Lys Glu Arg Ile His Thr Leu Thr Gly Glu Lys Thr
                    500                 505                 510
Val Ile Thr Leu Pro Thr Ser Asn Val Leu Lys Tyr Val Leu Glu Asp
                    515                 520                 525
Asp Ser Trp Phe Cys Leu Arg Pro Ser Gly Thr Glu Pro Lys Ile Lys
530                 535                 540
Val Tyr Phe Gly Val Lys Gly Gln Ser Leu Ala Asp Ser Glu Ala Lys
545                 550                 555                 560
Leu Gln Gln Leu Ser Asp Ala Val Met Lys Arg Val His Asp Phe Leu
                    565                 570                 575
Arg Thr Ala Ser Leu Ser
            580

<210> SEQ ID NO 3
<211> LENGTH: 581
<212> TYPE: PRT
<213> ORGANISM: Caldibacillus debilis

<400> SEQUENCE: 3

Met Glu Trp Lys Gln Arg Ala Glu Arg Trp Leu Arg Phe Glu Asn Leu
1                   5                   10                  15
Asp Pro Glu Leu Lys Lys Gln Leu Glu Glu Met Ala Lys Asp Glu Lys
                    20                  25                  30
Lys Leu Glu Asp Leu Phe Tyr Lys Tyr Leu Glu Phe Gly Thr Gly Gly
                    35                  40                  45
Met Arg Gly Glu Ile Gly Pro Gly Thr Asn Arg Ile Asn Ile Tyr Thr
            50                  55                  60
Val Arg Lys Ala Ser Glu Gly Leu Ala Arg Phe Leu Leu Ala Ser Gly
```

-continued

```
                65                  70                  75                  80
Gly Glu Glu Lys Ala Lys Gln Gly Val Val Ile Ala Tyr Asp Ser Arg
                    85                  90                  95

Arg Lys Ser Arg Glu Phe Ala Leu Glu Thr Ala Lys Thr Val Gly Lys
                    100                 105                 110

His Gly Ile Lys Ala Tyr Val Phe Glu Ser Leu Arg Pro Thr Pro Glu
                    115                 120                 125

Leu Ser Phe Ala Val Arg Tyr Leu His Ala Ala Gly Val Val Ile
            130                 135                 140

Thr Ala Ser His Asn Pro Pro Glu Tyr Asn Gly Tyr Lys Val Tyr Gly
145                 150                 155                 160

Glu Asp Gly Gly Gln Leu Thr Pro Lys Ala Ala Asp Glu Leu Ile Arg
                    165                 170                 175

Tyr Val Tyr Glu Val Glu Asp Glu Leu Ser Leu Thr Val Pro Gly Glu
                    180                 185                 190

Gln Glu Leu Ile Asp Arg Gly Leu Leu Gln Tyr Ile Gly Glu Asn Ile
                    195                 200                 205

Asp Leu Ala Tyr Ile Glu Lys Leu Lys Thr Ile Gln Leu Asn Arg Asp
210                 215                 220

Val Ile Leu Asn Gly Gly Lys Asp Leu Lys Ile Val Phe Thr Pro Leu
225                 230                 235                 240

His Gly Thr Ala Gly Gln Leu Val Gln Thr Gly Leu Arg Glu Phe Gly
                    245                 250                 255

Phe Gln Asn Val Tyr Val Val Lys Glu Gln Glu Gln Pro Asp Pro Asp
                    260                 265                 270

Phe Ser Thr Val Lys Ser Pro Asn Pro Glu Glu His Glu Ala Phe Glu
            275                 280                 285

Ile Ala Ile Arg Tyr Gly Lys Lys Tyr Asp Ala Asp Leu Ile Met Gly
            290                 295                 300

Thr Asp Pro Asp Ser Asp Arg Leu Gly Ile Val Val Lys Asn Gly Gln
305                 310                 315                 320

Gly Asp Tyr Val Val Leu Thr Gly Asn Gln Thr Gly Ala Ile Leu Leu
                    325                 330                 335

Tyr Tyr Leu Leu Ser Gln Lys Lys Glu Lys Gly Met Leu Val Arg Asn
                    340                 345                 350

Ser Ala Val Leu Lys Thr Ile Val Thr Ser Glu Leu Gly Arg Ala Ile
            355                 360                 365

Ala Ser Asp Phe Gly Val Glu Thr Ile Asp Thr Leu Thr Gly Phe Lys
370                 375                 380

Phe Ile Gly Glu Lys Ile Lys Glu Phe Lys Glu Thr Gly Ser His Val
385                 390                 395                 400

Phe Gln Phe Gly Tyr Glu Glu Ser Tyr Gly Tyr Leu Ile Gly Asp Phe
                    405                 410                 415

Val Arg Asp Lys Asp Ala Ile Gln Ala Ala Leu Phe Ala Ala Glu Ala
                    420                 425                 430

Ala Ala Tyr Tyr Lys Ala Gln Gly Lys Ser Leu Tyr Asp Val Leu Met
            435                 440                 445

Glu Ile Tyr Lys Lys Tyr Gly Phe Tyr Lys Glu Ser Leu Arg Ser Ile
            450                 455                 460

Thr Leu Lys Gly Lys Asp Gly Ala Glu Lys Ile Arg Ala Ile Met Asp
465                 470                 475                 480

Ala Phe Arg Gln Asn Pro Pro Glu Glu Val Ser Gly Ile Pro Val Ala
                    485                 490                 495
```

```
Ile Thr Glu Asp Tyr Leu Thr Gln Lys Arg Val Asp Lys Ala Ala Gly
                500                 505                 510

Gln Thr Thr Pro Ile His Leu Pro Lys Ser Asn Val Leu Lys Tyr Tyr
            515                 520                 525

Leu Ala Asp Glu Ser Trp Phe Cys Ile Arg Pro Ser Gly Thr Glu Pro
        530                 535                 540

Lys Cys Lys Phe Tyr Phe Ala Val Arg Gly Asp Ser Glu Ala Gln Ser
545                 550                 555                 560

Glu Ala Arg Leu Arg Gln Leu Glu Thr Asn Val Met Ala Met Val Glu
                565                 570                 575

Lys Ile Leu Gln Lys
            580

<210> SEQ ID NO 4
<211> LENGTH: 584
<212> TYPE: PRT
<213> ORGANISM: Geobacillus thermoglucosidasius

<400> SEQUENCE: 4

Met Asp Trp Lys Lys Lys Tyr Glu Gln Trp Leu Ala Tyr Glu Pro Leu
1               5                   10                  15

Asp Glu Glu Leu Lys His Ser Leu Lys Lys His Gln His Asp Leu Pro
                20                  25                  30

Trp Leu Glu Asp Cys Phe Tyr Lys Asn Leu Glu Phe Gly Thr Gly Gly
            35                  40                  45

Met Arg Gly Glu Ile Gly Pro Gly Thr Asn Arg Met Asn Val Tyr Thr
        50                  55                  60

Ile Arg Lys Ala Ser Glu Gly Leu Ala Arg Tyr Ile Glu Ser Phe Gly
65                  70                  75                  80

Glu Asp Ala Lys Arg Arg Gly Val Val Ile Ala Tyr Asp Ser Arg His
                85                  90                  95

Lys Ser Arg Glu Phe Ala Met Glu Thr Ala Lys Thr Leu Ala Thr His
                100                 105                 110

Gly Ile Gln Thr Tyr Val Phe Asp Glu Leu Arg Pro Thr Pro Glu Leu
            115                 120                 125

Ser Phe Ala Val Arg Tyr Leu Arg Ala Phe Ser Gly Val Val Ile Thr
        130                 135                 140

Ala Ser His Asn Pro Pro Glu Tyr Asn Gly Tyr Lys Val Tyr Gly Glu
145                 150                 155                 160

Asp Gly Gly Gln Leu Pro Pro Glu Thr Ala Asp Ala Val Ile Arg Tyr
                165                 170                 175

Val Asn Glu Val Glu Asn Glu Leu Glu Ile Asp Val Glu Glu Glu Ala
            180                 185                 190

Val Leu Lys Glu Lys Gly Leu Ile Gln Met Ile Gly Glu Glu Val Asp
        195                 200                 205

Asn Ala Tyr Ile Asp Ala Val Lys Thr Ile Ser Phe Gln Pro Lys Leu
    210                 215                 220

Ala Glu Glu Thr Asp Val Asn Ile Val Phe Thr Pro Leu His Gly Thr
225                 230                 235                 240

Ser Asn Lys Pro Ile Arg Arg Ala Leu Thr Glu Leu Gly Tyr Arg His
                245                 250                 255

Val Phe Val Val Glu Glu Gln Glu His Pro Asp Pro Asn Phe Ser Thr
            260                 265                 270

Val Ser Ser Pro Asn Pro Glu Glu His Ala Ala Phe Ala Leu Ala Ile
```

```
                275                 280                 285
Glu Leu Gly Lys Lys Val Asn Ala Asp Leu Leu Ile Ala Thr Asp Pro
        290                 295                 300
Asp Ala Asp Arg Leu Gly Ile Ala Val Lys Asn Asp Lys Gly Asp Tyr
305                 310                 315                 320
Ile Val Leu Thr Gly Asn Gln Thr Gly Gly Leu Leu His Tyr Leu
                325                 330                 335
Leu Ser Gln Lys Lys Glu Lys Gly Ile Leu Pro Glu Asn Gly Val Val
            340                 345                 350
Leu Lys Thr Ile Val Thr Ser Glu Phe Gly Arg Ala Ile Ala Gln Ser
        355                 360                 365
Phe Gly Leu Asp Thr Val Asp Thr Leu Thr Gly Phe Lys Phe Ile Gly
    370                 375                 380
Glu Lys Ile Lys Glu Tyr Glu Gln Thr Gly Gln Tyr Thr Phe Gln Phe
385                 390                 395                 400
Gly Tyr Glu Glu Ser Tyr Gly Tyr Leu Ile Gly Asp Phe Val Arg Asp
                405                 410                 415
Lys Asp Ala Val Gln Ala Ala Val Leu Ala Ala Glu Val Cys Ala Phe
            420                 425                 430
Tyr Lys Lys His Gly Met Ser Leu Tyr Glu Gly Leu Leu Arg Leu Phe
        435                 440                 445
Asp Gln Tyr Gly Tyr Tyr Arg Glu Gly Gln Gln Ser Leu Thr Leu Lys
    450                 455                 460
Gly Lys Lys Gly Ser Glu Thr Ile Gln Ala Ile Leu Thr Ser Phe Arg
465                 470                 475                 480
His Glu Pro Pro Thr Glu Val Ala Gly Lys Lys Val Ile Val Ile Glu
                485                 490                 495
Asp Tyr Lys Thr Lys Glu Arg Val Asn Thr Ala Thr Gly Glu Lys Thr
            500                 505                 510
Leu Ile Ala Leu Pro Thr Ser Asp Val Leu Lys Tyr Val Leu Glu Asp
        515                 520                 525
Asp Ser Trp Phe Cys Leu Arg Pro Ser Gly Thr Glu Pro Lys Leu Lys
    530                 535                 540
Val Tyr Phe Gly Val Lys Gly Glu Ser Leu Ser Asp Ser Glu Ala Lys
545                 550                 555                 560
Leu Gln Gln Leu Ser Asp Thr Val Met Glu Arg Val Arg Gly Phe Leu
                565                 570                 575
Asn Thr Ala Ser Pro Phe Gln Pro
            580

<210> SEQ ID NO 5
<211> LENGTH: 582
<212> TYPE: PRT
<213> ORGANISM: Parageobacillus caldoxylosilyticus NBRC 107762

<400> SEQUENCE: 5

Met Asp Trp Lys Ser Lys Tyr Glu Gln Trp Met Ala Tyr Glu Gln Leu
1               5                   10                  15
Asp Gly Glu Leu Lys Arg Leu Leu Gln Asp Arg Gln Asp Leu Lys
            20                  25                  30
Trp Val Glu Asp Gly Phe Tyr Lys Asn Leu Glu Phe Gly Thr Gly Gly
        35                  40                  45
Met Arg Gly Glu Ile Gly Pro Gly Thr Asn Arg Met Asn Ile Tyr Thr
    50                  55                  60
```

Val Arg Lys Ala Ser Glu Gly Leu Ala Arg Tyr Ile Glu Ser Phe Gly
 65                  70                  75                  80

Glu Glu Ala Lys Lys Arg Gly Val Val Ile Ala Tyr Asp Ser Arg His
                 85                  90                  95

Lys Ser Arg Asp Phe Ala Met Glu Ala Ala Lys Thr Leu Ala Thr His
            100                 105                 110

Gly Ile Gln Thr Tyr Val Phe Asp Glu Leu Arg Pro Thr Pro Glu Leu
        115                 120                 125

Ser Phe Ala Val Arg Tyr Leu Gln Ala Phe Ser Gly Ile Val Ile Thr
    130                 135                 140

Ala Ser His Asn Pro Pro Glu Tyr Asn Gly Tyr Lys Val Tyr Gly Glu
145                 150                 155                 160

Asp Gly Gly Gln Leu Pro Pro Asp Thr Ala Asp Ala Val Ile Arg Tyr
                165                 170                 175

Val Asn Glu Val Ala Asn Glu Leu Asp Ile His Val Glu Asp Glu Ala
            180                 185                 190

Ile Leu Lys Glu Lys Gly Leu Ile Gln Ile Ile Gly Glu Glu Val Asp
        195                 200                 205

Asn Ala Tyr Ile Asp Ala Val Lys Thr Ile Ser Leu Gln Pro Lys Leu
    210                 215                 220

Ala Glu Glu Val Asp Ile Asn Ile Val Phe Thr Pro Leu His Gly Thr
225                 230                 235                 240

Ser Asn Lys Pro Val Arg Arg Ala Leu Lys Glu Leu Gly Tyr Arg Asn
                245                 250                 255

Val Phe Val Val Lys Glu Gln Glu Gln Pro Asp Pro Asn Phe Ser Thr
            260                 265                 270

Val Ala Ser Pro Asn Pro Glu Glu His Ala Ala Phe Ala Leu Ala Ile
        275                 280                 285

Glu Leu Gly Lys Lys Val Asn Ala Asp Leu Leu Ile Ala Thr Asp Pro
    290                 295                 300

Asp Ala Asp Arg Leu Gly Val Ala Val Lys Asn Asp Gln Gly Glu Tyr
305                 310                 315                 320

Val Val Leu Thr Gly Asn Gln Thr Gly Ala Leu Leu Leu His Tyr Leu
                325                 330                 335

Leu Ser Gln Arg Lys Glu Lys Glu Ile Leu Pro Glu Asn Gly Val Val
            340                 345                 350

Leu Lys Thr Ile Val Thr Ser Glu Phe Gly Arg Ala Ile Ala Gln Ser
        355                 360                 365

Phe Gly Leu Glu Thr Val Asp Thr Leu Thr Gly Phe Lys Phe Ile Gly
    370                 375                 380

Glu Lys Ile Lys Glu Tyr Glu Gln Thr Gly Gln Tyr Thr Phe Gln Phe
385                 390                 395                 400

Gly Tyr Glu Glu Ser Tyr Gly Tyr Leu Ile Gly Asp Phe Val Arg Asp
                405                 410                 415

Lys Asp Ala Val Gln Ala Ala Val Leu Ala Ala Glu Val Cys Ala Phe
            420                 425                 430

Tyr Lys Lys Gln Gly Met Ser Leu Tyr Glu Gly Leu Ile His Leu Phe
        435                 440                 445

Asp Arg Tyr Gly Tyr Arg Glu Gly Gln Gln Ser Leu Thr Leu Lys
    450                 455                 460

Gly Lys Glu Gly Ala Glu Thr Ile Gln Ala Ile Leu Thr Ser Phe Arg
465                 470                 475                 480

Asn Glu Pro Pro Thr Glu Val Asp Gly Lys Arg Val Thr Val Ile Glu

```
                        485                 490                 495
Asp Tyr Lys Thr Lys Glu Arg Ile His Thr Leu Thr Gly Glu Lys Thr
                    500                 505                 510

Val Ile Thr Leu Pro Thr Ser Asn Val Leu Lys Tyr Val Leu Glu Asp
                515                 520                 525

Asp Ser Trp Phe Cys Leu Arg Pro Ser Gly Thr Glu Pro Lys Ile Lys
            530                 535                 540

Val Tyr Phe Gly Val Lys Gly Lys Ser Leu Ala Asp Ser Glu Lys
545                 550                 555                 560

Leu Asn Arg Leu Ser Asn Glu Val Met Lys Arg Val His Asp Leu Leu
                565                 570                 575

Arg Thr Ala Ser Leu Ser
                580

<210> SEQ ID NO 6
<211> LENGTH: 567
<212> TYPE: PRT
<213> ORGANISM: Thermobrachium celere DSM 8682

<400> SEQUENCE: 6

Met Glu Tyr Met Ser Met Tyr Lys Arg Trp Leu Glu Phe Asp Glu Glu
1               5                   10                  15

Thr Arg Arg Glu Leu Glu Gly Leu Asp Glu Lys Glu Ile Met Glu Arg
                20                  25                  30

Phe Tyr Lys Glu Leu Glu Phe Gly Thr Gly Gly Leu Arg Gly Ile Ile
            35                  40                  45

Gly Ala Gly Thr Asn Arg Met Asn Val Tyr Thr Val Arg Lys Ala Thr
50                  55                  60

Gln Gly Leu Ala Asn Phe Ile Leu Lys Gln Asn Ile Glu Asn Pro Ser
65                  70                  75                  80

Val Ala Ile Ala Tyr Asp Ser Arg Lys Tyr Ser Asp Val Phe Ala Lys
                85                  90                  95

Glu Ala Ala Leu Val Leu Asn Ala Ser Gly Ile Lys Thr Tyr Ile Tyr
            100                 105                 110

Asp Glu Leu Lys Pro Thr Pro Met Leu Ser Tyr Ala Val Arg His Met
        115                 120                 125

Lys Ala Thr Ala Gly Ile Val Ile Thr Ala Ser His Asn Pro Lys Glu
130                 135                 140

Tyr Asn Gly Tyr Lys Val Tyr Trp Ser Asp Gly Gln Val Thr Glu
145                 150                 155                 160

Glu Leu Ala Glu Gly Ile Leu Asn Glu Ile Lys Asn Val Asp Tyr Ser
                165                 170                 175

Asp Ile Lys Arg Met Asp Tyr Asp Glu Ala Ile Glu Lys Gly Leu Phe
            180                 185                 190

Asn Phe Met Pro Lys Glu Val Glu Asp Thr Tyr Val Lys Leu Val Lys
        195                 200                 205

Gly Leu Thr Val Asn Lys Glu Leu Val Glu Lys Met Lys Asp Lys Val
        210                 215                 220

Lys Val Ile Tyr Thr Pro Leu His Gly Thr Gly Asn Lys Pro Val Arg
225                 230                 235                 240

Arg Val Leu Glu Glu Leu Gly Tyr Lys Asn Val Tyr Val Lys Glu
                245                 250                 255

Gln Glu Asn Pro Asp Pro Ala Phe Ser Thr Val Lys Tyr Pro Asn Pro
            260                 265                 270
```

```
Glu Glu Ser Glu Val Phe Thr Arg Ala Met Glu Met Ala Arg Glu Leu
            275                 280                 285

Asp Ala Asp Val Ile Ile Gly Thr Asp Pro Asp Cys Asp Arg Val Gly
290                 295                 300

Val Val Val Lys Asn Ser Glu Gly Asn Tyr Val Val Leu Thr Gly Asn
305                 310                 315                 320

Gln Thr Gly Ala Leu Leu Thr His Tyr Met Leu Glu Asn Leu Lys Ala
                325                 330                 335

Thr Asn Thr Ile Pro Lys Asn Pro Val Ile Lys Thr Ile Val Thr
            340                 345                 350

Thr Glu Phe Ala Arg Ala Ile Cys Lys Asp Tyr Gly Val Glu Ile Leu
            355                 360                 365

Asp Val Leu Thr Gly Phe Lys Tyr Ile Gly Glu Lys Ile Lys Glu Phe
370                 375                 380

Glu Ile Asn Gly Asp Met Asn Phe Ile Leu Gly Phe Glu Glu Ser Tyr
385                 390                 395                 400

Gly Tyr Leu Ala Gly Thr Phe Val Arg Asp Lys Asp Ala Val Ile Ala
                405                 410                 415

Ser Met Leu Ile Val Glu Met Val Cys Tyr Tyr Lys Asp Arg Gly Met
            420                 425                 430

Ser Leu Tyr Glu Gly Leu Met Glu Leu Tyr Asn Lys Tyr Gly Phe Tyr
            435                 440                 445

Lys Glu Asp Leu Val Ser Ile Thr Leu Lys Gly Ile Glu Gly Ser Glu
            450                 455                 460

Lys Ile Lys Lys Ile Met Glu Asp Leu Arg Ser Asn Pro Pro Lys Lys
465                 470                 475                 480

Val Ala Asp Leu Ser Val Lys Leu Val Lys Asp Tyr Lys Met Ser Val
                485                 490                 495

Thr Lys Asn Val Val Ser Gly Glu Glu Val Ile Glu Leu Pro Lys
            500                 505                 510

Ser Asn Val Ile Gln Leu Val Leu Glu Asp Gly Ser Val Ile Thr Ala
            515                 520                 525

Arg Pro Ser Gly Thr Glu Pro Lys Ile Lys Phe Tyr Phe Met Thr Lys
530                 535                 540

Gly Glu Thr Leu Glu Lys Ala Glu Glu Asn Ile Lys Arg Phe Lys Glu
545                 550                 555                 560

Glu Ile Leu Lys Met Ala Glu
                565

<210> SEQ ID NO 7
<211> LENGTH: 473
<212> TYPE: PRT
<213> ORGANISM: Anaerolinea thermophila

<400> SEQUENCE: 7

Met Ser His Thr Ile Arg Phe Gly Thr Asp Gly Trp Arg Gly Val Ile
1               5                   10                  15

Ala Glu Asp Tyr Thr Phe Ala Asn Val Arg Cys Ala Thr Gln Gly Tyr
                20                  25                  30

Ala Ser Tyr Met Ile Arg His Gly Lys Ala Gly Ala Thr Phe Val Ile
            35                  40                  45

Gly His Asp Lys Arg Phe His Ser Glu Asn Phe Ala Leu Ala Ala Ala
        50                  55                  60

Glu Val Met Ala Gly Asn Gly Leu Lys Val Leu Leu Thr Asp Gly Ala
65                  70                  75                  80
```

Thr Pro Thr Pro Val Ile Ala Phe Ser Val His His Lys Ala Ala
                85                  90                  95

Gly Ala Ile Asn Ile Thr Ala Ser His Asn Pro Thr Asp Asn Gly
            100                 105                 110

Phe Lys Val Arg Asn Glu Phe Gly Gly Ala Ile Asp Pro Glu Gly Leu
        115                 120                 125

Lys Glu Ile Glu Ser Leu Ile Pro Glu Asp Glu Ser Glu Val Lys Arg
130                 135                 140

Met Pro Ala Ser Glu Ala Glu Ala Lys Gly Leu Ile Gln Arg Phe Asp
145                 150                 155                 160

Pro Ala Pro Ala Tyr Ile Glu His Leu Lys Glu Leu Ile Asp Val Glu
                165                 170                 175

Pro Ile Lys Gln Ala Gly Leu Lys Ile Val Asp Cys Met Trp Gly
                180                 185                 190

Asn Gly Ala Gly Trp Phe Pro Arg Ile Leu Ser Gly Gly Lys Thr Glu
        195                 200                 205

Ile Ile Glu Ile His Asn Glu Arg Asn Pro Ile Phe Pro Glu Met Lys
210                 215                 220

Arg Pro Glu Pro Ile Pro Pro Asn Ile Asn Val Gly Leu Lys Lys Thr
225                 230                 235                 240

Val Asp Ser Gly Ala Asp Val Leu Leu Ile Thr Asp Gly Asp Ala Asp
                245                 250                 255

Arg Val Gly Val Gly Asp Glu Lys Gly Asn Phe Ile Asn Gln Leu Gln
                260                 265                 270

Val Tyr Ala Leu Leu Ala Leu Tyr Leu Leu Glu Val Arg Gly Glu Arg
                275                 280                 285

Gly Ala Ile Val Lys Thr Leu Ser Thr Thr Ser Met Leu Glu Lys Leu
290                 295                 300

Gly Lys Met Tyr Asn Ile Pro Val Tyr Glu Thr Gly Val Gly Phe Lys
305                 310                 315                 320

Tyr Val Ala Pro Lys Met Leu Glu Thr Asn Ala Met Ile Gly Glu
                325                 330                 335

Glu Ser Gly Gly Tyr Ala Phe Arg Gly Asn Val Pro Glu Arg Asp Gly
            340                 345                 350

Ile Leu Ala Gly Leu Tyr Ile Leu Asp Met Met Val Lys Leu Gln Arg
            355                 360                 365

Lys Pro Ser Glu Leu Ile Asp Leu Leu Phe Ser Lys Val Gly Pro His
        370                 375                 380

Phe Tyr Asp Arg Ile Asp Arg Thr Phe Thr Gly Glu Arg Ser Ala Arg
385                 390                 395                 400

Glu Gln Ala Ile Leu Ala Ala Asn Pro Thr Thr Ile Gly Gly Leu Lys
            405                 410                 415

Val Thr Gly Leu Asn Thr Thr Asp Gly Phe Lys Phe Ser Leu Glu Asp
            420                 425                 430

Gly Gly Trp Leu Leu Ile Arg Phe Ser Gly Thr Glu Pro Ile Met Arg
        435                 440                 445

Val Tyr Cys Glu Thr Thr His Lys Asp Arg Val Pro Tyr Ile Leu Lys
450                 455                 460

Asp Gly Leu Lys Ile Ala Gly Leu Glu
465                 470

<210> SEQ ID NO 8
<211> LENGTH: 473

<212> TYPE: PRT
<213> ORGANISM: Thermanaerothrix daxensis

<400> SEQUENCE: 8

```
Met Gly His Lys Ile Met Phe Gly Thr Asp Gly Trp Arg Gly Val Ile
1               5                   10                  15

Ala Glu Asp Tyr Thr Phe Asp Asn Val Arg Arg Cys Ala Gln Gly Phe
            20                  25                  30

Ala His Tyr Leu Lys Thr Lys Gly Tyr Lys Asp Glu Trp Val Val Val
        35                  40                  45

Gly Tyr Asp Lys Arg Phe His Ser Glu Asn Phe Ala Gln Ala Ala Ala
50                  55                  60

Glu Val Leu Cys Gly Asn Gly Phe Arg Val Tyr Leu Thr Asp Lys Ala
65                  70                  75                  80

Thr Pro Thr Pro Val Ile Ala Tyr Ala Val Glu Arg Lys Ala Ile
                85                  90                  95

Gly Ala Val Asn Ile Thr Ala Ser His Asn Pro Pro Thr Asp Asn Gly
            100                 105                 110

Phe Lys Val Arg Asp Ala Ser Gly Gly Ala Ile Asp Pro Glu Gly Leu
        115                 120                 125

Lys Arg Ile Glu Ser Ala Ile Pro Asp Glu Met Ser Ala Val Lys Arg
130                 135                 140

Met Pro Ala Ser Glu Ala Glu Ala Gln Gly Arg Leu Val Arg Phe Asp
145                 150                 155                 160

Pro Ala Pro Ala Tyr Ile Glu His Leu Lys Ser Leu Ile Asp Leu Gln
                165                 170                 175

Pro Ile Arg Asp Ala Gly Leu Lys Ile Val Asp Ala Met Trp Gly
            180                 185                 190

Asn Gly Ala Gly Trp Phe Pro Arg Leu Leu Ala Gly Lys Thr Glu
        195                 200                 205

Val Tyr Glu Ile His Asn Thr Arg Asn Pro Ile Phe Pro Glu Met Lys
210                 215                 220

Arg Pro Glu Pro Ile Pro Pro Asn Ile Asp Val Gly Leu Arg Thr Thr
225                 230                 235                 240

Val Glu Arg Arg Ala Asp Val Leu Val Val Thr Asp Gly Asp Ala Asp
                245                 250                 255

Arg Val Gly Ile Gly Asp Glu His Gly Arg Phe Val Asn Gln Leu Gln
            260                 265                 270

Val Tyr Gly Leu Leu Ala Phe Tyr Leu Leu Glu Val Arg Gly Glu Arg
        275                 280                 285

Gly Pro Ile Ile Lys Thr Leu Ser Thr Thr Ser Met Leu Glu Lys Leu
290                 295                 300

Gly Glu Ile Tyr Gly Val Pro Val Tyr Glu Thr Gly Val Gly Phe Lys
305                 310                 315                 320

Tyr Val Ala Pro Lys Phe Leu Glu Thr Asn Ala Leu Ile Gly Gly Glu
                325                 330                 335

Glu Ser Gly Gly Tyr Ala Phe Arg Gly Asn Val Pro Glu Arg Asp Gly
            340                 345                 350

Ile Leu Ala Gly Leu Tyr Phe Leu Asp Met Met Val Arg Leu Asn Arg
        355                 360                 365

Lys Pro Ser Gln Leu Leu Glu Leu Leu Phe Ser Lys Val Gly Pro His
370                 375                 380

Tyr Tyr Asp Arg Val Asp Arg Gln Phe Thr Gly Asp Arg Lys Thr Arg
385                 390                 395                 400
```

```
Glu Glu Met Ile Leu Asn Ala Asn Pro His Thr Ile Gly Gly Leu Lys
                405                 410                 415
Val Val Gly Leu Asn Thr Leu Asp Gly Phe Lys Phe Leu Leu Glu Asp
                420                 425                 430
Gly Gly Trp Met Leu Ile Arg Phe Ser Gly Thr Glu Pro Ile Ile Arg
                435                 440                 445
Val Tyr Cys Glu Thr Thr His Pro Asp Arg Val Gln Pro Ile Leu Gln
            450                 455                 460
Asp Gly Leu Arg Ile Ala Gly Leu Ala
465                 470

<210> SEQ ID NO 9
<211> LENGTH: 822
<212> TYPE: PRT
<213> ORGANISM: Thermotoga maritima

<400> SEQUENCE: 9

Met Leu Glu Lys Leu Pro Glu Asn Leu Lys Glu Leu Glu Ser Leu Ala
1               5                   10                  15
Tyr Asn Leu Trp Trp Ser Trp Ser Arg Pro Ala Gln Arg Leu Trp Arg
                20                  25                  30
Met Ile Asp Ser Glu Lys Trp Glu Glu His Arg Asn Pro Val Lys Ile
            35                  40                  45
Leu Arg Glu Val Ser Lys Glu Arg Leu Glu Glu Leu Ser Lys Asp Glu
        50                  55                  60
Asp Phe Ile Ala Leu Tyr Glu Leu Thr Leu Glu Arg Phe Thr Asp Tyr
65                  70                  75                  80
Met Glu Arg Glu Asp Thr Trp Phe Asn Val Asn Tyr Pro Glu Trp Asp
                85                  90                  95
Glu Lys Ile Val Tyr Met Cys Met Glu Tyr Gly Leu Thr Lys Ala Leu
                100                 105                 110
Pro Ile Tyr Ser Gly Gly Leu Gly Ile Leu Ala Gly Asp His Leu Lys
            115                 120                 125
Ser Ala Ser Asp Leu Gly Leu Pro Leu Ile Ala Val Gly Leu Leu Tyr
130                 135                 140
Lys His Gly Tyr Phe Thr Gln Gln Ile Asp Ser Asp Gly Arg Gln Ile
145                 150                 155                 160
Glu Ile Phe Pro Glu Tyr Asp Ile Glu Glu Leu Pro Met Lys Pro Leu
                165                 170                 175
Arg Asp Glu Asp Gly Asn Gln Val Ile Val Glu Val Pro Ile Asp Asn
            180                 185                 190
Asp Thr Val Lys Ala Arg Val Phe Glu Val Gln Val Gly Arg Val Lys
        195                 200                 205
Leu Tyr Leu Leu Asp Thr Asp Phe Glu Glu Asn Glu Asp Arg Phe Arg
210                 215                 220
Lys Ile Cys Asp Tyr Leu Tyr Asn Pro Glu Pro Asp Val Arg Val Ser
225                 230                 235                 240
Gln Glu Ile Leu Leu Gly Ile Gly Gly Met Lys Leu Leu Lys Thr Leu
                245                 250                 255
Lys Ile Lys Pro Gly Val Ile His Leu Asn Glu Gly His Pro Ala Phe
            260                 265                 270
Ser Ser Leu Glu Arg Ile Lys Ser Tyr Met Glu Glu Gly Tyr Ser Phe
        275                 280                 285
Thr Glu Ala Leu Glu Ile Val Arg Gln Thr Thr Val Phe Thr Thr His
```

```
                290                 295                 300
Thr Pro Val Pro Ala Gly His Asp Arg Phe Pro Phe Asp Phe Val Glu
305                 310                 315                 320

Lys Lys Leu Thr Lys Phe Phe Glu Gly Phe Glu Ser Lys Glu Leu Leu
                325                 330                 335

Met Asn Leu Gly Lys Asp Glu Asp Gly Asn Phe Asn Met Thr Tyr Leu
                340                 345                 350

Ala Leu Arg Thr Ser Ser Phe Ile Asn Gly Val Ser Lys Leu His Ala
                355                 360                 365

Asp Val Ser Arg Arg Met Phe Lys Asn Val Trp Lys Gly Val Pro Val
370                 375                 380

Glu Glu Ile Pro Ile Glu Gly Ile Thr Asn Gly Val His Met Gly Thr
385                 390                 395                 400

Trp Ile Asn Arg Glu Met Arg Lys Leu Phe Asp Arg Tyr Leu Gly Arg
                405                 410                 415

Val Trp Arg Glu His Thr Asp Leu Glu Gly Ile Trp Tyr Gly Val Asp
                420                 425                 430

Arg Ile Pro Asp Glu Glu Leu Trp Glu Ala His Leu Asn Ala Lys Lys
                435                 440                 445

Arg Phe Ile Asp Tyr Ile Arg Glu Ser Ile Lys Arg Arg Asn Glu Arg
                450                 455                 460

Leu Gly Ile Asn Glu Pro Leu Pro Glu Ile Ser Glu Asn Val Leu Ile
465                 470                 475                 480

Ile Gly Phe Ala Arg Arg Phe Ala Thr Tyr Lys Arg Ala Val Leu Leu
                485                 490                 495

Phe Ser Asp Leu Glu Arg Leu Lys Arg Ile Val Asn Asn Ser Glu Arg
                500                 505                 510

Pro Val Tyr Ile Val Tyr Ala Gly Lys Ala His Pro Arg Asp Glu Gly
                515                 520                 525

Gly Lys Glu Phe Leu Arg Arg Ile Tyr Glu Val Ser Gln Met Pro Asp
                530                 535                 540

Phe Lys Asn Lys Ile Ile Val Leu Glu Asn Tyr Asp Ile Gly Met Ala
545                 550                 555                 560

Arg Leu Met Val Ser Gly Val Asp Val Trp Leu Asn Asn Pro Arg Arg
                565                 570                 575

Pro Met Glu Ala Ser Gly Thr Ser Gly Met Lys Ala Ala Ala Asn Gly
                580                 585                 590

Val Leu Asn Ala Ser Val Tyr Asp Gly Trp Trp Val Glu Gly Tyr Asn
                595                 600                 605

Gly Arg Asn Gly Trp Val Ile Gly Asp Glu Ser Val Leu Pro Glu Thr
                610                 615                 620

Glu Ala Asp Asp Pro Lys Asp Ala Glu Ala Leu Tyr Glu Leu Leu Glu
625                 630                 635                 640

Asn Glu Ile Ile Pro Thr Tyr Tyr Glu Asn Arg Glu Lys Trp Ile Phe
                645                 650                 655

Met Met Lys Glu Ser Ile Lys Ser Val Ala Pro Lys Phe Ser Thr Thr
                660                 665                 670

Arg Met Leu Lys Glu Tyr Thr Glu Lys Phe Tyr Ile Lys Gly Leu Val
                675                 680                 685

Asn Arg Glu Trp Leu Glu Arg Arg Glu Asn Val Glu Lys Ile Gly Ala
                690                 695                 700

Trp Lys Glu Arg Ile Leu Lys Asn Trp Glu Asn Val Ser Ile Glu Arg
705                 710                 715                 720
```

-continued

```
Ile Val Leu Glu Asp Ser Lys Ser Val Glu Val Thr Val Lys Leu Gly
                725                 730                 735

Asp Leu Thr Pro Asn Asp Val Ile Val Glu Leu Val Ala Gly Arg Gly
            740                 745                 750

Glu Gly Met Glu Asp Leu Glu Val Trp Lys Val Ile His Ile Arg Arg
        755                 760                 765

Tyr Arg Lys Glu Asn Asp Leu Phe Val Tyr Thr Tyr Thr Asn Gly Val
    770                 775                 780

Leu Gly His Leu Gly Ser Pro Gly Trp Phe Tyr Ala Val Arg Val Ile
785                 790                 795                 800

Pro Tyr His Pro Arg Leu Pro Ile Lys Phe Leu Pro Glu Val Pro Val
                805                 810                 815

Val Trp Lys Lys Val Leu
            820

<210> SEQ ID NO 10
<211> LENGTH: 819
<212> TYPE: PRT
<213> ORGANISM: Thermus thermophilus
<220> FEATURE:
<221> NAME/KEY: misc_feature
<222> LOCATION: (745)..(745)
<223> OTHER INFORMATION: Xaa can be any naturally occurring amino acid

<400> SEQUENCE: 10

Met Asn Val Leu Gly Arg Ile Thr Ala Met Pro Asp Leu Pro Glu Pro
1               5                   10                  15

Leu Glu Gly Leu Lys Glu Ile Ala Tyr Asn Leu Trp Trp Ser Trp Asn
            20                  25                  30

Pro Glu Ala Ala Glu Leu Phe Gln Glu Leu Asp Pro Ala Leu Trp Lys
        35                  40                  45

Arg Phe Arg Gly Asn Pro Val Lys Leu Leu Leu Glu Leu Asp Pro Ala
    50                  55                  60

Arg Leu Glu Ala Leu Ser Ala Ser Gly Tyr Ala Ala Arg Val Gln Ala
65                  70                  75                  80

Thr Arg Glu Ala Leu Arg Ala Tyr Leu Glu Ala Arg Thr Lys Arg
                85                  90                  95

Gly Pro Leu Val Ala Tyr Phe Ser Ala Glu Tyr Gly Phe His Ser Ser
            100                 105                 110

Leu Pro Ile Tyr Ala Gly Gly Leu Gly Val Leu Ala Gly Asp His Val
        115                 120                 125

Lys Ala Ala Ser Asp Leu Gly Leu Asn Leu Val Gly Val Gly Leu Phe
    130                 135                 140

Tyr His Glu Gly Tyr Phe His Gln Arg Leu Ser Pro Glu Gly Glu Gln
145                 150                 155                 160

Val Glu Val Tyr Glu Pro Leu Arg Pro Glu Glu Leu Pro Leu Val Pro
                165                 170                 175

Val Gln Asp Ala Glu Gly Arg Pro Val Arg Val Ala Val Glu Phe Pro
            180                 185                 190

Gly Arg Leu Val His Val Gly Gly Tyr Arg Val Gln Val Gly Ala Val
        195                 200                 205

Pro Val Tyr Leu Leu Thr Thr Asp Leu Pro Glu Asn Ala Pro Glu Asp
    210                 215                 220

Arg Gln Ile Thr Ala Arg Leu Tyr Ala Ala Gly Leu Glu Ala Arg Ile
225                 230                 235                 240
```

```
Gln Gln Glu Leu Val Leu Gly Leu Gly Gly Val Arg Phe Leu Arg Ala
            245                 250                 255

Leu Gly Leu Ala Pro Ala Phe Phe His Met Asn Glu Gly His Ser Ala
        260                 265                 270

Phe Leu Gly Leu Glu Arg Leu Arg Glu Leu Val Ala Glu Gly Tyr Pro
    275                 280                 285

Phe Arg Glu Ala Leu Glu Leu Ala Arg Ala Ser Ala Leu Phe Thr Thr
290                 295                 300

His Thr Pro Val Pro Ala Gly His Asp Val Phe Pro Leu Asp Leu Val
305                 310                 315                 320

Asp Arg Tyr Leu Gly Gly Phe Trp Glu Lys Leu Gly Val Asp Arg Asp
                325                 330                 335

Thr Phe Leu Gly Leu Gly Leu Glu Glu Lys Pro Trp Gly Pro Val Phe
            340                 345                 350

Ser Met Ser Asn Leu Ala Leu Arg Thr Ala Ala Gln Ala Asn Gly Val
        355                 360                 365

Ser Arg Leu His Gly Glu Val Ser Arg Asn Met Phe Arg His Leu Trp
    370                 375                 380

Pro Gly Leu Leu Ala Glu Glu Val Pro Ile Gly His Val Thr Asn Gly
385                 390                 395                 400

Val His Thr Trp Thr Phe Leu His Pro Arg Leu Arg Arg His Tyr Ala
                405                 410                 415

Glu Val Phe Gly Pro Glu Trp Val Glu Arg Pro Glu Asp Pro Glu Thr
            420                 425                 430

Trp Arg Val Glu Gly Leu Gly Glu Ala Phe Trp Arg Ile Arg Gln Asp
        435                 440                 445

Leu Lys Leu Phe Leu Val Arg Glu Val Arg Gln Arg Leu Tyr Glu Gln
    450                 455                 460

Arg Arg Arg Asn Gly Glu Gly Pro Ala Arg Leu Arg Glu Ala Glu Lys
465                 470                 475                 480

Ala Leu Asp Pro Glu Ala Leu Thr Ile Gly Phe Ala Arg Arg Phe Ala
                485                 490                 495

Thr Tyr Lys Arg Ala Val Leu Leu Phe Lys Asp Pro Glu Arg Leu Leu
            500                 505                 510

Arg Ile Leu Lys Gly Pro Tyr Pro Val Gln Phe Val Phe Ala Gly Lys
        515                 520                 525

Ala His Pro Lys Asp Glu Ala Gly Lys Ala Tyr Leu Gln Glu Leu Val
    530                 535                 540

Ser Lys Ile Arg Glu Tyr Gly Leu Glu Asp Arg Met Val Val Leu Glu
545                 550                 555                 560

Asp Tyr Asp Met Tyr Leu Ala Arg Val Leu Thr His Gly Ser Asp Val
                565                 570                 575

Trp Leu Asn Thr Pro Arg Arg Pro Met Glu Ala Ser Gly Thr Ser Gly
            580                 585                 590

Met Lys Ala Ala Leu Asn Gly Ala Leu Asn Leu Ser Val Leu Asp Gly
        595                 600                 605

Trp Trp Ala Glu Ala Tyr Asn Gly Lys Asn Gly Phe Ala Ile Gly Asp
    610                 615                 620

Glu Arg Val Tyr Glu Ser Glu Glu Ala Gln Asp Val Ala Asp Ala Gln
625                 630                 635                 640

Ala Leu Tyr Asp Leu Leu Glu Ser Glu Val Ile Pro Leu Phe Tyr Ala
                645                 650                 655

Lys Gly Leu Glu Gly Tyr Ser Ser Gly Trp Met Ser Met Val His Glu
```

```
                    660                 665                 670
Ser Leu Arg Thr Val Gly Pro Tyr Phe Ser Ala Gly Arg Met Val Arg
            675                 680                 685

Asp Tyr Leu Ala Leu Tyr Glu Arg Gly Ala Leu Trp Glu Lys Glu Ala
            690                 695                 700

Arg Ala Arg Leu Glu Ala Leu Lys Ala Phe Ala Glu Ala Leu Pro Ala
705                 710                 715                 720

Phe His Ala Leu Gly Val Arg Pro Glu Val Pro Gly Asp Leu Thr Leu
                    725                 730                 735

Asn Gly Gly Arg Leu Glu Val Gly Xaa Val Leu Glu Gly Glu Val Pro
                740                 745                 750

Glu Gly Leu Arg Pro His Leu Arg Val Gln Leu Val Val Arg Arg Leu
            755                 760                 765

Gly Gly Gly Leu Glu Val Val Asp Leu Glu Glu Val Ala Pro Gly Arg
        770                 775                 780

Tyr Arg Thr Ala Phe Arg Pro Thr Arg Pro Gly Ser Tyr Thr Tyr Gly
785                 790                 795                 800

Leu Arg Leu Ala Leu Leu His Pro Val Thr Gly Arg Val Glu Trp Val
                    805                 810                 815

Arg Trp Ala

<210> SEQ ID NO 11
<211> LENGTH: 809
<212> TYPE: PRT
<213> ORGANISM: Thermus sp. CCB_US3_UF1

<400> SEQUENCE: 11

Met Pro Leu Leu Pro Glu Pro Leu Ser Gly Leu Lys Glu Leu Ala Tyr
1               5                   10                  15

Asn Leu Trp Trp Ser Trp Asn Pro Glu Ala Ala Glu Leu Phe Gln Glu
                20                  25                  30

Ile Asp Pro Ser Leu Trp Lys Arg Phe Arg Gly Asn Pro Val Lys Leu
            35                  40                  45

Leu Leu Glu Ala Asp Pro Gly Arg Leu Glu Gly Leu Ala Ala Thr Ser
        50                  55                  60

Tyr Pro Ala Arg Val Gly Ala Val Val Glu Ala Leu Arg Ala Tyr Leu
65                  70                  75                  80

Arg Glu Arg Glu Glu Lys Gln Gly Pro Leu Val Ala Tyr Phe Ser Ala
                    85                  90                  95

Glu Tyr Gly Phe His Ser Ser Leu Pro Ile Tyr Ser Gly Gly Leu Gly
                100                 105                 110

Val Leu Ala Gly Asp His Val Lys Ala Ala Ser Asp Leu Gly Leu Asn
            115                 120                 125

Leu Val Gly Val Gly Ile Phe Tyr His Glu Gly Tyr Phe His Gln Arg
        130                 135                 140

Leu Ser Pro Glu Gly Val Gln Val Glu Val Tyr Glu Thr Leu His Pro
145                 150                 155                 160

Glu Glu Leu Pro Leu Tyr Pro Val Gln Asp Arg Glu Gly Arg Pro Leu
                165                 170                 175

Arg Val Gly Val Glu Phe Pro Gly Arg Thr Leu Trp Leu Ser Ala Tyr
                180                 185                 190

Arg Val Gln Val Gly Ala Val Pro Val Tyr Leu Leu Thr Ala Asn Leu
            195                 200                 205

Pro Glu Asn Thr Pro Glu Asp Arg Ala Ile Thr Ala Arg Leu Tyr Ala
```

```
                    210                 215                 220
Pro Gly Leu Glu Met Arg Ile Gln Gln Glu Leu Val Leu Gly Leu Gly
225                 230                 235                 240

Gly Val Arg Leu Leu Arg Ala Leu Gly Leu Ala Pro Glu Val Phe His
                245                 250                 255

Met Asn Glu Gly His Ser Ala Phe Leu Gly Leu Glu Arg Val Arg Glu
                260                 265                 270

Leu Val Ala Glu Gly His Pro Phe Pro Val Ala Leu Glu Leu Ala Arg
            275                 280                 285

Ala Gly Ala Leu Phe Thr Thr His Thr Pro Val Pro Ala Gly His Asp
290                 295                 300

Ala Phe Pro Leu Glu Leu Val Glu Arg Tyr Leu Gly Gly Phe Trp Glu
305                 310                 315                 320

Arg Met Gly Thr Asp Arg Glu Thr Phe Leu Ser Leu Gly Leu Glu Glu
                325                 330                 335

Lys Pro Trp Gly Lys Val Phe Ser Met Ser Asn Leu Ala Leu Arg Thr
                340                 345                 350

Ser Ala Gln Ala Asn Gly Val Ser Arg Leu His Gly Glu Val Ser Arg
                355                 360                 365

Glu Met Phe His His Leu Trp Pro Gly Phe Leu Arg Glu Glu Val Pro
370                 375                 380

Ile Gly His Val Thr Asn Gly Val His Thr Trp Thr Phe Leu His Pro
385                 390                 395                 400

Arg Leu Arg Arg His Tyr Ala Glu Val Phe Gly Pro Glu Trp Arg Lys
                405                 410                 415

Arg Pro Glu Asp Pro Glu Thr Trp Lys Val Glu Ala Leu Gly Glu Glu
                420                 425                 430

Phe Trp Gln Ile His Lys Asp Leu Arg Ala Glu Leu Val Arg Glu Val
                435                 440                 445

Arg Thr Arg Leu Tyr Glu Gln Arg Arg Asn Gly Glu Ser Pro Ser
                450                 455                 460

Arg Leu Arg Glu Ala Glu Lys Val Leu Asp Pro Glu Ala Leu Thr Ile
465                 470                 475                 480

Gly Phe Ala Arg Arg Phe Ala Thr Tyr Lys Arg Ala Val Leu Leu Phe
                485                 490                 495

Lys Asp Pro Glu Arg Leu Arg Arg Leu Leu His Gly His Tyr Pro Ile
                500                 505                 510

Gln Phe Val Phe Ala Gly Lys Ala His Pro Lys Asp Glu Pro Gly Lys
                515                 520                 525

Ala Tyr Leu Gln Glu Leu Phe Ala Lys Ile Arg Glu Tyr Gly Leu Glu
                530                 535                 540

Asp Arg Met Val Val Leu Glu Asp Tyr Asp Met Tyr Leu Ala Arg Val
545                 550                 555                 560

Leu Val His Gly Ser Asp Val Trp Leu Asn Thr Pro Arg Arg Pro Met
                565                 570                 575

Glu Ala Ser Gly Thr Ser Gly Met Lys Ala Ala Leu Asn Gly Ala Leu
                580                 585                 590

Asn Leu Ser Val Leu Asp Gly Trp Trp Ala Glu Ala Tyr Asn Gly Lys
                595                 600                 605

Asn Gly Phe Ala Ile Gly Asp Glu Arg Val Tyr Glu Ser Glu Glu Ala
                610                 615                 620

Gln Asp Met Ala Asp Ala Gln Ala Leu Tyr Asp Val Leu Glu Phe Glu
625                 630                 635                 640
```

Val Leu Pro Leu Phe Tyr Ala Lys Gly Pro Glu Gly Tyr Ser Ser Gly
              645                 650                 655

Trp Leu Ser Met Val His Glu Ser Leu Arg Thr Val Gly Pro Arg Tyr
            660                 665                 670

Ser Ala Ala Arg Met Val Gly Asp Tyr Leu Glu Ile Tyr Arg Arg Gly
                675                 680                 685

Gly Ala Trp Ala Glu Ala Arg Ala Gly Gln Glu Ala Leu Ala Ala
        690                 695                 700

Phe His Gln Ala Leu Pro Ala Leu Gln Gly Val Thr Leu Arg Ala Gln
705                 710                 715                 720

Val Pro Gly Asp Leu Thr Leu Asn Gly Val Pro Met Arg Val Arg Ala
                725                 730                 735

Phe Leu Glu Gly Glu Val Pro Glu Ala Leu Arg Pro Phe Leu Glu Val
                740                 745                 750

Gln Leu Val Val Arg Ser Ser Gly His Leu Glu Val Val Pro Met
        755                 760                 765

Arg Pro Gly Pro Asp Gly Tyr Glu Val Ala Tyr Arg Pro Ser Arg Pro
770                 775                 780

Gly Ser Tyr Ala Tyr Gly Val Arg Leu Ala Leu Arg His Pro Ile Thr
785                 790                 795                 800

Gly His Val Ala Trp Val Arg Trp Ala
                805

<210> SEQ ID NO 12
<211> LENGTH: 541
<212> TYPE: PRT
<213> ORGANISM: Thermoanaerobacter pseudethanolicus strain ATCC 33223

<400> SEQUENCE: 12

Met Gly Asn Glu Lys Leu Pro Arg Val Ala Tyr Phe Cys Met Glu Tyr
1               5                   10                  15

Gly Leu Gln Ser Asp Phe Lys Leu Tyr Ala Gly Leu Gly Ile Leu
            20                  25                  30

Ala Gly Asp His Leu Lys Ala Ala Lys Glu Leu Gly Met Pro Leu Val
            35                  40                  45

Gly Ile Gly Ile Leu Trp Lys Gln Gly Tyr Thr Glu Gln His Ile Gly
        50                  55                  60

Glu Asp Gly Tyr Pro Tyr Asp Ala Tyr Arg Asn Tyr Thr Arg Lys Tyr
65                  70                  75                  80

Asp Phe Leu Lys Asp Thr Gly Val Lys Val Lys Val Lys Ile Arg Asn
                85                  90                  95

Arg Asn Val Tyr Cys Lys Val Trp Leu Ile Asp Asn Phe Asp Asn Ala
                100                 105                 110

Pro Leu Tyr Leu Leu Asp Thr Asp Ile Pro Glu Asn Gly Asp Arg Trp
            115                 120                 125

Ile Thr Gly Gln Leu Tyr Gly Trp Phe Gly Glu Arg Val Ala Gln
        130                 135                 140

Glu Ile Val Leu Gly Ile Gly Gly Val Arg Ala Leu Arg Ala Leu Gly
145                 150                 155                 160

Ile Asp Val Asp Val Tyr His Phe Asn Glu Gly His Ala Val Leu Ala
                165                 170                 175

Ala Ile Glu Leu Ile Arg Glu Lys Met Glu Asn Gln Asn Met Ser Phe
            180                 185                 190

Glu Glu Ala Trp Lys Ala Thr Arg Glu Glu Val Val Phe Thr Thr His

```
                195                 200                 205
Thr Pro Val Lys Glu Gly Asn Glu Ser His Asp Leu Glu Leu Leu Met
210                 215                 220

Tyr Met Gly Ala Asn Asn Gly Leu Ser Ile Glu Gln Met Ala Gln Ile
225                 230                 235                 240

Gly Gly Val Pro Phe Asn Met Thr Val Ala Gly Leu Arg Leu Ser Arg
                245                 250                 255

Ile Ala Asn Gly Val Ser Lys Leu His Gly Gln Thr Ala Asn Lys Met
            260                 265                 270

Trp Gln His Val Asp Asn Lys Ala Pro Ile Ile Ser Ile Thr Asn Gly
        275                 280                 285

Ile Asp Arg Asn Thr Trp Val Asp Lys Arg Ile Ile Glu Ala Tyr Asn
290                 295                 300

Lys Gly Glu Gly Leu Leu Glu Thr His Asn Ile Leu Lys Gln Glu Leu
305                 310                 315                 320

Ile Asp Phe Val Tyr Gln Arg Thr Gly Val Lys Leu Asp Ala Asp Lys
                325                 330                 335

Leu Leu Ile Gly Phe Ser Arg Arg Ala Ala Pro Tyr Lys Arg Ser Asp
            340                 345                 350

Leu Ile Phe Thr Asn Asp Glu Val Ile Gly Asp Tyr Leu Arg Ser Lys
        355                 360                 365

Lys Ile Gln Met Val Phe Ser Gly Lys Gly His Pro Leu Asp Asp Val
370                 375                 380

Gly Lys Lys Ile Val Ala Lys Leu Ile Glu Met Thr Lys Lys Tyr Pro
385                 390                 395                 400

Glu Ser Val Val Phe Leu Glu Asp Tyr Asp Met Thr Ile Gly Lys Met
                405                 410                 415

Leu Thr Arg Gly Thr Asp Val Trp Leu Asn Asn Pro Arg Arg Pro Leu
            420                 425                 430

Glu Ala Ser Gly Thr Ser Gly Met Lys Ala Ala Met Asn Gly Val Leu
        435                 440                 445

Asn Leu Ser Ile Leu Asp Gly Trp Trp Ala Glu Ala Cys Ile Asp Gly
450                 455                 460

Val Asn Gly Trp Gln Phe Gly Asp Gly Phe Glu Ser Asp Asn Ile Glu
465                 470                 475                 480

Glu Leu Asp Lys His Asp Leu Glu Ala Leu Tyr Asp Val Leu Leu Asn
                485                 490                 495

Lys Val Val Pro Thr Tyr Tyr Asn Asp Lys Ala Lys Trp Glu Asn Met
            500                 505                 510

Met Arg Glu Ser Ile Arg Thr Thr Tyr Glu Ala Phe Ser Ala Asn Arg
        515                 520                 525

Met Leu Lys Glu Tyr Tyr Asp Leu Met Tyr Thr Lys Lys
530                 535                 540

<210> SEQ ID NO 13
<211> LENGTH: 578
<212> TYPE: PRT
<213> ORGANISM: Thermanaerovibrio acidaminovorans strain ATCC 49978

<400> SEQUENCE: 13

Met Thr Ile Met Thr Tyr Gly Asp Asn Ile Gly Asn Ser Met Leu Lys
1               5                   10                  15

Thr Leu Glu His Asp Pro Val Phe Arg Ser Val Ala Tyr Phe Ser Met
            20                  25                  30
```

Glu Ile Ala Ile Arg Pro Glu Ile Pro Thr Tyr Ser Gly Leu Gly
             35                  40                  45

Val Leu Ala Gly Asp Ile Ile Lys Ser Ala Ala Asp Leu Gly Val Pro
 50                  55                  60

Met Ala Ala Val Thr Leu Leu Tyr Arg Lys Gly Tyr Phe Ile Gln His
 65                  70                  75                  80

Val Asp Gln Glu Gly Tyr Gln Arg Glu Ser Pro Val Glu Trp Lys Pro
                 85                  90                  95

Glu Glu Tyr Leu Thr Leu Leu Pro Asn Glu Ile Ser Val Met Leu Glu
                100                 105                 110

Gly Arg Pro Val Lys Val Arg Ala Trp Val Tyr Asp Tyr Val Gly Gln
            115                 120                 125

Ser Gly Tyr Pro Leu Pro Ile Tyr Phe Leu Asp Thr Asp Phe Glu Ser
    130                 135                 140

Asn Ala Pro Ala Asp Arg Asn Leu Thr Trp His Leu Tyr Gly Gly Asp
145                 150                 155                 160

Gln Arg Tyr Arg Leu Cys Gln Glu Leu Ile Leu Gly Val Gly Gly Leu
                165                 170                 175

Arg Met Leu Arg Asp Leu Gly Tyr Arg Asn Ile Lys Thr Phe His Leu
            180                 185                 190

Asn Glu Gly His Ala Gly Phe Ile Thr Leu Glu Leu Leu Arg Glu Gln
    195                 200                 205

Gly Tyr Glu Asp Tyr Asp Lys Ile Arg Asp Lys Val Ile Phe Thr Thr
210                 215                 220

His Thr Pro Val Pro Ala Gly His Asp His Phe Ser Tyr Glu Leu Ile
225                 230                 235                 240

Asp Lys Val Met Asp Pro Val Phe Val His His Ile Lys Arg Met Met
                245                 250                 255

Gly Pro Glu Gly Val Ser Met Thr Glu Leu Gly Leu Arg Tyr Ser Arg
            260                 265                 270

Tyr Thr Asn Ala Val Ser Ile Lys His Ala Glu Val Ser Arg Asn Met
    275                 280                 285

Phe Asn Ser Ala Asn Ile Asp Ala Val Thr Asn Gly Val His Ser Thr
290                 295                 300

Thr Trp Thr Cys Pro Gly Phe Ala Lys Leu Tyr Asp Arg Tyr Ile Ala
305                 310                 315                 320

Gly Trp Arg Asn Asp Pro Ser Arg Leu Ile Gln Ala Leu Gln Leu Pro
                325                 330                 335

Asp Glu Glu Val Trp Lys Ala His Gln Ala Ala Lys Met Lys Leu Leu
            340                 345                 350

Ala Arg Val Leu Glu Glu Thr Gly Arg Glu Leu Asp Ala Asp Val Leu
    355                 360                 365

Thr Ile Gly Phe Ala Arg Arg Ala Ala Tyr Lys Arg Ala Asp Leu
370                 375                 380

Leu Phe Ser Asp Val Lys Arg Leu Ile Asp Val Cys Ser Gly Gln Val
385                 390                 395                 400

Gln Phe Ile Phe Ala Gly Lys Ala His Pro His Asp Glu Pro Gly Lys
                405                 410                 415

Ala Met Ile Lys Arg Ile His Gln Met Ala Lys Glu Ile Gly Ser Ala
            420                 425                 430

Val Pro Ile Val Phe Leu Glu Asn Tyr Asp Met Ser Leu Ala Ser Leu
    435                 440                 445

Leu Thr Ser Gly Val Asp Leu Trp Leu Asn Asn Pro Arg Arg Pro Arg

```
                   450                 455                 460
Glu Ala Ser Gly Thr Ser Gly Met Lys Cys Thr His Asn Gly Val Met
465                 470                 475                 480

Asn Phe Ser Val Leu Asp Gly Trp Trp Ile Glu Gly Trp Val Glu Asp
                485                 490                 495

Val Thr Gly Trp Ser Ile Gly Pro Asp Pro Glu Ala Glu Leu Val
                500                 505                 510

Glu Tyr Asp Glu Met Gln Asp Ala Met Asp Leu Tyr Asn Lys Leu Glu
                515                 520                 525

Asp Lys Val Ile Pro Thr Tyr Tyr Gln His Arg Glu Lys Trp Ile Trp
                530                 535                 540

Met Met Lys His Ala Ile Ala Leu Asn Ala Ser Tyr Phe Asn Thr His
545                 550                 555                 560

Arg Val Val Lys Glu Tyr Cys Glu Lys Ala Tyr Gly Val Val Phe Arg
                565                 570                 575

Gly Leu

<210> SEQ ID NO 14
<211> LENGTH: 659
<212> TYPE: PRT
<213> ORGANISM: Thermococcus litoralis

<400> SEQUENCE: 14

Met Glu Arg Ile Asn Phe Ile Phe Gly Ile His Asn His Gln Pro Leu
1               5                   10                  15

Gly Asn Phe Gly Trp Val Phe Glu Glu Ala Tyr Asn Arg Ser Tyr Arg
                20                  25                  30

Pro Phe Met Glu Ile Leu Glu Glu Phe Pro Glu Met Lys Val Asn Val
            35                  40                  45

His Phe Ser Gly Pro Leu Leu Glu Trp Ile Glu Glu Asn Lys Pro Asp
        50                  55                  60

Tyr Leu Asp Leu Leu Arg Ser Leu Ile Lys Arg Gly Gln Leu Glu Ile
65                  70                  75                  80

Val Val Ala Gly Phe Tyr Glu Pro Val Leu Ala Ala Ile Pro Lys Glu
                85                  90                  95

Asp Arg Leu Val Gln Ile Glu Met Leu Lys Asp Tyr Ala Arg Lys Leu
            100                 105                 110

Gly Tyr Asp Ala Lys Gly Val Trp Leu Thr Glu Arg Val Trp Gln Pro
        115                 120                 125

Glu Leu Val Lys Ser Leu Arg Glu Ala Gly Ile Glu Tyr Val Val Val
    130                 135                 140

Asp Asp Tyr His Phe Met Ser Ala Gly Leu Ser Lys Glu Glu Leu Phe
145                 150                 155                 160

Trp Pro Tyr Tyr Thr Glu Asp Gly Gly Glu Val Ile Thr Val Phe Pro
                165                 170                 175

Ile Asp Glu Lys Leu Arg Tyr Leu Ile Pro Phe Arg Pro Val Lys Lys
            180                 185                 190

Thr Ile Glu Tyr Leu Glu Ser Leu Thr Ser Asp Asp Pro Ser Lys Val
        195                 200                 205

Ala Val Phe His Asp Asp Gly Glu Lys Phe Gly Val Trp Pro Gly Thr
    210                 215                 220

Tyr Glu Trp Val Tyr Glu Lys Gly Trp Leu Arg Glu Phe Phe Asp Ala
225                 230                 235                 240

Ile Thr Ser Asn Glu Lys Ile Asn Leu Met Thr Tyr Ser Glu Tyr Leu
```

```
            245                 250                 255
Ser Lys Phe Thr Pro Arg Gly Leu Val Tyr Leu Pro Ile Ala Ser Tyr
            260                 265                 270
Phe Glu Met Ser Glu Trp Ser Leu Pro Ala Lys Gln Ala Lys Leu Phe
            275                 280                 285
Val Glu Phe Val Glu Gln Leu Lys Glu Gly Lys Phe Glu Lys Tyr
            290                 295                 300
Arg Val Phe Val Arg Gly Gly Ile Trp Lys Asn Phe Phe Phe Lys Tyr
305                     310                 315                 320
Pro Glu Ser Asn Phe Met His Lys Arg Met Leu Met Val Ser Lys Ala
                    325                 330                 335
Val Arg Asp Asn Pro Glu Ala Arg Lys Tyr Ile Leu Lys Ala Gln Cys
                340                 345                 350
Asn Asp Ala Tyr Trp His Gly Val Phe Gly Ile Tyr Leu Pro His
                355                 360                 365
Leu Arg Arg Thr Val Trp Glu Asn Ile Ile Lys Ala Gln Arg Tyr Leu
            370                 375                 380
Lys Pro Glu Asn Lys Ile Leu Asp Val Asp Phe Asp Gly Arg Ala Glu
385                     390                 395                 400
Ile Met Val Glu Asn Asp Gly Phe Ile Ala Thr Ile Lys Pro His Tyr
                    405                 410                 415
Gly Gly Ser Ile Phe Glu Leu Ser Ser Lys Arg Lys Ala Val Asn Tyr
                420                 425                 430
Asn Asp Val Leu Pro Arg Arg Trp Glu His Tyr His Glu Val Pro Glu
                435                 440                 445
Ala Thr Lys Pro Glu Lys Glu Ser Glu Glu Gly Ile Ala Ser Ile His
            450                 455                 460
Glu Leu Gly Lys Gln Ile Pro Glu Glu Ile Arg Arg Glu Leu Ala Tyr
465                     470                 475                 480
Asp Trp Gln Leu Arg Ala Ile Leu Gln Asp His Phe Ile Lys Pro Glu
                    485                 490                 495
Glu Thr Leu Asp Asn Tyr Arg Leu Val Lys Tyr His Glu Leu Gly Asp
                500                 505                 510
Phe Val Asn Gln Pro Tyr Glu Tyr Glu Met Ile Glu Asn Gly Val Lys
                515                 520                 525
Leu Trp Arg Glu Gly Gly Val Tyr Ala Glu Lys Ile Pro Ala Arg
            530                 535                 540
Val Glu Lys Lys Ile Glu Leu Thr Glu Asp Gly Phe Ile Ala Lys Tyr
545                     550                 555                 560
Arg Val Leu Leu Glu Lys Pro Tyr Lys Ala Leu Phe Gly Val Glu Ile
                    565                 570                 575
Asn Leu Ala Val His Ser Val Met Glu Lys Pro Glu Glu Phe Glu Ala
                580                 585                 590
Lys Glu Phe Glu Val Asn Asp Pro Tyr Gly Ile Gly Lys Val Arg Ile
                595                 600                 605
Glu Leu Asp Lys Ala Ala Lys Val Trp Lys Phe Pro Ile Lys Thr Leu
            610                 615                 620
Ser Gln Ser Glu Ala Gly Trp Asp Phe Ile Gln Gln Gly Val Ser Tyr
625                     630                 635                 640
Thr Met Leu Phe Pro Ile Glu Lys Glu Leu Glu Phe Thr Val Arg Phe
                    645                 650                 655
Arg Glu Leu
```

```
<210> SEQ ID NO 15
<211> LENGTH: 503
<212> TYPE: PRT
<213> ORGANISM: Oceanithermus profundus DSM 14977

<400> SEQUENCE: 15

Met Glu Leu Pro Arg Ser Phe Gly Ile Leu His Pro Thr Ser Phe
1               5                   10                  15

Pro Gly Pro Tyr Pro Ile Gly Asn Leu Gly Asp Glu Ala Arg Ser Phe
                20                  25                  30

Leu Asp Trp Leu Ala Ala Thr Gly Ala Arg Trp Trp Gln Val Leu Pro
            35                  40                  45

Leu Gly Pro Thr Gly Phe Gly Asp Ser Pro Tyr Gln Ala Phe Ser Ala
        50                  55                  60

Phe Ala Gly Asn Pro Tyr Leu Ile Asp Pro Arg Arg Leu Val Ala Arg
65                  70                  75                  80

Gly Trp Leu Glu Ala Ala Asp Pro Pro Glu Ser Pro Pro Asp Arg Val
                85                  90                  95

Asp Tyr Gly Leu Val Tyr Arg Trp Ile Trp Pro Leu Leu Arg Arg Ala
                100                 105                 110

Tyr Ala Gly Phe Arg Ala Arg Ala Thr Arg Glu Asp Thr His Ala Leu
            115                 120                 125

Ala Val Phe Glu Arg Glu His Ala Asp Trp Leu Glu Asp Tyr Ala Leu
        130                 135                 140

Phe Met Ala Leu Lys Gly Glu His Gly Gly Ala Pro Trp Trp Ser Trp
145                 150                 155                 160

Pro Glu Pro Leu Lys Arg Arg Asp Pro Gly Ala Leu Ala Ala Ala Arg
                165                 170                 175

Glu Arg Leu Ala Glu Glu Ala Ala Phe Gln Arg Trp Thr Gln Trp Val
            180                 185                 190

Phe Phe Ser Gln Trp Arg Ala Leu Ala Asn Ala Ala His Asp Leu Gly
        195                 200                 205

Leu Gly Ile Val Gly Asp Met Pro Ile Phe Val Ala His Asp Ser Ala
    210                 215                 220

Asp Val Trp Ala His Pro Glu Leu Phe Gln Leu Asp Glu Asp Leu Asn
225                 230                 235                 240

Pro Val Ala Val Ala Gly Val Pro Pro Asp Tyr Phe Ser Pro Thr Gly
                245                 250                 255

Gln Leu Trp Gly Asn Pro Leu Tyr Asp Trp Asp Ala Leu Glu Arg Ser
            260                 265                 270

Gly Phe Asp Trp Trp Leu Arg Arg Ile Arg Arg Ala Leu Glu Thr Ala
        275                 280                 285

Asp Leu Val Arg Ile Asp His Phe Arg Gly Phe Glu Ala Tyr Trp Ala
    290                 295                 300

Val Pro Ala Gly Ala Pro Thr Ala Glu His Gly Arg Trp Glu Lys Ala
305                 310                 315                 320

Pro Gly Glu Ala Phe Phe Arg Lys Val Glu Ala Thr Phe Gly Ser Val
                325                 330                 335

Pro Ile Leu Ala Glu Asp Leu Gly Leu Ile Thr Pro Glu Val Glu Ala
            340                 345                 350

Leu Arg Asp Arg Phe Gly Leu Pro Gly Met Lys Val Leu Gln Phe Ala
        355                 360                 365

Phe Thr Gly Glu Asp Asn Pro Phe Leu Pro His Asn Tyr Pro Glu Ser
    370                 375                 380
```

```
Gly Asn Cys Val Val Tyr Thr Gly Thr His Asp Asn Asp Thr Thr Arg
385                 390                 395                 400

Gly Trp Cys Glu His Ala Pro Asp Ala Glu Leu Asp Phe Met Arg Arg
            405                 410                 415

Tyr Leu Glu Gly Arg Gly Ile Ala Cys Arg Gly Cys Gln Asp Ala Pro
            420                 425                 430

Trp Ala Leu Ile Glu Leu Ala Leu Gln Ser Arg Cys Arg Met Ala Val
            435                 440                 445

Phe Pro Leu Gln Asp Pro Leu Glu Leu Gly Ser Glu Ala Arg Met Asn
450                 455                 460

Phe Pro Ser Arg Pro Glu Gly Asn Trp Ala Trp Arg Tyr Ser Thr Arg
465                 470                 475                 480

Asp Leu Thr His Gly Leu Ala Glu Arg Leu Arg Gly Leu Ala Glu Arg
            485                 490                 495

Tyr Ala Arg Leu Arg Arg Gly
            500

<210> SEQ ID NO 16
<211> LENGTH: 500
<212> TYPE: PRT
<213> ORGANISM: Meiothermus silvanus strain ATCC 700542

<400> SEQUENCE: 16

Met Asp Ile Pro Arg Ser Phe Gly Ile Leu Leu His Pro Thr Ser Phe
1               5                   10                  15

Pro Gly Arg Trp Gly Ile Gly Thr Leu Gly Ala Glu Ala Arg Arg Phe
            20                  25                  30

Val Asp Trp Leu Ala Ser Thr Gly Ala His Trp Trp Gln Val Leu Pro
        35                  40                  45

Leu Gly Pro Thr Ser Tyr Gly Asp Ser Pro Tyr Gln Ser Phe Ser Ala
    50                  55                  60

Phe Ala Gly Asn Pro Tyr Leu Ile Asp Pro Asp Ile Leu Ile Glu Lys
65                  70                  75                  80

Gly Trp Leu Glu Pro Glu Glu Pro Pro Ala Tyr Pro Pro His Lys Val
                85                  90                  95

Asp Tyr Gly Trp Leu Tyr Val Thr Arg Trp Asp Leu Leu Arg Arg Ala
            100                 105                 110

Tyr Asp Gly Phe Val Gly Arg Gly Lys Pro Glu Asp Leu Glu Ala Phe
        115                 120                 125

Ala Arg Tyr Arg Gln Gln Glu Ala Asp Trp Leu Glu Asp Tyr Ala Leu
    130                 135                 140

Phe Met Ala Leu Lys His Ser Phe Gly Gly Arg Pro Trp Asn Glu Trp
145                 150                 155                 160

Thr Ala Pro Leu Arg Arg Arg Glu Pro Ala Ala Leu Glu Gln Ala Arg
                165                 170                 175

Lys Glu Tyr Ala Asp Glu Ile Gly Phe His Ala Trp Thr Gln Trp Val
            180                 185                 190

Phe Phe Gln Gln Trp Gly Asp Leu Arg Asn Tyr Ala His Ala Arg Gly
        195                 200                 205

Ile Lys Leu Ile Gly Asp Met Pro Ile Phe Leu Ala Tyr Asp Ser Ser
    210                 215                 220

Asp Val Trp Ala Asn Pro Gln Tyr Phe Tyr Leu Asp Ala Glu Gly Leu
225                 230                 235                 240

Pro Thr Val Val Ala Gly Val Pro Pro Asp Tyr Phe Ser Glu Thr Gly
```

```
            245                 250                 255
Gln Leu Trp Gly Asn Pro Leu Tyr Arg Trp Glu Val Met Gln Ala Glu
            260                 265                 270

Gly Phe Gly Trp Trp Ile His Arg Ile Lys Lys Ser Leu Glu Ala Cys
            275                 280                 285

Glu Leu Val Arg Ile Asp His Phe Arg Gly Phe Glu Ala Tyr Trp Glu
            290                 295                 300

Val Pro Phe Gly Glu Pro Thr Ala Val Lys Gly Arg Trp Val Lys Ala
305                 310                 315                 320

Pro Gly Lys Glu Leu Phe Gln Ala Val Arg Ala Ala Leu Gly Asp Ala
            325                 330                 335

Ala Ile Ile Ala Glu Asp Leu Gly Val Ile Thr Pro Glu Val Glu Glu
            340                 345                 350

Leu Arg Asp Ser Asn Gly Phe Pro Gly Met Lys Ile Leu Gln Phe Ala
            355                 360                 365

Phe Ser Asp Glu Thr Asn Pro Phe Leu Pro His Asn Tyr Pro Glu Ser
            370                 375                 380

Gly Asn Val Ile Val Tyr Thr Gly Thr His Asp Asn Asp Thr Thr Ile
385                 390                 395                 400

Gly Trp Tyr Gln Thr Ala Pro Lys Glu Glu Leu Ala Phe Met Asp Lys
            405                 410                 415

Tyr Leu Glu Gln Tyr Gly Leu Lys Ile Glu Lys Pro Glu Asp Ala Pro
            420                 425                 430

Trp Val Leu Ala Glu Leu Gly Phe Arg Ser Arg Ala Lys Leu Val Ile
            435                 440                 445

Leu Pro Leu Gln Asp Val Leu Arg Leu Gly Pro Glu Ala Arg Met Asn
            450                 455                 460

Phe Pro Gly Thr Leu Gly Asn Asn Trp Ser Trp Arg Tyr Ala Pro Gly
465                 470                 475                 480

Asp Leu Thr Pro Glu Leu Ala Leu His Leu Arg Glu Leu Ala Arg Ser
            485                 490                 495

Ser Asp Arg Leu
            500

<210> SEQ ID NO 17
<211> LENGTH: 511
<212> TYPE: PRT
<213> ORGANISM: Anaerolinea thermophila strain DSM 14523

<400> SEQUENCE: 17

Met Ser Leu Phe Lys Arg Ala Ser Gly Ile Leu Leu His Pro Thr Ser
1               5                   10                  15

Leu Pro Gly Pro Asp Gly Ile Gly Asp Leu Gly Pro Glu Ala Tyr Arg
            20                  25                  30

Trp Val Asn Phe Leu Ala Glu Ser Gly Cys Ser Leu Trp Gln Ile Leu
            35                  40                  45

Pro Leu Gly Pro Thr Gly Phe Gly Asp Ser Pro Tyr Gln Cys Phe Ser
            50                  55                  60

Ala Phe Ala Gly Asn Pro Tyr Leu Val Ser Pro Ala Leu Leu Leu Asp
65                  70                  75                  80

Glu Gly Leu Leu Thr Ser Glu Asp Leu Ala Asp Arg Pro Glu Phe Pro
            85                  90                  95

Ala Ser Arg Val Asp Tyr Gly Pro Val Ile Gln Trp Lys Leu Thr Leu
            100                 105                 110
```

```
Leu Asp Arg Ala Tyr Val Arg Phe Lys Arg Ser Thr Ser Gln Lys Arg
            115                 120                 125

Lys Ala Ala Phe Glu Ala Phe Lys Glu Glu Gln Arg Ala Trp Leu Leu
    130                 135                 140

Asp Phe Ser Leu Phe Met Ala Ile Lys Glu Ala His Gly Gly Ala Ser
145                 150                 155                 160

Trp Asp Tyr Trp Pro Glu Pro Leu Arg Lys Arg Asp Pro Glu Ala Leu
                165                 170                 175

Asn Ala Phe His Arg Ala His Glu Val Asp Val Glu Arg His Ser Phe
            180                 185                 190

Arg Gln Phe Leu Phe Arg Gln Trp Gln Ala Leu Arg Gln Tyr Ala
    195                 200                 205

His Glu Lys Gly Val Gln Ile Ile Gly Asp Val Pro Ile Phe Val Ala
210                 215                 220

Tyr Asp Ser Ala Asp Val Trp Ser His Pro Asp Leu Phe Tyr Leu Asp
225                 230                 235                 240

Glu Thr Gly Lys Pro Thr Val Val Ala Gly Val Pro Pro Asp Tyr Phe
                245                 250                 255

Ser Ala Thr Gly Gln Leu Trp Gly Asn Pro Leu Tyr Arg Trp Asp Tyr
            260                 265                 270

His Arg Glu Thr Gly Phe Ala Trp Trp Leu Glu Arg Leu Lys Ala Thr
    275                 280                 285

Phe Ala Met Val Asp Ile Val Arg Leu Asp His Phe Arg Gly Phe Ala
290                 295                 300

Gly Tyr Trp Glu Val Pro Tyr Gly Met Pro Thr Ala Glu Lys Gly Arg
305                 310                 315                 320

Trp Val Pro Gly Pro Gly Ile Ala Leu Phe Glu Ala Ile Arg Asn Ala
                325                 330                 335

Leu Gly Gly Leu Pro Ile Ile Ala Glu Asp Leu Gly Glu Ile Thr Pro
            340                 345                 350

Asp Val Ile Glu Leu Arg Glu Gln Leu Gly Leu Pro Gly Met Lys Ile
    355                 360                 365

Phe Gln Phe Ala Phe Ala Ser Asp Ala Asp Pro Phe Leu Pro His
370                 375                 380

Asn Tyr Val Gln Asn Cys Val Ala Tyr Thr Gly Thr His Asp Asn Asp
385                 390                 395                 400

Thr Ala Ile Gly Trp Tyr Asn Ser Ala Pro Glu Lys Glu Arg Asp Phe
                405                 410                 415

Val Arg Arg Tyr Leu Ala Arg Ser Gly Glu Asp Ile Ala Trp Asp Met
            420                 425                 430

Ile Arg Ala Val Trp Ser Ser Val Ala Met Phe Ala Ile Ala Pro Leu
    435                 440                 445

Gln Asp Phe Leu Lys Leu Gly Pro Glu Ala Arg Met Asn Tyr Pro Gly
450                 455                 460

Arg Pro Ala Gly Asn Trp Gly Trp Arg Tyr Glu Ala Phe Met Leu Asp
465                 470                 475                 480

Asp Gly Leu Lys Asn Arg Ile Lys Glu Ile Asn Tyr Leu Tyr Gly Arg
                485                 490                 495

Leu Pro Glu His Met Lys Pro Pro Lys Val Val Lys Lys Trp Thr
            500                 505                 510

<210> SEQ ID NO 18
<211> LENGTH: 488
<212> TYPE: PRT
```

<213> ORGANISM: Thermoanaerobacterium thermosaccharolyticum

<400> SEQUENCE: 18

```
Met Ala Leu Lys Asn Lys Val Gln Leu Ile Thr Tyr Pro Asp Ser Leu
1               5                   10                  15

Gly Gly Asn Leu Lys Thr Leu Asn Asp Val Leu Glu Lys Tyr Phe Ser
            20                  25                  30

Asp Val Phe Gly Gly Val His Ile Leu Pro Pro Phe Pro Ser Ser Gly
        35                  40                  45

Asp Arg Gly Phe Ala Pro Ile Thr Tyr Ser Glu Ile Glu Pro Lys Phe
    50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
            100                 105                 110

Thr Leu Asp Lys Leu Trp Lys Asp Gly Lys Pro Val Lys Gly Asp Ile
        115                 120                 125

Glu Lys Met Phe Leu Arg Arg Thr Leu Pro Tyr Ser Thr Phe Lys Ile
    130                 135                 140

Glu Glu Thr Gly Glu Glu Lys Val Trp Thr Thr Phe Gly Lys Thr
145                 150                 155                 160

Asp Pro Ser Glu Gln Ile Asp Leu Asp Val Asn Ser His Leu Val Arg
                165                 170                 175

Glu Phe Leu Leu Glu Val Phe Lys Thr Phe Ser Asn Phe Gly Val Lys
            180                 185                 190

Ile Val Arg Leu Asp Ala Val Gly Tyr Val Ile Lys Lys Ile Gly Thr
        195                 200                 205

Ser Cys Phe Phe Val Glu Pro Glu Ile Tyr Glu Phe Leu Asp Trp Ala
    210                 215                 220

Lys Gly Gln Ala Ala Ser Tyr Gly Ile Glu Leu Leu Leu Glu Val His
225                 230                 235                 240

Ser Gln Phe Glu Val Gln Tyr Lys Leu Ala Glu Arg Gly Phe Leu Ile
                245                 250                 255

Tyr Asp Phe Ile Leu Pro Phe Thr Val Leu Tyr Thr Leu Ile Asn Lys
            260                 265                 270

Ser Asn Glu Met Leu Tyr His Tyr Leu Lys Asn Arg Pro Ile Asn Gln
        275                 280                 285

Phe Thr Met Leu Asp Cys His Asp Gly Ile Pro Val Lys Pro Asp Leu
    290                 295                 300

Asp Gly Leu Ile Asp Thr Lys Lys Ala Lys Glu Val Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
            340                 345                 350

Ala Leu Asn Cys Asp Asp Asp Ala Tyr Leu Ala Ala Arg Ala Ile Gln
        355                 360                 365

Phe Phe Thr Pro Gly Ile Pro Gln Val Tyr Tyr Val Gly Leu Leu Ala
    370                 375                 380

Gly Val Asn Asp Phe Glu Ala Val Lys Lys Thr Lys Glu Gly Arg Glu
385                 390                 395                 400
```

Ile Asn Arg His Asn Tyr Gly Leu Lys Glu Ile Glu Ser Val Gln
                405                 410                 415

Lys Asn Val Val Gln Arg Leu Leu Lys Leu Ile Arg Phe Arg Asn Glu
                420                 425                 430

Tyr Glu Ala Phe Asn Gly Glu Phe Phe Ile Glu Asp Cys Arg Lys Asp
                435                 440                 445

Glu Ile Arg Leu Thr Trp Lys Lys Asp Asp Lys Arg Cys Ser Leu Phe
450                 455                 460

Ile Asp Leu Lys Thr Tyr Lys Thr Thr Ile Asp Tyr Ile Asn Glu Asn
465                 470                 475                 480

Gly Glu Glu Val Lys Tyr Leu Val
                485

<210> SEQ ID NO 19
<211> LENGTH: 488
<212> TYPE: PRT
<213> ORGANISM: Thermoanaerobacterium sp. PSU-2

<400> SEQUENCE: 19

Met Ala Leu Asn Asn Lys Val Gln Leu Ile Thr Tyr Pro Asp Ser Leu
1               5                   10                  15

Gly Gly Asp Leu Lys Thr Leu Asn Asp Val Leu Gly Lys Tyr Phe Tyr
                20                  25                  30

Asp Val Phe Gly Gly Ile His Ile Leu Pro Pro Phe Pro Ser Ser Gly
                35                  40                  45

Asp Arg Gly Phe Ala Pro Ile Thr Tyr Arg Glu Ile Glu Pro Lys Phe
            50                  55                  60

Gly Thr Trp His Asp Ile Lys Lys Met Ser Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
                100                 105                 110

Thr Leu Asp Lys Leu Trp Lys Asp Gly Lys Pro Val Lys Thr Asp Ile
                115                 120                 125

Glu Lys Met Phe Leu Arg Arg Thr Leu Pro Tyr Ser Thr Phe Lys Ile
            130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Ala Lys
                165                 170                 175

Glu Phe Leu Leu Gly Val Phe Lys Thr Phe Ser Asn Phe Gly Val Asn
                180                 185                 190

Ile Val Arg Leu Asp Ala Val Gly Tyr Val Ile Lys Lys Ile Gly Thr
            195                 200                 205

Ser Cys Phe Phe Val Glu Pro Glu Ile Tyr Glu Phe Leu Asn Trp Ile
210                 215                 220

Lys Gly Gln Ala Ala Ser Tyr Gly Ile Glu Leu Leu Leu Glu Val His
225                 230                 235                 240

Ser Gln Phe Glu Ile Gln Tyr Lys Leu Ala Glu Arg Asp Phe Trp Ile
                245                 250                 255

Tyr Asp Phe Ile Leu Pro Phe Thr Val Leu Tyr Thr Leu Ile Asn Lys
                260                 265                 270

Ser Asn Glu Met Leu Tyr Asp Tyr Leu Lys Asn Arg Pro Met Asn Gln
            275                 280                 285

```
Phe Thr Met Leu Asp Cys His Asp Gly Ile Pro Val Lys Pro Asp Leu
    290                 295                 300

Asp Gly Leu Ile Asp Thr Lys Lys Ala Lys Lys Val Val Asp Ile Cys
305                 310                 315                 320

Val Leu Arg Gly Ala Asn Leu Ser Leu Ile Tyr Gly Asp Lys Tyr Lys
                325                 330                 335

Ser Glu Asp Gly Phe Asp Val His Gln Ile Asn Cys Thr Tyr Tyr Ser
                340                 345                 350

Ala Leu Asn Cys Asp Asp Ala Tyr Leu Ala Ala Arg Ala Ile Gln
                355                 360                 365

Phe Phe Thr Pro Gly Ile Pro Gln Ile Tyr Tyr Val Gly Leu Leu Ala
    370                 375                 380

Gly Val Asn Asp Phe Glu Ala Val Lys Arg Thr Lys Glu Gly Arg Glu
385                 390                 395                 400

Ile Asn Arg His Asn Tyr Ser Leu Asn Glu Ile Glu Glu Ser Val Lys
                405                 410                 415

Glu Asp Val Val Gln Arg Leu Lys Leu Ile Arg Phe Arg Asn Arg
                420                 425                 430

Tyr Glu Ala Phe Asn Gly Glu Phe Leu Val Glu Asp Cys Lys Asp Asp
                435                 440                 445

Glu Ile Arg Leu Thr Trp Glu Lys Asp Lys Arg Cys Ser Leu Phe
    450                 455                 460

Ile Asp Leu Lys Thr Tyr Lys Thr Val Ile Asn Tyr Ile Asp Glu Asn
465                 470                 475                 480

Gly Arg Glu Val Glu Tyr Val Val
                485

<210> SEQ ID NO 20
<211> LENGTH: 488
<212> TYPE: PRT
<213> ORGANISM: Thermoanaerobacterium thermosaccharolyticum

<400> SEQUENCE: 20

Met Ala Leu Asn Asn Lys Val Gln Leu Ile Thr Tyr Pro Asp Ser Leu
1               5                   10                  15

Gly Gly Asp Leu Lys Thr Leu Asn Asp Val Leu Glu Lys Tyr Phe Ser
                20                  25                  30

Asp Val Phe Gly Gly Ile His Ile Leu Pro Pro Phe Pro Ser Ser Gly
                35                  40                  45

Asp Arg Gly Phe Ala Pro Ile Thr Tyr Ser Glu Ile Glu Pro Lys Phe
                50                  55                  60

Gly Thr Trp Tyr Asp Ile Lys Lys Met Ala Glu Asn Phe Asp Ile Leu
65                  70                  75                  80

Leu Asp Leu Met Val Asn His Val Ser Arg Arg Ser Ile Tyr Phe Gln
                85                  90                  95

Asp Phe Leu Lys Lys Gly Arg Lys Ser Glu Tyr Ala Asp Met Phe Ile
                100                 105                 110

Thr Leu Asp Lys Leu Trp Lys Asp Gly Lys Pro Val Lys Gly Asp Ile
                115                 120                 125

Glu Lys Met Phe Leu Arg Arg Thr Leu Pro Tyr Ser Thr Phe Lys Ile
                130                 135                 140

Glu Glu Thr Gly Glu Glu Glu Lys Val Trp Thr Thr Phe Gly Lys Thr
145                 150                 155                 160

Asp Pro Ser Glu Gln Ile Asp Leu Asp Val Asn Ser His Leu Val Lys
```

```
            165                 170                 175
Glu Phe Leu Leu Glu Val Phe Arg Thr Phe Ser Asn Phe Gly Val Asn
            180                 185                 190

Ile Val Arg Leu Asp Ala Val Gly Tyr Val Ile Lys Lys Ile Gly Thr
            195                 200                 205

Ser Cys Phe Phe Val Glu Pro Glu Ile Tyr Glu Phe Leu Asp Trp Ala
    210                 215                 220

Lys Gly Gln Ala Ala Ser Tyr Gly Ile Glu Leu Leu Glu Val His
225                 230                 235                 240

Ser Gln Phe Glu Ile Gln Tyr Lys Leu Ala Glu Arg Gly Phe Trp Ile
                245                 250                 255

Tyr Asp Phe Ile Leu Pro Phe Thr Val Leu Tyr Thr Leu Ile Asn Lys
            260                 265                 270

Ser Asn Glu Met Leu Tyr Asp Tyr Leu Lys Asn Arg Pro Ile Asn Gln
        275                 280                 285

Phe Thr Met Leu Asp Cys His Asp Gly Ile Pro Val Lys Pro Asp Leu
    290                 295                 300

Asp Gly Leu Ile Asp Thr Lys Lys Ala Arg Asp Val Asp Ile Cys
305                 310                 315                 320

Val Gln Arg Gly Ala Asn Leu Ser Leu Ile Tyr Gly Asp Lys Tyr Lys
                325                 330                 335

Ser Glu Asp Gly Phe Asp Val His Gln Ile Gly Cys Thr Tyr Tyr Ser
            340                 345                 350

Ala Leu Asn Cys Asp Asp Asp Ala Tyr Leu Ala Ala Arg Ala Ile Gln
        355                 360                 365

Phe Phe Thr Pro Gly Ile Pro Gln Val Tyr Tyr Val Gly Leu Leu Ala
    370                 375                 380

Gly Val Asn Asp Phe Glu Ala Val Lys Lys Thr Lys Glu Gly Arg Glu
385                 390                 395                 400

Ile Asn Arg His Asn Tyr Gly Leu Lys Glu Ile Glu Glu Ser Val Gln
                405                 410                 415

Lys Lys Ala Val Gln Arg Leu Leu Lys Leu Ile Arg Phe Arg Asn Glu
            420                 425                 430

Tyr Glu Ala Phe Asn Gly Glu Phe Met Val Gln Asp Cys Gln Lys Asp
        435                 440                 445

Glu Ile Arg Leu Thr Trp Lys Lys Asp Lys Arg Cys Ser Leu Phe
    450                 455                 460

Ile Asp Leu Lys Thr Tyr Lys Thr Thr Ile Asp Tyr Ile Asn Glu Asn
465                 470                 475                 480

Gly Glu Glu Val Lys Tyr Leu Val
                485

<210> SEQ ID NO 21
<211> LENGTH: 488
<212> TYPE: PRT
<213> ORGANISM: Thermoanaerobacterium xylanolyticum

<400> SEQUENCE: 21

Met Ala Leu Asn Asn Lys Val Gln Leu Ile Thr Tyr Pro Asp Ser Leu
1               5                   10                  15

Gly Gly Asp Leu Lys Thr Leu Asn Asp Val Leu Glu Lys Tyr Phe Ser
            20                  25                  30

Asp Val Phe Gly Gly Ile His Ile Leu Pro Pro Phe Pro Ser Ser Gly
        35                  40                  45
```

```
Asp Arg Gly Phe Ala Pro Ile Thr Tyr Ser Glu Ile Asp Pro Lys Phe
    50              55                  60

Gly Ser Trp Tyr Asp Ile Lys Lys Met Ala Asp Asn Phe Asp Ile Leu
 65              70              75                  80

Leu Asp Leu Met Val Asn His Val Ser Arg Arg Ser Ile Tyr Phe Gln
                85              90                  95

Asp Phe Leu Lys Lys Gly Arg Met Ser Glu Tyr Ala Asp Met Phe Ile
            100             105                 110

Thr Leu Asp Lys Leu Trp Lys Asp Gly Lys Pro Val Lys Thr Asp Ile
            115             120                 125

Glu Lys Met Phe Leu Arg Arg Thr Leu Pro Tyr Ser Thr Phe Lys Ile
130             135                 140

Glu Glu Thr Gly Glu Glu Arg Val Trp Thr Thr Phe Gly Lys Thr
145                 150             155                 160

Asp Pro Ser Glu Gln Ile Asp Leu Asp Val Asn Ser His Leu Val Arg
                165             170                 175

Glu Phe Leu Leu Glu Val Phe Lys Thr Phe Ser Asn Phe Gly Val Asn
            180             185                 190

Ile Val Arg Leu Asp Ala Val Gly Tyr Val Ile Lys Lys Met Gly Thr
            195             200                 205

Ser Cys Phe Phe Val Glu Pro Asp Ile Tyr Glu Phe Leu Asn Trp Ile
    210             215                 220

Lys Gly Gln Ala Ala Ser Tyr Gly Ile Glu Leu Leu Leu Glu Val His
225             230             235                 240

Ser Gln Phe Glu Val Gln Tyr Lys Leu Ala Glu Arg Gly Phe Trp Ile
                245             250                 255

Tyr Asp Phe Ile Leu Pro Phe Thr Val Leu Tyr Thr Leu Ile Asn Arg
            260             265                 270

Ser Asn Glu Met Leu Tyr Asp Tyr Leu Lys Asn Arg Pro Met Asn Gln
            275             280                 285

Phe Thr Met Leu Asp Cys His Asp Gly Ile Pro Val Lys Pro Asp Leu
    290             295                 300

Asp Gly Leu Ile Asp Thr Lys Lys Ala Lys Glu Val Val Asp Ile Cys
305             310             315                 320

Val Gln Arg Gly Ala Asn Leu Ser Leu Ile Tyr Gly Asp Lys Tyr Lys
            325             330                 335

Ser Glu Asp Gly Phe Asp Val His Gln Ile Gly Cys Thr Tyr Tyr Ser
            340             345                 350

Ala Leu Asn Cys Asp Asp Asp Ala Tyr Leu Ala Ala Arg Ala Ile Gln
    355             360                 365

Phe Phe Thr Pro Gly Ile Pro Gln Val Tyr Tyr Val Gly Leu Leu Ala
    370             375                 380

Gly Val Asn Asp Phe Glu Ala Val Lys Arg Thr Lys Glu Gly Arg Glu
385             390             395                 400

Ile Asn Arg His Asn Tyr Gly Leu Asn Glu Ile Glu Glu Ser Val Gln
                405             410                 415

Lys Asp Val Val Gln Arg Leu Leu Lys Leu Ile Arg Phe Arg Asn Arg
            420             425                 430

Tyr Glu Ala Phe Asn Gly Glu Phe Leu Val Glu Asp Cys Lys Asp Asp
            435             440                 445

Glu Ile Arg Leu Thr Trp Glu Lys Asp Lys His Cys Ser Leu Phe
    450             455                 460

Ile Asp Leu Gly Ser Tyr Arg Thr Ile Val Asn Tyr Val Asp Glu Asn
```

Gly Lys Asp Val Glu Tyr Ile Val
465                 470                 475                 480
            485

<210> SEQ ID NO 22
<211> LENGTH: 488
<212> TYPE: PRT
<213> ORGANISM: Thermobacillus sp. ZCTH02-B1

<400> SEQUENCE: 22

Met Lys Leu Glu Asn Arg Val Gln Leu Ile Thr Tyr Pro Asp Ser Leu
1               5                   10                  15

Gly Gly Asn Leu Ala Ala Leu Arg Glu Val Leu Arg Arg His Phe Pro
            20                  25                  30

Gly Leu Phe Leu Gly Gly Ile His Ile Leu Pro Pro Phe Pro Ser Ser
        35                  40                  45

Gly Asp Arg Gly Phe Ala Pro Leu Asp Tyr Gly Met Ile Asp Pro Ala
    50                  55                  60

Phe Gly Thr Trp Glu Asp Ile Ala Gln Leu Gly Glu Glu Tyr Gly Val
65                  70                  75                  80

Met Leu Asp Val Met Val Asn His Ile Ser Arg Arg Ser Pro Gln Phe
                85                  90                  95

Met Asp Phe Leu Lys Gln Gly Arg Ser Ser Pro Tyr Ala Asp Met Phe
            100                 105                 110

Leu Thr Leu Asp Lys Ile Trp Pro Asp Gly Arg Pro Val Gln Ala Asp
        115                 120                 125

Ile Asp Lys Met Phe Leu Arg Arg Lys Leu Pro Tyr Ser Ala Phe Thr
    130                 135                 140

Val Gly Asp Gly Arg Glu Glu Leu Val Trp Thr Thr Phe Gly Lys Thr
145                 150                 155                 160

Asp Pro Ser Glu Gln Ile Asp Leu Asp Val Arg Ser Pro Leu Ala Arg
                165                 170                 175

His Tyr Leu Ser Gly Ile Phe Gln Arg Phe Lys Ala Asn Arg Val Asn
            180                 185                 190

Met Val Arg Leu Asp Ala Val Gly Tyr Val Ile Lys Lys Pro Gly Thr
        195                 200                 205

Ser Cys Phe Phe Val Glu Pro Asp Ile Tyr Glu Phe Leu Asp Trp Val
    210                 215                 220

Ala Asp Gln Ala Lys Glu His Asp Ile Ala Leu Leu Pro Glu Val His
225                 230                 235                 240

Ala His Tyr Ser Ile Gln Tyr Lys Leu Ala Glu Arg Gly Phe Trp Ile
                245                 250                 255

Tyr Asp Phe Ile Leu Pro Phe Met Val Leu Asp Ala Leu Val Asn Arg
            260                 265                 270

Ser Ser Ala Met Leu Leu Arg Tyr Leu Arg Thr Arg Pro Ala Asn Gln
        275                 280                 285

Phe Thr Met Leu Asp Cys His Asp Gly Ile Pro Val Lys Pro Asp Leu
    290                 295                 300

Asp Asp Leu Val Asp Thr Ala Gln Ala Arg Arg Val Val Asp Leu Cys
305                 310                 315                 320

Leu Ala Arg Gly Ala Asn Leu Ser Tyr Val Ile Ser Asp Arg His Lys
                325                 330                 335

Ser Pro Asp Gly Phe Asp Val His Gln Ile Arg Cys Thr Tyr Tyr Asp
            340                 345                 350

```
Ala Leu Gly Arg Asn Asp Asp Ala Tyr Leu Ala Ala Arg Ala Ile Gln
            355                 360                 365

Leu Phe Val Pro Gly Ile Pro Gln Ile Tyr Tyr Val Gly Leu Leu Ala
    370                 375                 380

Gly Glu Asn Asp Pro Ala Arg Ala Glu Ala Thr Gly Asp Gly Arg Glu
385                 390                 395                 400

Ile Asn Arg His Asn Tyr Thr Leu Glu Glu Ile Glu Gln Ala Val Arg
                405                 410                 415

Arg Pro Val Val Gln Arg Leu Leu Lys Leu Ile Arg Phe Arg Asn Glu
            420                 425                 430

His Glu Ala Phe Gln Gly Ser Phe Arg Val Cys Glu Ser Glu Asp Ser
        435                 440                 445

Lys Ile Arg Leu Glu Trp Glu Lys Asp Ala Ile Arg Cys Ala Leu His
    450                 455                 460

Val Asp Leu Asp Thr Tyr Arg Ser Ile Ile Thr Cys Thr Asp Gly Gln
465                 470                 475                 480

Gly Lys Glu Ala Gln Trp Val Val
                485
```

<210> SEQ ID NO 23
<211> LENGTH: 504
<212> TYPE: PRT
<213> ORGANISM: Bifidobacterium adolescentis

<400> SEQUENCE: 23

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240
```

Val Glu Ile Ala Ser Lys Val Asp Arg Val Tyr Asp Phe Ala Leu Pro
            245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
            275                 280                 285

His Asp Gly Ile Gly Val Ile Asp Ile Gly Ser Asp Gln Leu Asp Arg
            290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
                340                 345                 350

Ala Leu Gly Cys Asn Asp Gln His Tyr Ile Ala Ala Arg Ala Val Gln
                355                 360                 365

Phe Phe Leu Pro Gly Val Pro Gln Val Tyr Tyr Val Gly Ala Leu Ala
            370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
            435                 440                 445

Ser Ile Ser Phe Thr Trp Arg Gly Glu Thr Ser Gln Ala Thr Leu Thr
            450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 24
<211> LENGTH: 480
<212> TYPE: PRT
<213> ORGANISM: Paenibacillus thermophilus

<400> SEQUENCE: 24

Met Lys Ile Lys Asn Glu Ala Met Leu Ile Thr Tyr Ala Asp Ser Leu
1               5                   10                  15

Gly Thr Asn Leu Lys Glu Leu Asn Gln Val Leu Asp Lys His Leu Gln
            20                  25                  30

Gly Val Val Gly Gly Val His Leu Leu Pro Phe Tyr Pro Ser Ser Gly
            35                  40                  45

Asp Arg Gly Phe Ala Pro Met Asp Tyr Thr Lys Val Asp Pro Ala Phe
        50                  55                  60

Gly Asp Trp Ser Asp Val Glu Gln Met Ser Gln Lys Tyr Tyr Met Met
65                  70                  75                  80

Tyr Asp Phe Met Ile Asn His Ile Ser Arg Gln Ser Pro Tyr Phe Gln
                85                  90                  95

Asp Phe Leu Glu Asn Lys Asp Glu Ser Ala Tyr Lys Asp Leu Phe Ile

```
                100             105              110
Arg Tyr Lys Asn Phe Trp Pro Gly Gly Glu Pro Thr Pro Glu Asp Val
            115             120             125

Asp Leu Ile Tyr Lys Arg Lys Pro Arg Ala Pro Tyr Val Glu Val Thr
            130             135             140

Phe Lys Asp Gly Ser Thr Glu Lys Val Trp Cys Thr Phe Asp Glu Gln
145             150             155             160

Gln Ile Asp Leu Asp Val Thr Thr Asp Thr Thr Lys Lys Phe Ile Arg
            165             170             175

Asp Asn Leu Thr Phe Leu Ala Gln Lys Gly Ala Ser Ile Ile Arg Leu
            180             185             190

Asp Ala Phe Ala Tyr Ala Asn Lys Lys Ile Gly Thr Asn Cys Phe Phe
            195             200             205

Val Glu Pro Asp Ile Trp Asp Met Leu Arg Tyr Ser Lys Asp Ile Ile
            210             215             220

Ser Pro Ser Gly Ile Thr Val Leu Pro Glu Ile His Glu His Tyr Ser
225             230             235             240

Ile Gln Leu Lys Ile Ala Glu Gln Asp Tyr Tyr Val Tyr Asp Phe Ala
            245             250             255

Leu Pro Met Leu Val Leu His Ala Leu Tyr Ser Gly Gln Val His Arg
            260             265             270

Leu Val His Trp Leu Asn Ile Cys Pro Arg Lys Gln Phe Thr Thr Leu
            275             280             285

Asp Thr His Asp Gly Ile Gly Val Asp Val Lys Asp Leu Leu Ser
            290             295             300

Asp Glu Glu Cys Glu Met Thr Arg Glu Ser Leu Tyr Ser Gln Gly Ala
305             310             315             320

Asn Val Lys Lys Ile Tyr Ser Thr Glu Ala Tyr Asn Asn Leu Asp Ile
            325             330             335

Tyr Gln Ile Asn Cys Thr Tyr Tyr Ser Ala Leu Gly Asn Asn Asp Gln
            340             345             350

Ser Tyr Leu Leu Ala Arg Ala Ile Gln Cys Phe Ala Pro Gly Ile Pro
            355             360             365

Gln Ile Tyr Tyr Val Gly Leu Leu Ala Gly Glu Asn Asp Ile Glu Leu
            370             375             380

Leu Glu Arg Thr Lys Glu Gly Arg Asn Ile Asn Arg His Tyr Tyr Thr
385             390             395             400

Leu Glu Glu Ile Glu Arg Glu Val Glu Arg Pro Val Val Lys Gln Leu
            405             410             415

Phe Arg Leu Leu Lys Phe Arg Asn Thr Cys Pro Ala Phe Asp Gly Thr
            420             425             430

Val Glu Ala Glu Gln Ala Asp Ile Asn Asn Leu Arg Ile Ile Trp Lys
            435             440             445

Asn Gly Ala Ser Glu Ala Lys Leu Glu Ala Asn Leu Ala Thr Lys Glu
            450             455             460

Phe Ser Ile Arg Tyr Lys Asp Ala Glu Thr Asn Trp Thr Leu Leu Met
465             470             475             480

<210> SEQ ID NO 25
<211> LENGTH: 489
<212> TYPE: PRT
<213> ORGANISM: Tepidibacillus decaturensis

<400> SEQUENCE: 25
```

```
Met Asn Val Lys Asn Gln Val Gln Leu Ile Thr Tyr Pro Asp Ser Leu
1               5                   10                  15

Gly Gly Asn Leu Lys Asn Leu His His Val Leu Leu Lys Tyr Phe Val
            20                  25                  30

Asp Ile Phe Lys Gly Gly Val His Ile Leu Pro Pro Tyr Pro Ser Ser
            35                  40                  45

Gly Asp Arg Gly Phe Ala Pro Ile Asn Tyr Leu Glu Ile Asp Pro Arg
50                      55                  60

Phe Gly Thr Trp Ala Asp Ile Lys Ala Ile Gly Glu Asn Phe Asp Val
65                  70                  75                  80

Met Leu Asp Leu Met Val Asn His Ile Ser Arg Gln Ser Leu Tyr Phe
                85                  90                  95

Gln Asp Phe Leu Lys Lys Gly Arg Gln Ser Glu Tyr Ala Asp Met Phe
                100                 105                 110

Ile Thr Leu Asp Lys Ile Trp Asp Asp Gly Glu Pro Val Gln Glu Asp
            115                 120                 125

Ile Asp Lys Met Phe Leu Arg Arg Pro Leu Pro Tyr Ser Thr Phe Ser
            130                 135                 140

Ile Lys Glu Thr Gly Glu Gln Glu Arg Val Trp Thr Thr Phe Gly Lys
145                 150                 155                 160

Thr Asp Pro Ser Glu Gln Ile Asp Leu Asp Ile Lys Ser Gln Lys Val
                165                 170                 175

Lys Gln Leu Leu Thr Ser Phe Phe Gln Asn Phe Lys Gln Gln Asn Val
                180                 185                 190

Lys Met Val Arg Leu Asp Ala Val Gly Tyr Val Ile Lys Lys Leu Gly
                195                 200                 205

Thr Ser Cys Phe Phe Val Glu Pro Asp Ile Tyr Asp Phe Leu Asp Trp
                210                 215                 220

Met Arg Glu Ile Ala Asp Ser Met Glu Ile Glu Leu Leu Pro Glu Val
225                 230                 235                 240

His Ala His Tyr Ser Ile Gln Tyr Lys Leu Ala Glu His Gly Phe Trp
                245                 250                 255

Ile Tyr Asp Phe Ile Leu Pro Tyr Arg Ile Leu Asp Ala Leu Val Asn
                260                 265                 270

Lys Ser Ser Lys Asp Leu Leu Asp Tyr Leu Lys Asn Arg Pro His Lys
                275                 280                 285

Gln Val Thr Met Leu Asp Cys His Asp Gly Ile Pro Val Lys Pro Asp
                290                 295                 300

Leu Asp Asp Leu Ile Asp Thr Lys Glu Ala Arg Lys Leu Val Asn Val
305                 310                 315                 320

Cys Leu Glu Arg Gly Ser Asn Leu Ser Leu Ile Leu Ser His Glu His
                325                 330                 335

Lys Asp Lys Asp Gly Phe Asp Val His Gln Ile Arg Cys Ser Tyr Tyr
                340                 345                 350

Ser Val Leu Asn Arg Asp Asp Ala Tyr Leu Ala Ala Arg Ala Ile
                355                 360                 365

Gln Phe Phe Thr Pro Gly Ile Pro Gln Val Tyr Tyr Val Gly Leu Leu
370                 375                 380

Ala Gly Glu Asn Asp Met Glu Gly Val Lys Lys Thr Gly Glu Gly Arg
385                 390                 395                 400

Glu Ile Asn Arg His Asn Phe Ser Leu Asp Glu Ile Glu His Ser Leu
                405                 410                 415

Asn Lys Lys Val Val Gln Arg Leu Leu Gln Leu Ile Arg Phe Arg Asn
```

```
                420            425              430
Glu Tyr Asp Ala Phe Asn Gly Glu Phe Lys Val Leu Asp Ser Ala Gln
            435                 440                 445

Asp Glu Ile Arg Leu Ser Trp Gln Lys Glu Lys Arg Cys Thr Leu
    450                 455                 460

Gln Ile Asp Leu Lys Thr Asn Lys Ser Val Ile Glu Tyr Val Asp Glu
465                 470                 475                 480

Lys Asp Gly Glu Ile Pro Tyr Phe Ile
                485

<210> SEQ ID NO 26
<211> LENGTH: 504
<212> TYPE: PRT
<213> ORGANISM: Thermanaerothrix daxensis

<400> SEQUENCE: 26

Met Lys Asn Gln Val Gln Leu Ile Thr Tyr Val Asp Arg Leu Gly Ser
1               5                   10                  15

Gly Asn Ile Lys Thr Leu His Gln Leu Leu Arg Gly Pro Leu Ala Gly
                20                  25                  30

Leu Phe Gly Gly Val His Leu Leu Pro Phe Tyr Tyr Pro Ile Lys Gly
            35                  40                  45

Ala Asp Ala Gly Phe Asp Pro Ile Asp His Thr Arg Val Asp Pro Cys
        50                  55                  60

Leu Gly Ser Trp Glu Asp Ile Arg Ala Leu Gly Gln Asp Val Asp Leu
65                  70                  75                  80

Met Ala Asp Leu Ile Val Asn His Ile Ser Ser Ser Pro Gln Phe
                85                  90                  95

Leu Asp Tyr Leu Glu Lys Gly Asp Ser Ile Tyr Lys Asp Leu Phe
            100                 105                 110

Leu Thr Met Ser Ser Val Phe Pro Asn Gly Ala Thr Glu Ala Asp Leu
        115                 120                 125

Leu Thr Ile Tyr Arg Pro Arg Pro Gly Leu Pro Phe Ser Tyr Ile Thr
130                 135                 140

Leu Lys Asn Gly Gln Lys Arg Leu Leu Trp Thr Thr Phe Ser Arg Gln
145                 150                 155                 160

Gln Ile Asp Ile Asn Val Leu His Pro Met Gly Arg Glu Tyr Leu His
                165                 170                 175

Ser Val Leu Arg Thr Leu His Glu Asn Gly Ile Arg Met Val Arg Leu
            180                 185                 190

Asp Ala Val Gly Tyr Ala Val Lys Lys Ala Gly Thr Thr Cys Phe Met
        195                 200                 205

Ile Pro Glu Thr Phe Asp Phe Ile Glu Asn Leu Thr His Gln Ala Gln
    210                 215                 220

Glu Leu Gly Met Glu Val Leu Glu Ile His Ser His Tyr Arg Lys
225                 230                 235                 240

Gln Ile Glu Ile Ala Arg Gln Val Asp Arg Val Tyr Asp Phe Ala Leu
                245                 250                 255

Pro Pro Leu Val Leu His Ala Ile Phe Asn Arg Thr Ala Tyr Tyr Leu
            260                 265                 270

Lys Gln Trp Leu Ser Ile Ser Pro Arg Asn Ala Ile Thr Val Leu Asp
        275                 280                 285

Thr His Asp Gly Ile Gly Val Ile Asp Ile Gly Ala Asp Ser Ser Asp
    290                 295                 300
```

```
Pro Gln Asn Tyr Pro Gly Leu Ile Pro Pro Glu Glu Leu Glu Ala Leu
305                 310                 315                 320

Val Glu Gln Ile His Leu Asn Ser Asn Gly Gln Ser Arg Leu Ala Ser
                325                 330                 335

Gly Ala Ala Ala Ser Asn Leu Asp Leu Tyr Gln Val Asn Cys Thr Phe
                340                 345                 350

Tyr Asp Ala Leu Gly Arg Asn Asp Arg Asp Tyr Leu Leu Ala Arg Ala
            355                 360                 365

Ile Gln Phe Phe Ser Pro Gly Ile Pro Gln Val Tyr Tyr Val Gly Leu
        370                 375                 380

Leu Ala Gly Glu Asn Asp Met Asp Leu Leu Ala Arg Thr Gly Val Gly
385                 390                 395                 400

Arg Asp Ile Asn Arg His Tyr Tyr Thr Leu Glu Glu Ile Ala Gln Ala
                405                 410                 415

Ile Gln Arg Pro Val Val Gln Ser Leu Phe Arg Leu Ile Arg Phe Arg
                420                 425                 430

Asn Gln His Pro Ala Phe Asn Gly Ala Phe Ser Met Pro Glu Ser Pro
            435                 440                 445

Asp Ser Arg Leu Ile Leu Arg Trp Asp Asn Gly Ala Ala Trp Ala Val
        450                 455                 460

Leu Glu Val Asp Phe Ala Ala Gly Thr Phe Ser Ile Ser Gly Ser Pro
465                 470                 475                 480

Leu Glu Gly Ala Glu Pro Ile Glu Ala Leu Pro Gly Ala His Pro Asp
                485                 490                 495

Asn Arg Tyr Gly Gly Ile Ala Thr
            500
```

ENZYMATIC PRODUCTION OF HEXOSES

CROSS REFERENCE TO RELATED APPLICATIONS

This application claims priority to U.S. Application No. 62/752,061, filed on Oct. 29, 2018, and to U.S. Application No. 62/857,543, filed on Jun. 5, 2019, each herein incorporated by reference.

FIELD OF THE INVENTION

The invention relates to methods for the preparation of hexose monosaccharides. More specifically, the invention provides improved methods of preparation of an intermediate, glucose 6-phosphate (G6P), using enzymes with higher activities than those previously reported.

BACKGROUND

Hexoses are monosaccharides with six carbon atoms. Hexoses can be classified by functional group, with aldohexoses having an aldehyde at position 1, and ketohexoses having that ketone at position 2. Aldohexoses (or aldoses) include allose, altrose, glucose, gulose, galactose, idose, talose, and mannose. Ketohexoses (or ketoses) include psicose (allulose), fructose, tagatose, and sorbose. Inositol is a hexose with no aldehyde or ketose group, and is characterized as a carbocyclic sugar.

International Patent Application Publication No. WO2018/169957, herein incorporated by reference in its entirety, describes processes for preparing hexoses from saccharides by enzymatic conversion. International Patent Application Publication Nos. WO2017/059278 and WO2018/004310 herein incorporated by reference in their entirety, describes processes for preparing tagatose from saccharides by enzymatic conversion. International Patent Application Publication No. WO2018/112139 herein incorporated by reference in its entirety, describes processes for preparing allulose from saccharides by enzymatic conversion. KR Application Publication Number KR20040098757A herein incorporated by reference in its entirety, describes processes for preparing fructose 6-phosphate from saccharides by enzymatic conversion. CN Application Publication Number CN106148425B herein incorporated by reference in its entirety, describes processes for preparing inositol from saccharides by enzymatic conversion. In each of these processes, glucose 6-phosphate (G6P) is an intermediate in the enzymatic pathway.

Despite developments in enzymatic hexose production with high yields, there is still a need for providing further improved processes of producing hexoses that can, e.g., provide a higher yield with lower amounts of enzymes. There is a strong industrial and commercial interest in decreasing the cost of hexose production, and this decrease involves the use of a reduced amount of enzymes, enzymes with higher activity, and use of combinations of enzymes that are more effective in converting saccharides to the G6P intermediate.

SUMMARY OF THE INVENTION

The inventions described herein generally relate to improved processes for preparing a hexose by enzymatic conversion from various saccharide starting materials. The saccharides may be chosen from starch or starch derivatives, cellulose or cellulose derivatives, or sucrose. In improved processes of the invention, the enzymes used for the process steps, as indicated, have improved activities over enzymes previously disclosed for the preparation of hexoses.

In some improved processes of the invention for the enzymatic production of a hexose from starch or starch derivative, the improvement includes at least one of: a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; b) a step of converting a starch derivative to G1P, catalyzed by an alpha-glucan phosphorylase (αGP), wherein the αGP comprises an amino acid sequence having at least 90% sequence identity with any one of SEQ ID NOs: 10-13; and a step of transglycosylating a starch derivative, catalyzed by a 4-alpha-glucan transferase (4GT), wherein the 4GT comprises an amino acid sequence having at least 90% sequence identity with any one of SEQ ID NOs: 15-17.

In some improved processes of the invention for the enzymatic production of a hexose from cellulose or cellulose derivative, the improvement includes a step of converting G1P to glucose 6-phosphate (G6P), catalyzed by a phosphoglucomutase (PGM), wherein the PGM comprises an amino acid sequence having at least 90% sequence identity with any one of SEQ ID NOs: 2-8.

In some improved processes of the invention for the enzymatic production of a hexose from sucrose, the improvement includes at least one of a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; and b) a step of converting sucrose to glucose 1-phosphate (G1P) using a sucrose phosphorylase, wherein the sucrose phosphorylase comprises an amino acid sequence having at least 90% sequence identity with any one of SEQ ID NOs: 19-25.

In some improved processes of the invention the hexose is selected from allose, mannose, galactose, fructose, altrose, talose, sorbose, gulose idose, allulose, inositol, and tagatose. Some improved processes of the invention further include a step of dephosphorylating the hexose-phosphate using a hexose phosphate phosphatase.

In some improved processes of the invention, the process steps are conducted in a single reaction vessel. In other improved processes of the invention, the process steps are conducted in more than one reaction vessels. In some improved process of the invention, the process steps are conducted ATP-free, NAD(P)(H)-free, at a phosphate concentration from about 0.1 mM to about 150 mM, the phosphate is recycled, and/or the step of dephosphorylation of the hexose phosphate involves an energetically favorable chemical reaction. In some improved processes of the invention, the process steps are conducted under at least one of the following process conditions: at a temperature ranging from about 37° C. to about 85° C., at a pH ranging from about 5.0 to about 8.0, or for about 0.5 hours to about 48 hours. In some improved process of the invention, the process steps are conducted as a continuous reaction.

BRIEF DESCRIPTION OF THE FIGURES

FIG. 12 is a schematic diagram showing an enzymatic pathway converting G6P to idose. The following abbreviations are used: PGI, phosphoglucoisomerase; F6PE, fructose 6-phosphate epimerase; S6PE, sorbose 6-phosphate epimerase; I6PI, idose 6-phosphate isomerase; I6PP, idose 6-phosphate phosphatase. For an enzymatic pathway for an improved process according to the invention, this pathway is combined with the pathway of FIG. 1, 2, or 3.

DETAILED DESCRIPTION

Figure 1:
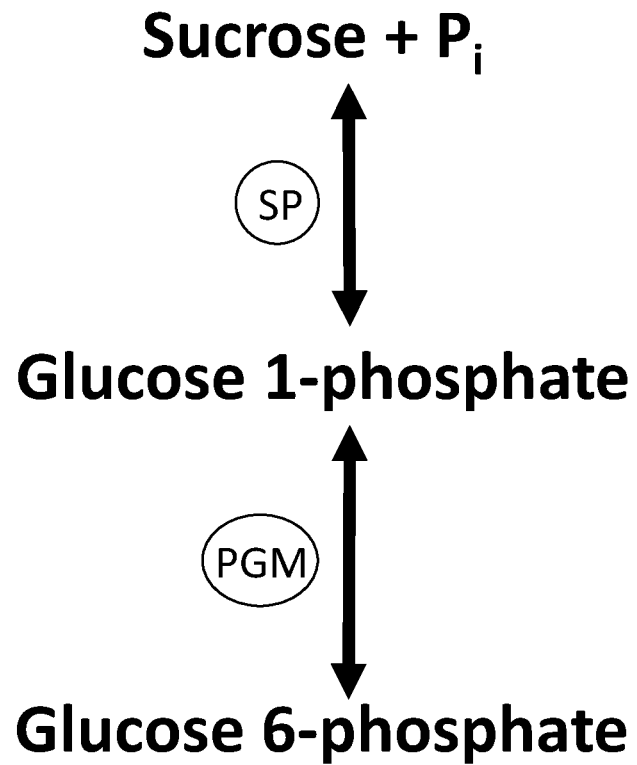
FIG. 1 is a schematic diagram showing an enzymatic pathway converting sucrose to G6P. The following abbreviations are used: SP, sucrose phosphate; and PGM, phosphoglucomutase. The improved processes of the invention contain one or more of the following improvements: SP comprises an amino acid sequence having at least 90% sequence identity with any one of SEQ ID NOs: 19-25, and PGM comprises an amino acid sequence having at least 90% sequence identity with any one of SEQ ID NOs: 2-8.

The inventions described herein provide enzymatic pathways or processes for synthesizing hexoses with a high product yield, while greatly decreasing the product separation costs and hexose production costs. The enzymatic processes described herein generally relate to improved processes for preparing hexose monosaccharides from saccharides by enzymatic conversion. Artificial (non-natural) ATP-free enzymatic pathways are provided to convert saccharides to a hexose using cell-free enzyme cocktails. In contrast to cell-based manufacturing methods, the enzymatic processes of the invention involve cell-free preparation of hexoses, have relatively high reaction rates due to the elimination of the cell membrane, which often slows down the transport of substrate/product into and out of the cell. The processes also have a final product free of nutrient-rich fermentation media/cellular metabolites. The saccharides may be chosen from starch or starch derivatives, cellulose or cellulose derivatives, or sucrose. In improved processes of the invention, the enzymes used for the process steps, as indicated, have improved activities over enzymes previously disclosed for the preparation of hexoses.

In one embodiment, the invention relates to improved processes for converting starch and its derivatives to a hexose using at least one of an αGP, PGM and 4GT with higher activities instead of αGPs, PGMs and 4GT previously disclosed. See International Patent Application Publication WO2018/169957, disclosing Alpha-glucan phosphorylase (αGP) from *Thermotoga maritima* (Uniprot ID G4FEH8); Phosphoglucomutase (PGM) from *Thermococcus kodakaraensis* (Uniprot ID Q68BJ6); and 4-alpha-glucanoltransferase from *Thermococcus litoralis* (Uniprot ID O32462). In some improved processes of the invention for the enzymatic production of a hexose from starch or starch derivative, the improvement includes at least one of: a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; b) a step of converting a starch derivative to G1P, catalyzed by an alpha-glucan phosphorylase (αGP), wherein the αGP comprises an amino acid sequence having at least 90% sequence identity with any one of SEQ ID NOs: 10-13; and a step of transglycosylating a starch derivative, catalyzed by a 4-alpha-glucan transferase (4GT), wherein the 4GT comprises an amino acid sequence having at least 90% sequence identity with any one of SEQ ID NOs: 15-17. In an improved process of the invention, the process includes: a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; b) a step of converting a starch derivative to G1P, catalyzed by an alpha-glucan phosphorylase (αGP), wherein the αGP comprises an amino acid sequence having at least 90% sequence identity with any one of SEQ ID NOs: 10-13; and a step of transglycosylating a starch derivative, catalyzed by a 4-alpha-glucan transferase (4GT), wherein the 4GT comprises an amino acid sequence having at least 90% sequence identity with any one of SEQ ID NOs: 15-17.

In another embodiment, the invention relates to improved processes for converting cellulose and its derivatives to a hexose using a PGM with higher activity instead of PGM from *Thermococcus kodakaraensis* (Uniprot ID Q68BJ6). In some improved processes of the invention for the enzymatic production of a hexose from cellulose or cellulose derivative, the improvement includes a step of converting G1P to glucose 6-phosphate (G6P), catalyzed by a PGM, wherein the PGM comprises an amino acid sequence having at least 90% sequence identity with any one of SEQ ID NOs: 2-8.

In yet another embodiment, the invention relates to improved processes for converting sucrose to a hexose using at least one of a SP with a higher activity instead of the previously disclosed SP from *Thermoanaerobacterium thermosaccharolyticum* (Uniprot ID D9TT09) and a PGM with a higher activity instead of PGM from *Thermococcus kodakaraensis* (Uniprot ID Q68BJ6). In some improved processes of the invention for the enzymatic production of a hexose from sucrose, the improvement includes at least one of a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; and b) a step of converting sucrose to glucose 1-phosphate (G1P) using a sucrose phosphorylase, wherein the sucrose phosphorylase comprises an amino acid sequence having at least 90% sequence identity with any one of SEQ ID NOs: 19-25. In an improved process of the invention, the process includes a) a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8; and b) a step of converting sucrose to glucose 1-phosphate (G1P) using a sucrose phosphorylase, wherein the sucrose phosphorylase comprises an amino acid sequence having at least 90% sequence identity with any one of SEQ ID NOs: 19-25.

In some improved processes of the invention the hexose is selected from allose, mannose, galactose, fructose, altrose, talose, sorbose, gulose idose, allulose, inositol, and tagatose. Some improved processes of the invention further include a step of dephosphorylating the hexose-phosphate using a hexose phosphate phosphatase.

Some improved processes according to the invention for the enzymatic production of a hexose from starch or a starch derivative, cellulose or a cellulose derivative, or sucrose, include a step of converting glucose 1-phosphate (G1P) to glucose 6-phosphate (G6P), catalyzed by a phosphoglucomutase (PGM), wherein the PGM comprises an amino acid sequence having at least 90% sequence identity with any one of SEQ ID NOs: 2-8. Preferably, the PGM comprises the amino acid sequence of any one of SEQ ID NO: 2-8. More preferably, the PGM comprises the amino acid sequence of SEQ ID NO: 8.

Phosphoglucomutase (PGM) (EC 5.4.2.2) catalyzes the interconversion of glucose 1-phosphate and glucose 6-phosphate. In an improved process of the invention for the production of hexoses from a saccharide, the reaction proceeds in the direction of G6P, which is then processed further downstream where the final enzymatic step in the process is an energetically favorable, irreversible step of dephosphorylation of a hexose phosphate.

In improved processes of the invention, the PGM has a higher activity relative to the previously described PGM from *Thermococcus kodakaraensis* (Uniprot ID Q68BJ6), with the amino acid sequence as listed in SEQ ID NO: 1. Preferably, PGMs used in the processes of the invention have an enzymatic activity improved by at least 10%, at least 100%, at least 200%, at least 500%, at least 1000%, at least 2000%, at least 2500%, at least 3000%, at least 3500%, at least 4000%, at least 4500%, at least 5000%, or at least 5500% over the activity of PGM from *Thermococcus kodakaraensis* (Uniprot ID Q68BJ6).

For instance, as shown in Example 1, PGMs for use in processes of the invention have improved activity over PGM from *Thermococcus kodakaraensis* (Uniprot ID Q68BJ6): PGM from *Geobacillus stearothermophilus* NUB3621 (Uniprot ID A0A023CRS6) has enzymatic activity improved by approximately 700%; PGM from *Caldibacillus debilis* (Uniprot ID A0A150LLZ1) has enzymatic activity improved by approximately 1900%; PGM from *Geobacillus thermoglucosidasius* (UniParc ID UPI0001D17AE3) has enzymatic activity improved by approximately 2100%; PGM from *Parageobacillus caldoxylosilyticus* NBRC107762 (Uniprot ID A0A023D195) has enzymatic activity improved by approximately 1980%; PGM from *Thermobrachium celere* DSM 8682 (Uniprot ID R7RR04) has enzymatic activity improved by approximately 5100%; PGM from *Anaerolinea thermophila* (Uniprot ID E8N4Y6) has enzymatic activity improved by approximately 5800%; and PGM from *Thermanaerothrix daxensis* (Uniprot ID A0A0P6YKY9) has enzymatic activity improved by approximately 6500%. The examples below provide protocols to those skilled in the art for determining activity of PGMs as part of an enzymatic process, which involve, for example, incubating the enzyme with its substrate, and then measuring the amounts of reactants and products, or subsequent downstream products, via HPLC. Measurements of relative activities any two enzymes are performed under identical reaction conditions such as buffer, pH, temperature, etc.

Examples of PGMs for use in the improved process of the invention include but are not limited to the following proteins: PGM from *Geobacillus stearothermophilus* NUB3621 (Uniprot ID A0A023CRS6) with the amino acid sequence as listed in SEQ ID NO: 2; PGM from *Caldibacillus debilis* (Uniprot ID A0A150LLZ1) with the amino acid sequence as listed in SEQ ID NO: 3; PGM from *Geobacillus thermoglucosidasius* (UniParc ID UPI0001D17AE3) with the amino acid sequence as listed in SEQ ID NO: 4; PGM from *Parageobacillus caldoxylosilyticus* NBRC107762 (Uniprot ID A0A023D195) with the amino acid sequence as listed in SEQ ID NO: 5; PGM from *Thermobrachium celere* DSM 8682 (Uniprot ID R7RR04) with the amino acid sequence as listed in SEQ ID NO: 6; PGM from *Anaerolinea thermophila* (Uniprot ID E8N4Y6) with the amino acid sequence as listed in SEQ ID NO: 7; and PGM from *Thermanaerothrix daxensis* (Uniprot ID A0A0P6YKY9) with the amino acid sequence as listed in SEQ ID NO: 8, and PGMs comprising an amino acid sequence having at least 90%, at least 95%, at least 97%, at least 99%, or 100% amino acid sequence identity to any one of SEQ ID NOs: 2-8.

PGMs for use in the improved processes of the invention generally are part of the Alpha-D-phosphohexomutase superfamily (IPR005841) and contain four domains that form the active site of the enzyme. The first three domains consist of an αβ core and the forth domain contains a TATA box-binding protein-like fold (Mehra-Chaudhary et al. Proteins 79(4): 1215-29, 2011). The first domain contributes a conserved serine residue for phosphoryl transfer to the active site (Ser147 of SEQ ID NO: 3). The second domain contributes conserved Mg2+ binding residues to the active site (Asp306, Asp308, and Asp310 of SEQ ID NO: 3). The third domain contributes conserved residues for substrate specificity to the active site (Glu406 and Ser408 of SEQ ID NO: 3). The forth domain contributes conserved residues for phosphate binding to the active site (Arg538 of SEQ ID NO: 3). Additionally, a positively charged residue (Lys/Arg) is conserved with a role in catalysis at Lys420 of SEQ ID No: 3. Conserved residues cited from Lee et al. FEBS J 280(11): 2622-32, 2013 and Levin et al. Protein Engineering, Design and Selection 12(9): 737-746, 1999.

Some improved processes of the invention for the production of hexose from starch or a starch derivative according to the invention include the step of converting the starch derivative to G1P catalyzed by αGP, wherein the αGP comprises an amino acid sequence having at least 90% amino acid sequence identity with any one of SEQ ID NOs: 10-13. Preferably, the αGP comprises the amino acid sequence of any one of SEQ ID NOs: 10-13. More preferably, the αGP comprises the amino acid sequence of SEQ ID NO: 11.

Alpha-glucan phosphorylase or starch phosphorylase (αGP) (EC 2.4.1.1) phosphorolytically cleaves maltooligosaccharides to yield G1P. Starch phosphorylase also catalyzes the reverse reaction, that is, the transfer of glucosyl units from G1P to the nonreducing end of alpha-1,4-D-glucan chains with the release of phosphate. Generally, the degree of polymerization of the oligosaccharide chains is 4 or more. In improved process of the invention for the production of hexoses from a starch derivative, the reaction proceeds in the direction of G1P, which is then processed further downstream where the final enzymatic step in the process is an energetically favorable, irreversible step of dephosphorylation of a hexose phosphate.

In the improved processes of the invention, the αGP has a higher activity relative to the previously described alpha-glucan phosphorylase (αGP) from *Thermotoga maritima* (Uniprot ID G4FEH8), with the amino acid sequence as listed in SEQ ID NO: 9. Preferably, αGPs used in the processes of the invention have an enzymatic activity improved by at least 10%, at least 50%, at least 100%, at least 150%, or at least 200%, over the activity of αGP from *Thermotoga maritima* (Uniprot ID G4FEH8). For instance, as shown in Example 2, αGP from *Thermus thermophilus* (Uniprot ID Q5SJ42) has enzymatic activity improved by approximately 71% over αGP from *Thermotoga maritima* (Uniprot ID G4FEH8); αGP from *Thermus* sp. CCB_US3_UF1 (Uniprot ID G8NCC0) has enzymatic activity improved by approximately 186% over αGP from Thermotoga maritima (Uniprot ID G4FEH8); αGP from Thermoanaerobacter pseudethanolicus strain ATCC 33223 (Uniprot ID B0K7V8) has enzymatic activity improved by approximately 128% over αGP from Thermotoga maritima (Uniprot ID G4FEH8); and αGP from Thermanaerovibrio acidaminovorans strain ATCC 49978 (Uniprot ID D1B926) has enzymatic activity improved by approximately 111% over αGP from Thermotoga maritima (Uniprot ID G4FEH8). The examples below provide protocols to those skilled in the art for determining activity of αGPs as part of an enzymatic process, which involve, for example, incubating the enzyme with its substrate, and then measuring the amounts of reactants and products or, subsequent downstream products, via spectrophotometric measurements and HPLC. Measurements of relative activities any two enzymes are performed under identical reaction conditions such as buffer, pH, temperature, etc.

Examples of αGPs for use in the improved process of the invention include but are not limited to the following proteins: αGP from *Thermus thermophilus* (Uniprot ID Q5SJ42), with the amino acid sequence as listed in SEQ ID NO: 10; αGP from *Thermus* sp. CCB_US3_UF1 (Uniprot ID G8NCC0), with the amino acid sequence as listed in SEQ ID NO: 11; αGP from *Thermoanaerobacter pseudethanolicus* strain ATCC 33223 (Uniprot ID B0K7V8), with the amino acid sequence as listed in SEQ ID NO: 12; αGP from *Thermanaerovibrio acidaminovorans* strain ATCC 49978 (Uniprot ID D1B926), with the amino acid sequence as listed in SEQ ID NO: 13; and αGPs having at least 90%, at least 95%, at least 97%, at least 99%, or 100% amino acid sequence identity to SEQ ID NO: 10, SEQ ID NO: 11, SEQ ID NO: 12, or SEQ ID NO: 13.

Alpha-glucan phosphorylases for use in the improved processes of the invention generally are part of the Glycosyl transferase, family 35 (IPR000811) and contain the 'alpha glucan phosphorylase' domain (IPR011834). Some αGP have conserved residues for PLP binding, PLP stabilization, and phosphate binding. For example, in Uniprot ID D1B926 (SEQ ID NO: 13) Lys585 is conserved for PLP binding; Arg484 and Thr581 are conserved for PLP stabilization; and Gly110, Arg485, and Lys490 are conserved for phosphate binding (conserved residues cited from Watson et al. The EMBO Journal Vol. 16 No. 1 pp. 1-14, 1997).

In some improved process according to the invention for the production of a hexose from a starch derivative, the improvement includes a step of transglycosylating the starch derivative using a 4-alpha-glucan transferase (4GT), wherein the 4GT comprises an amino acid sequence having at least 90% sequence identity with any one of SEQ ID Nos: 15-17. Preferably, the 4GT comprises the amino acid sequence of any one of SEQ ID NOs: 15-17. More preferably, the αGP comprises the amino acid sequence of SEQ ID NO: 17.

4-alpha-glucan transferase (4GT) (EC 2.4.1.25) catalyzes the transglycosylation of maltooligosaccharides, yielding maltooligosaccharides of various lengths and glucose. Maltose and glucose can be used as acceptors in the transfer reaction.

Some processes of the invention for producing a hexose include an energetically favorable dephosphorylation step converting the hexose phosphate to the hexose. In such processes, especially when conducted in a single reaction vessel, the phosphate is recycled and used upstream in the process, for example, in the reaction catalyzed by αGP converting amylodextrin to G1P. However, αGP does not react with high activity toward amylodextrins with degrees of polymerization (DP) less than 4. In such processes according to the invention, 4GT is added to the reaction to improve the overall yield. 4GT transglycosylates amylodextrin such that DPs smaller than 4, e.g., maltotriose, are converted into longer chain amylodextrins that can be degraded by αGP. Without 4GT, maltotriose would build up as an end product of the process rather than being recycled back into longer chain amylodextrins that can participate in the process again to enhance yields. 4GT increases yields when amylodextrin is sufficiently degraded by αGP to produce significant amounts of maltotriose. This occurs due to the energetically favorable dephosphorylation step and phosphate recycling.

In the improved processes of the invention, the 4GT has a higher activity relative to the previously described 4-alpha-glucan transferase (4GT) from *Thermococcus litoralis* (Uniprot ID O32462), with the amino acid sequence as recited in SEQ ID NO:14. Preferably, 4GT used in the processes of the invention have an enzymatic activity improved by at least 10%, at least 50%, at least 100%, at least 150%, or at least 200%, over the activity of 4GT from *Thermococcus litoralis* (Uniprot ID O32462). For instance, as shown in Example 3, 4GT from *Oceanithermus profundus* DSM 14977 (Uniprot ID E4U8S9) has enzymatic activity improved by approximately 128% over 4GT from *Thermococcus litoralis* (Uniprot ID O32462); 4GT from *Meiothermus silvanus* strain ATCC 700542 (Uniprot ID D7BF07) has enzymatic activity improved by approximately 212% over 4GT from *Thermococcus litoralis* (Uniprot ID O32462); and 4GT from *Anaerolinea thermophila* strain DSM 14523 (Uniprot ID E8MXP8) has enzymatic activity improved by approximately 184% over 4GT from *Thermococcus litoralis* (Uniprot ID O32462). The examples below provide protocols to those skilled in the art for determining activity of 4GTs as part of an enzymatic process, which involve, for example, incubating the enzyme with its substrate, and then measuring the amounts of glucose via spectrophotometric measurements. Measurements of relative activities any two enzymes are performed under identical reaction conditions such as buffer, pH, temperature, etc.

Examples of 4GTs for use in the improved process of the invention include but are not limited to the following proteins: 4GT from *Oceanithermus profundus* DSM 14977 (Uniprot ID E4U8S9), with the amino acid sequence as listed in SEQ ID NO: 15; 4GT from *Meiothermus silvanus* strain ATCC 700542 (Uniprot ID D7BF07), with the amino acid sequence as listed in SEQ ID NO: 16; 4GT from *Anaerolinea thermophila* strain DSM 14523 (Uniprot ID E8MXP8), with the amino acid sequence as listed in SEQ ID NO: 17; and 4GTs having at least 90%, at least 95%, at least 97%, at least 99%, or 100% amino acid sequence identity to SEQ ID NO: 15, SEQ ID NO: 16, or SEQ ID NO: 17.

4-glucan transferases for use in the improved processes of the invention generally are part of the glycoside transferase superfamily (IPR017853), more specifically the glycoside hydrolase, family 77 (IPR003385). Generally, 4-glucan transferases contain an $(\beta/\alpha)_8$-barrel catalytic domain where the active site is at the c-terminal end of the barrel β-strands. The active site contains a conserved catalytic tryad. In SEQ ID NO:17, these conserved residues correspond with Asp298 (nucleophile), Glu345 (proton donor), and Asp398 (transition state stabilizer). 4GTs for use in the improved processes of the invention also contain conserved residues associated with substrate binding. For example, in SEQ ID NO: 17, these conserved residues correspond with Tyr60, Asp218, Arg296, and His397. See Przylas et al. Journal of Molecular Biology 296(3): 873-886, 2000.

In some improved processes for the enzymatic production of a hexose from sucrose, the improvement includes a step of converting sucrose to glucose 1-phosphate (G1P) catalyzed by a sucrose phosphorylase, wherein the sucrose phosphorylase comprises an amino acid sequence having at least 90% sequence identity with any one of SEQ ID NOs: 19-25. Preferably, the SP comprises the amino acid sequence of any one of SEQ ID NOs: 19-25. More preferably, the SP comprises the amino acid sequence of SEQ ID NO: 21.

Sucrose phosphorylase, (EC:2.4.1.7), catalyzes the conversion of sucrose and inorganic phosphate to fructose and G1P. In improved process of the invention for the production of hexoses from sucrose, the reaction proceeds in the direction of G1P, which is then processed further downstream where the final enzymatic step in the process is an energetically favorable, irreversible step of dephosphorylation of a hexose phosphate.

In the improved processes of the invention, the SP has a higher activity relative to the previously described SP from *Thermoanaerobacterium thermosaccharolyticum* (Uniprot ID D9TT09), with the amino acid sequence as listed in SEQ ID NO: 18. Preferably, SPs used in the processes of the invention have an enzymatic activity improved by at least 10%, at least 20%, at least 30%, at least 40%, at least 50%, at least 100% or at least 200%, over the activity of SP from *Thermoanaerobacterium thermosaccharolyticum* (Uniprot ID D9TT09). In some embodiments, SPs used in the processes of the invention show an improved maximum yield of hexose, in particular fructose. For instance, several SP with higher activities are shown in Example 4. SP from *Thermoanaerobacterium* sp. PSU-2 (Uniprot ID A0A1X2FWC2) has an enzymatic activity improved by 11% over the activity of of SP from *Thermoanaerobacterium thermosaccharolyticum* (Uniprot ID D9TT09), and a maximum yield of fructose that is 9% higher. SP from *Thermoanaerobacterium thermosaccharolyticum* (Uniprot ID L0IL15) has an enzymatic activity improved by 50% over the activity of SP from *Thermoanaerobacterium thermosaccharolyticum* (Uniprot ID D9TT09), and a maximum yield of fructose that is 1% higher. SP from *Thermoanaerobacterium xylanolyticum* (Uniprot ID F6BJS0) has an enzymatic activity improved by 49% over the activity of SP from *Thermoanaerobacterium thermosaccharolyticum* (Uniprot ID D9TT09), and a maximum yield of fructose that is 32% higher. SP from *Thermobacillus* sp. ZCTH02-B1 (Uniprot ID A0A1Y3Q6Q6) has an enzymatic activity improved by 50% over the activity of SP from *Thermoanaerobacterium thermosaccharolyticum* (Uniprot ID D9TT09), and a maximum yield of fructose that is 3% higher. SP from *Bifidobacterium adolescentis* (Uniprot ID Q84HQ2) has an enzymatic activity improved by 31% over the activity of SP from *Thermoanaerobacterium thermosaccharolyticum* (Uniprot ID D9TT09), and a maximum yield of fructose that is 37% higher. SP from *Paenibacillus thermophilus* (Uniprot ID A0A388NK91) has an enzymatic activity improved by 22% over the activity of SP from *Thermoanaerobacterium thermosaccharolyticum* (Uniprot ID D9TT09), and a maximum yield of fructose that is 19% higher. SP from *Tepidibacillus decaturensis* (Uniprot ID A0A135L6L9) has an enzymatic activity improved by 44% over the activity of SP from *Thermoanaerobacterium thermosaccharolyticum* (Uniprot ID D9TT09), and a maximum yield of fructose that is 9% higher. The increase in maximum yield is significant in a commercial process and comments on the maximum achievable yield of fructose by each SP. Presumably, contributing factors include product inhibition of sucrose phosphorylase by fructose, the rate of the reverse reaction (G1P+fructose⇔sucrose+P$_i$), and more broadly the equilibrium between the formation of fructose and the degradation of fructose at late stages of the reaction.

The examples below provide protocols to those skilled in the art for determining activity of SPs as part of an enzymatic process, which involve, for example, incubating the enzyme with its substrate, and then measuring the amounts of reactants and products, or subsequent downstream products, via HPLC. Measurements of relative activities any two enzymes are performed under identical reaction conditions such as buffer, pH, temperature, etc.

Examples of SPs for use in the improved process of the invention include but are not limited to the following proteins: SP from *Thermoanaerobacterium* sp. PSU-2 (Uniprot ID A0A1X2FWC2), with the amino acid sequence as listed in SEQ ID NO: 19; SP from *Thermoanaerobacterium thermosaccharolyticum* (Uniprot ID L0I1L15), with the amino acid sequence as listed in SEQ ID NO: 20; SP from *Thermoanaerobacterium xylanolyticum* (Uniprot ID F6BJS0), with the amino acid sequence as listed in SEQ ID NO: 21; SP from *Thermobacillus* sp. ZCTH02-B1 (Uniprot ID A0A1Y3Q6Q6), with the amino acid sequence as listed in SEQ ID NO: 22; SP from *Bifidobacterium adolescentis* (Uniprot ID Q84HQ2), with the amino acid sequence as listed in SEQ ID NO: 23; SP from *Paenibacillus thermophilus* (Uniprot ID A0A388NK91), with the amino acid sequence as listed in SEQ ID NO: 24; SP from *Tepidibacillus decaturensis* (Uniprot ID A0A135L6L9), with the amino acid sequence as listed in SEQ ID NO: 25; and SPs having at least 90%, at least 95%, at least 97%, at least 99%, or 100% amino acid sequence identity to any one of SEQ ID Nos:19-25.

SPs for use in the improved processes of the invention generally are part of the Glycoside hydrolase superfamily (IPR017853), more specifically the sucrose phosphorylase family (IPR022527), and contain the Glycosyl hydrolase, family 13, catalytic domain (IPR006047). The glycosyl hydrolase domain consists of a $(\beta/\alpha)_8$-barrel and is the catalystic domain. In total sucrose phosphorylases consist of four domains, the N-terminal domain, the glycosyl hydrolyase domain, the B domain (formed from a large loop in the glycosyl domain), and the C-terminal domain (Sprogøe D, van den Broek L A, Mirza O, Kastrup J S, Voragen A G, Gajhede M, Skov L K (February 2004). "Crystal structure of sucrose phosphorylase from *Bifidobacterium adolescentis*". Biochemistry. 43 (5): 1156-62. doi:10.1021/bi0356395. PMID 14756551). Through sequence alignments to the well studied sucrose phosphorylase from *Leuconostoc mesenteroides* (Uniprot Q59495), conservation of the catalytic residues Asp196 (Schwarz A, Nidetzky B (July 2006). "Asp-196-→Ala mutant of *Leuconostoc mesenteroides* sucrose phosphorylase exhibits altered stereochemical course and kinetic mechanism of glucosyl transfer to and from phosphate". FEBS Letters. 580 (16): 3905-10. doi: 10.1016/j.febslet.2006.06.020. PMID 16797542.), Glu237 (Schwarz A, Brecker L, Nidetzky B (May 2007). "Acid-base catalysis in *Leuconostoc mesenteroides* sucrose phosphorylase probed by site-directed mutagenesis and detailed kinetic comparison of wild-type and Glu237-→Gln mutant enzymes". The Biochemical Journal. 403 (3): 441-9. doi: 10.1042/BJ20070042. PMC 1876375. PMID 17233628), and Asp 295 (Mueller M, Nidetzky B (April 2007). "The role of Asp-295 in the catalytic mechanism of *Leuconostoc mesenteroides* sucrose phosphorylase probed with site-directed mutagenesis". FEBS Letters. 581 (7): 1403-8. doi: 10.1016/j.febslet.2007.02.060. PMID 17350620.) is seen.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. The derivatives of starch can be prepared by enzymatic hydrolysis of starch or by acid hydrolysis of starch. Specifically, the enzymatic hydrolysis of starch can be catalyzed or enhanced by isoamylase (IA, EC. 3.2.1.68), which hydrolyzes α-1,6-glucosidic bonds; pullulanase (PA, EC. 3.2.1.41), which hydrolyzes α-1,6-glucosidic bonds; or alpha-amylase (EC 3.2.1.1), which cleaves α-1,4-glucosidic bonds. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to a hexose and enhanced solubility.

Cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose. Examples of cellulose derivatives include pretreated biomass, regenerated amorphous cellulose, cellodextrin, cellobiose, fructose, and glucose. Furthermore, derivatives of cellulose can be prepared by enzymatic hydrolysis of cellulose catalyzed by cellulase mixtures, by acids, or by pretreatment of biomass. In some processes of the invention G1P is generated from cellulose by cellulose phosphorylase. In some processes, G1P is generated from cellodextrin and cellobiose and free phosphate catalyzed by cellodextrin phosphorylase (CDP) and cellobiose phosphorylase (CBP).

In some improved processes of the invention the hexose is selected from allose, mannose, galactose, fructose, altrose, talose, sorbose, gulose idose, allulose, inositol, and tagatose. Hexoses are monosaccharides with six carbon atoms. Hexoses can be classified by functional group, with aldohexoses having an aldehyde at position 1, and ketohexoses having that ketone at position 2. Aldohexoses (or aldoses) include allose, altrose, glucose, gulose, galactose, idose, talose, and mannose. Ketohexoses (or ketoses) include psicose (allulose), fructose, tagatose, and sorbose. Inositol has no aldehyde nor ketose group and is characterized as a carbocyclic hexose. Improved processes of the invention can be used to convert starch and its derivatives to hexoses selected from allose, mannose, galactose, fructose, altrose, talose, sorbose, gulose, tagatose, allulose, inositol and idose. Hence several of the embodiments of the invention relate to improved processes for the production these individual hexoses.

In an improved process of the invention for the production of a hexose, an additional step of dephosphorylating a hexose phosphate using a hexose phosphate phosphatase is included. In some improved processes of the invention for the production of hexoses, the process steps are conducted in a single reaction vessel. In other improved processes of the invention, the process steps are conducted in more than one single reaction vessels. In some improved process, the process steps are conducted ATP-free, NAD(P)(H)-free, at a phosphate concentration from about 0.1 mM to about 150 mM, the phosphate is recycled, and/or the step of dephosphorylation of the hexose phosphate involves an energetically favorable chemical reaction. In some improved processes of the invention, the process steps are conducted under at least one of the following process conditions: at a temperature ranging from about 37° C. to about 85° C., at a pH ranging from about 5.0 to about 8.0, or for about 0.5 hours to about 48 hours. In some improved process of the invention, the process steps are conducted as a continuous reaction.

Figure 4:
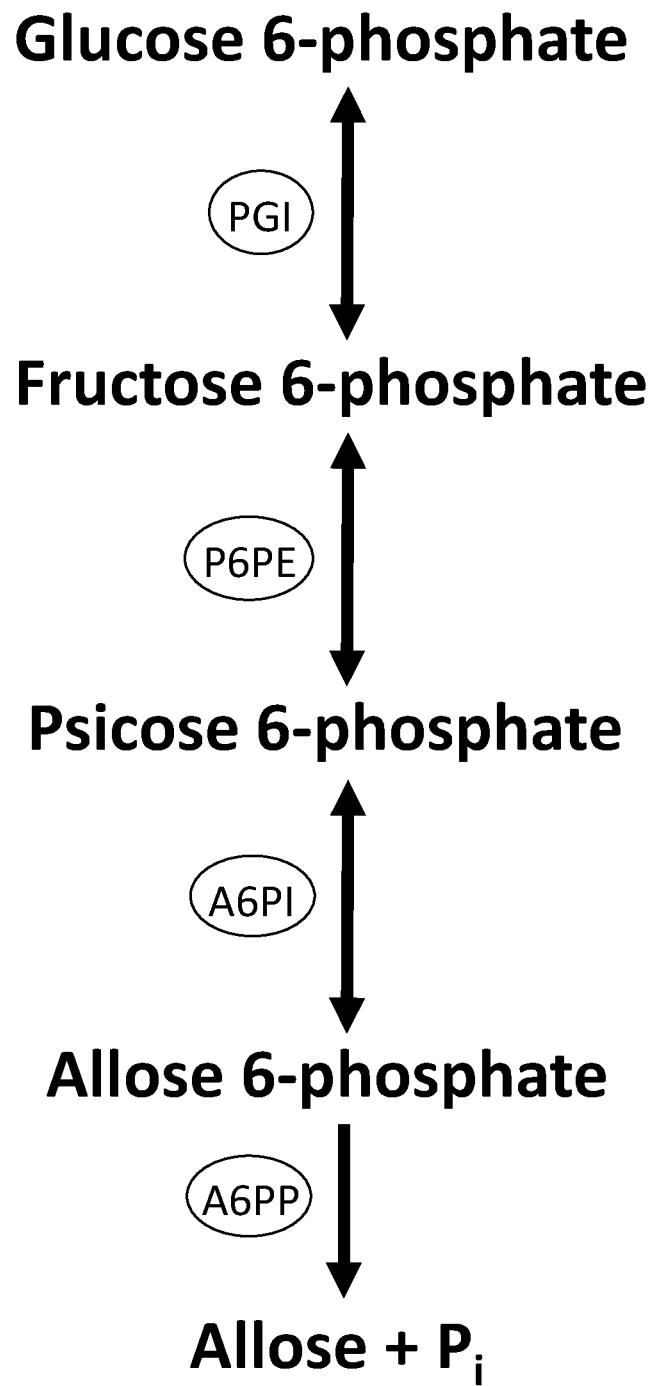
FIG. 4 is a schematic diagram showing an enzymatic pathway converting G6P to allose. The following abbreviations are used: PGI, phosphoglucoisomerase; P6PE, psicose 6-phosphate 3-epimerase; A6PI, allose 6-phosphate isomerase; A6PP, allose 6-phosphate phosphatase. For an enzymatic pathway for an improved process according to the invention, this pathway is combined with the pathway of FIG. 1, 2, or 3.
Figure 5:
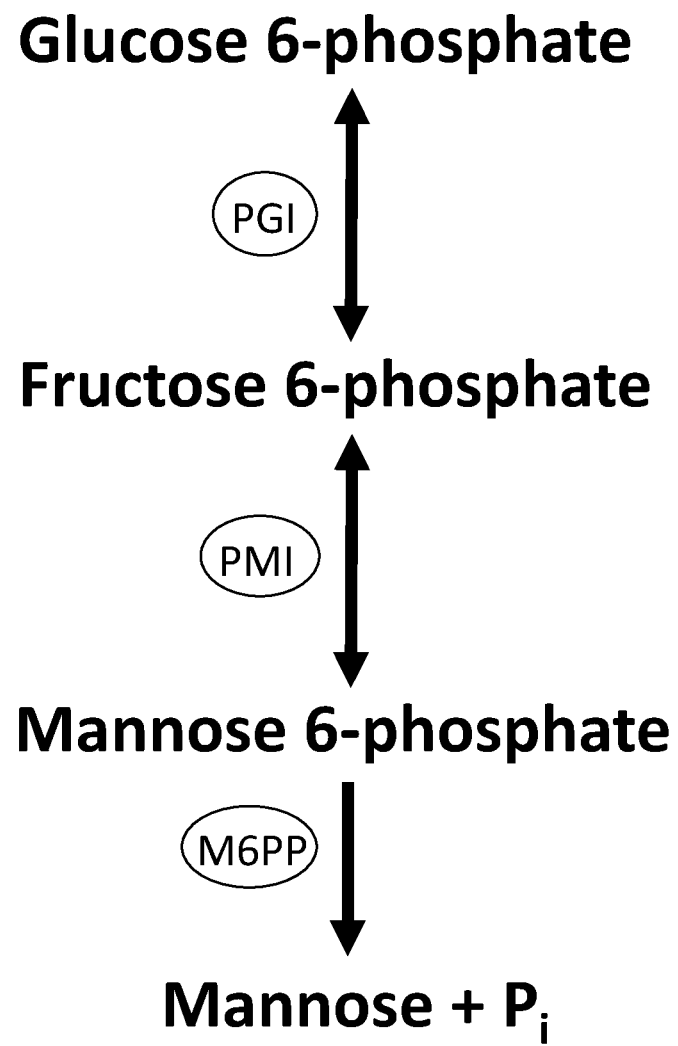
FIG. 5 is a schematic diagram showing an enzymatic pathway converting G6P to mannose. The following abbreviations are used: PGI, phosphoglucoisomerase; PMI, phosphomannose isomerase; and M6PP, mannose 6-phosphate phosphatase. For an enzymatic pathway for an improved process according to the invention, this pathway is combined with the pathway of FIG. 1, 2, or 3.
Figure 6:
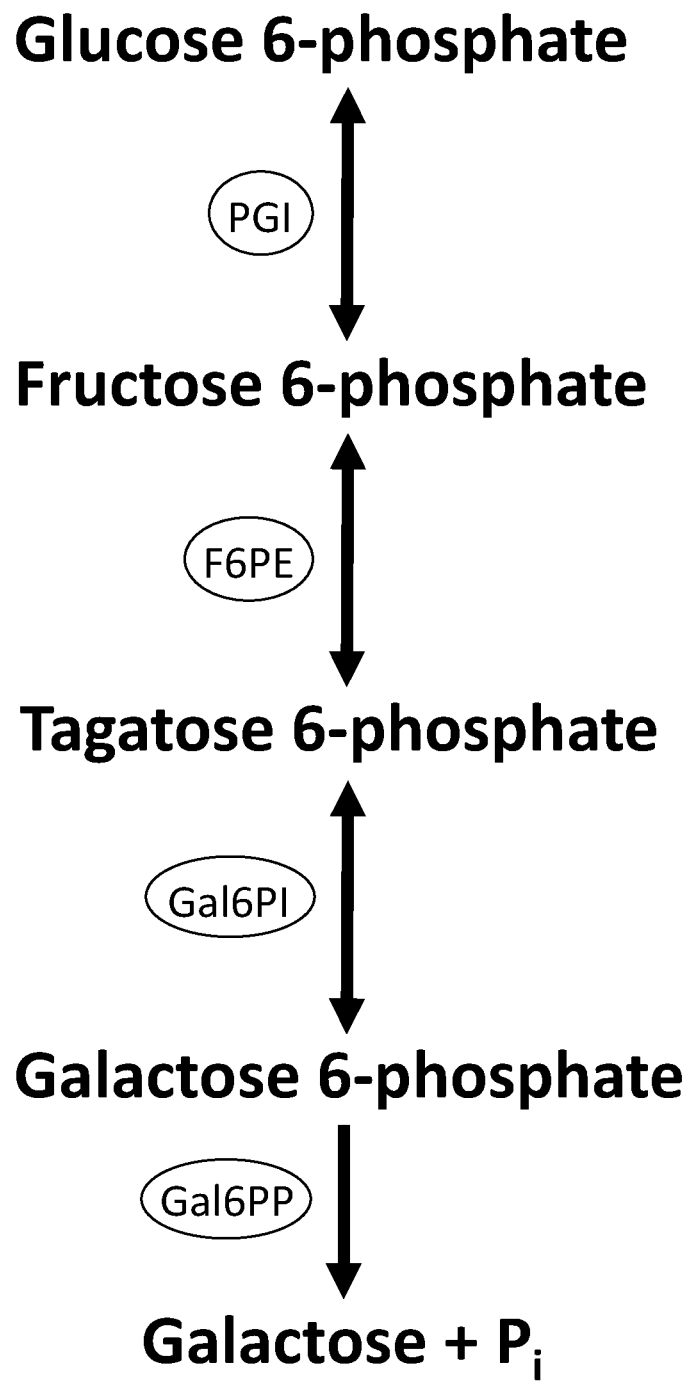
FIG. 6 is a schematic diagram showing an enzymatic pathway converting G6P to galactose. The following abbreviations are used: PGI, phosphoglucoisomerase; F6PE, fructose 6-phosphate isomerase; Gal6PI, galactose 6-phosphate isomerase; Gal6PP, galactose 6-phosphate phosphatase. For an enzymatic pathway for an improved process according to the invention, this pathway is combined with the pathway of FIG. 1, 2, or 3.
Figure 7:
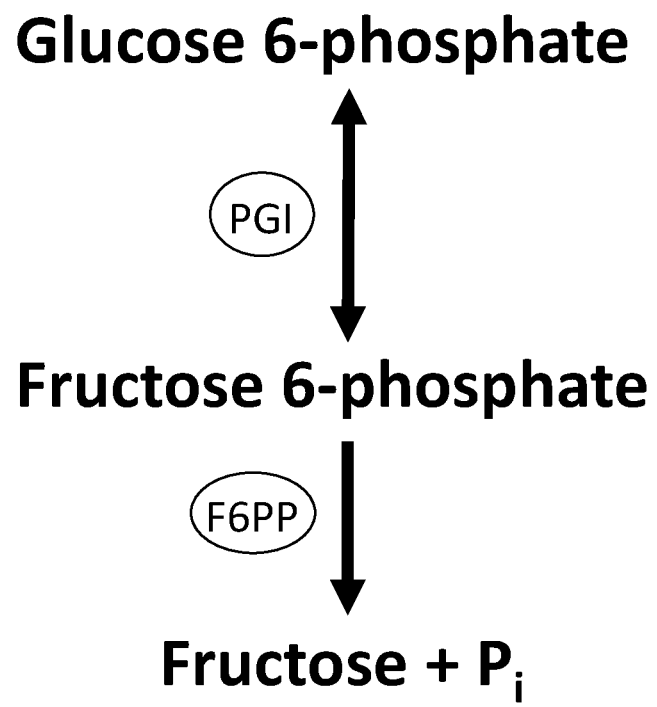
FIG. 7 is a schematic diagram showing an enzymatic pathway converting G6P to fructose. The following abbreviations are used: PGI, phosphoglucoisomerase; F6PP, fructose 6-phosphate phosphatase. For an enzymatic pathway for an improved process according to the invention, this pathway is combined with the pathway of FIG. 1, 2, or 3.
Figure 8:
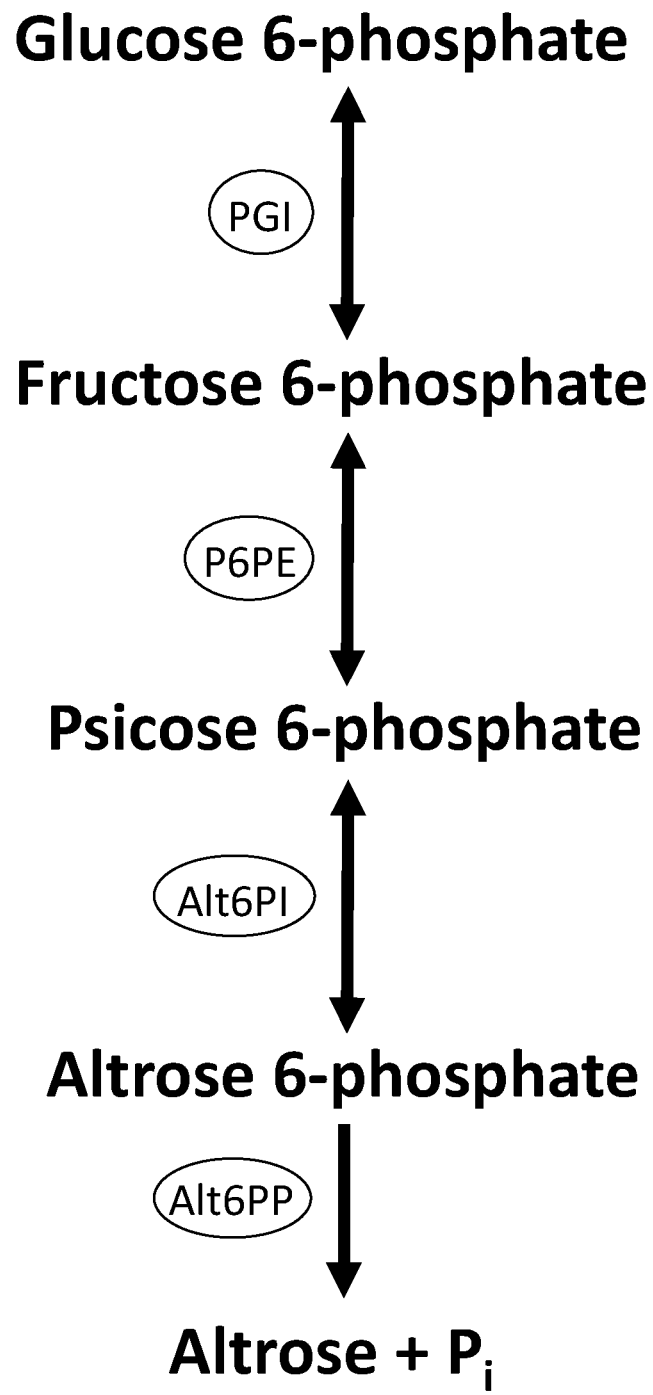
FIG. 8 is a schematic diagram showing an enzymatic pathway converting G6P to altrose. The following abbreviations are used: PGI, phosphoglucoisomerase; P6PE, psicose 6-phosphate epimerase; Alt6PI, altrose 6-phosphate isomerase; Alt6PP, altrose 6-phosphate phosphatase. For an enzymatic pathway for an improved process according to the invention, this pathway is combined with the pathway of FIG. 1, 2, or 3.
Figure 9:
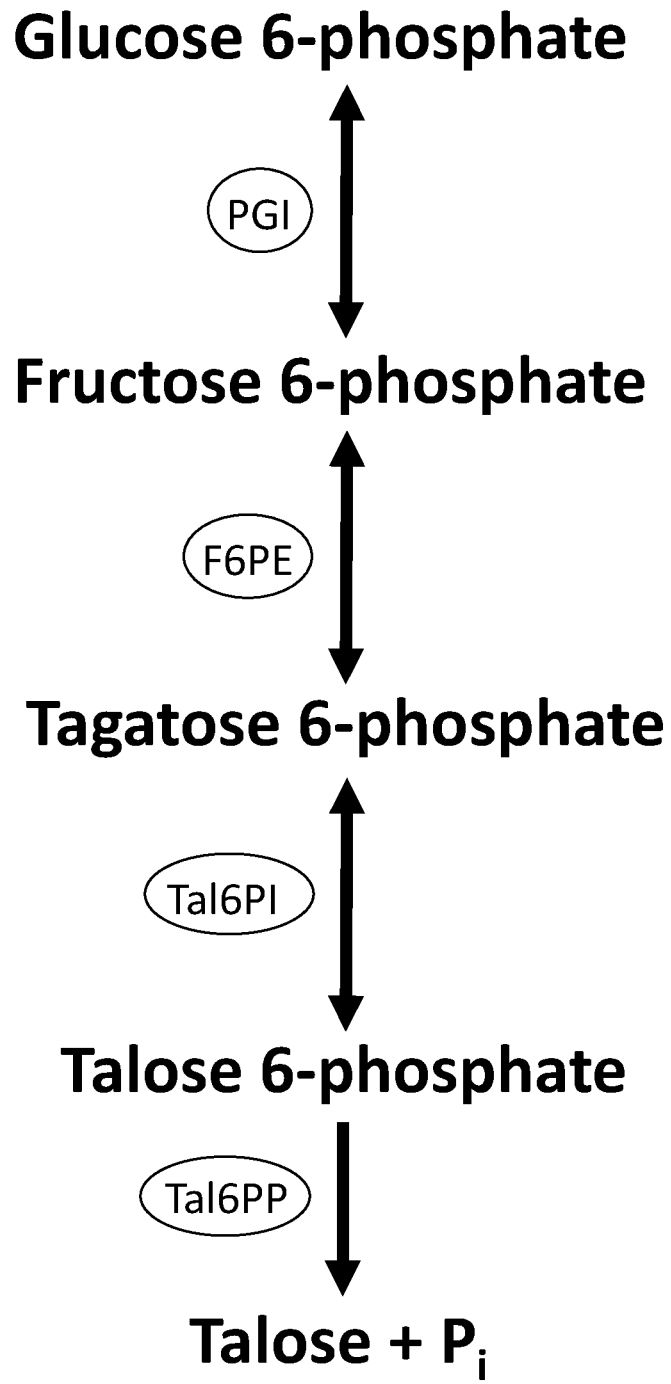
FIG. 9 is a schematic diagram showing an enzymatic pathway converting G6P to talose. The following abbreviations are used: PGI, phosphoglucoisomerase; F6PE, fructose 6-phosphate epimerase; Tal6PI, talose 6-phosphate isomerase; Tal6PP, talose 6-phosphate phosphatase. For an enzymatic pathway for an improved process according to the invention, this pathway is combined with the pathway of FIG. 1, 2, or 3.
Figure 10:
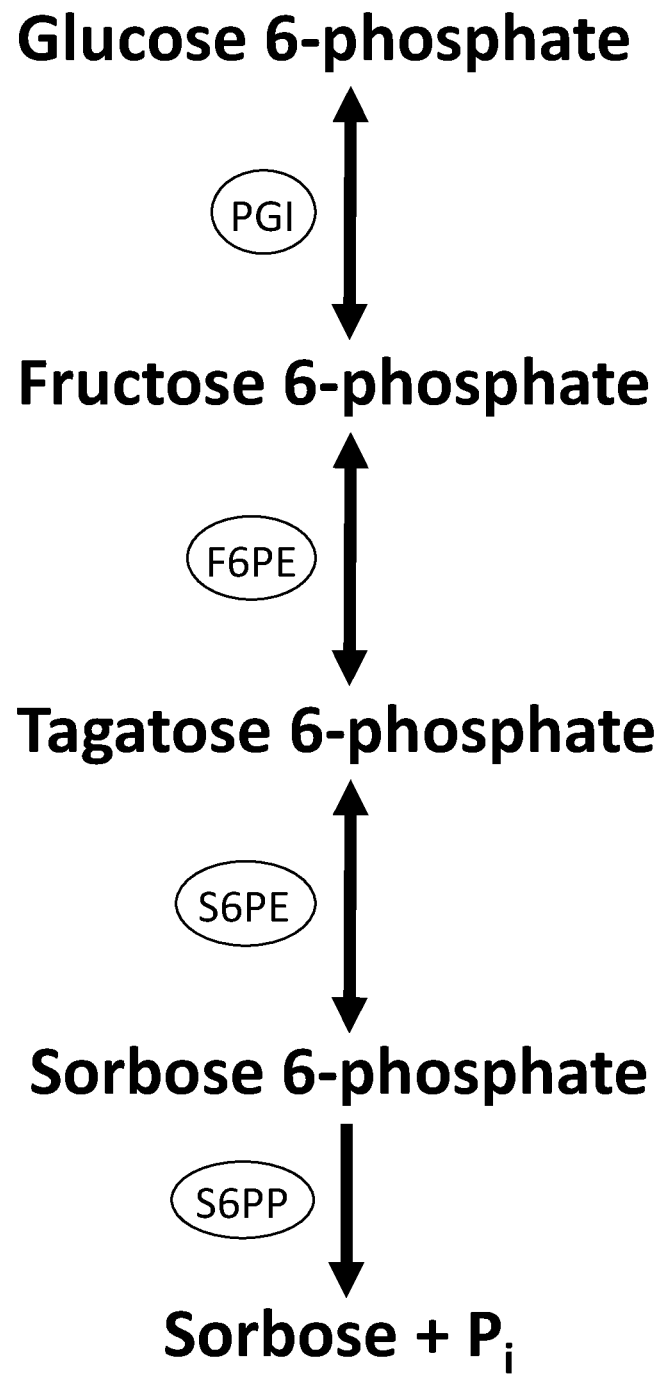
FIG. 10 is a schematic diagram showing an enzymatic pathway converting G6P to sorbose. The following abbreviations are used: PGI, phosphoglucoisomerase; F6PE, fructose 6-phosphate epimerase; S6PE, sorbose 6-phosphate epimerase; S6PP, sorbose 6-phosphate phosphatase. For an enzymatic pathway for an improved process according to the invention, this pathway is combined with the pathway of FIG. 1, 2, or 3.
Figure 11:
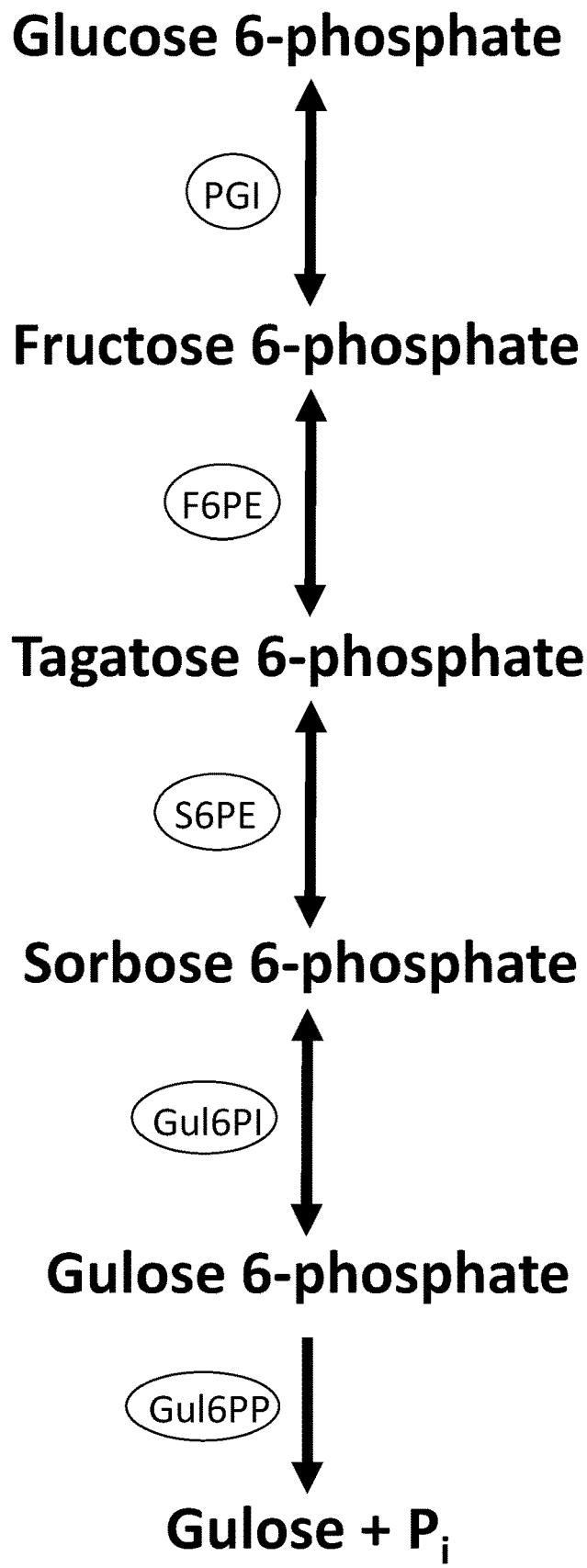
FIG. 11 is a schematic diagram showing an enzymatic pathway converting G6P to gulose. The following abbreviations are used: PGI, phosphoglucoisomerase; F6PE, fructose 6-phosphate epimerase; S6PE, sorbose 6-phosphate epimerase; Gul6PI, gulose 6-phosphate isomerase; Gul6PP, gulose 6-phosphate phosphatase. For an enzymatic pathway for an improved process according to the invention, this pathway is combined with the pathway of FIG. 1, 2, or 3.
Figure 13:
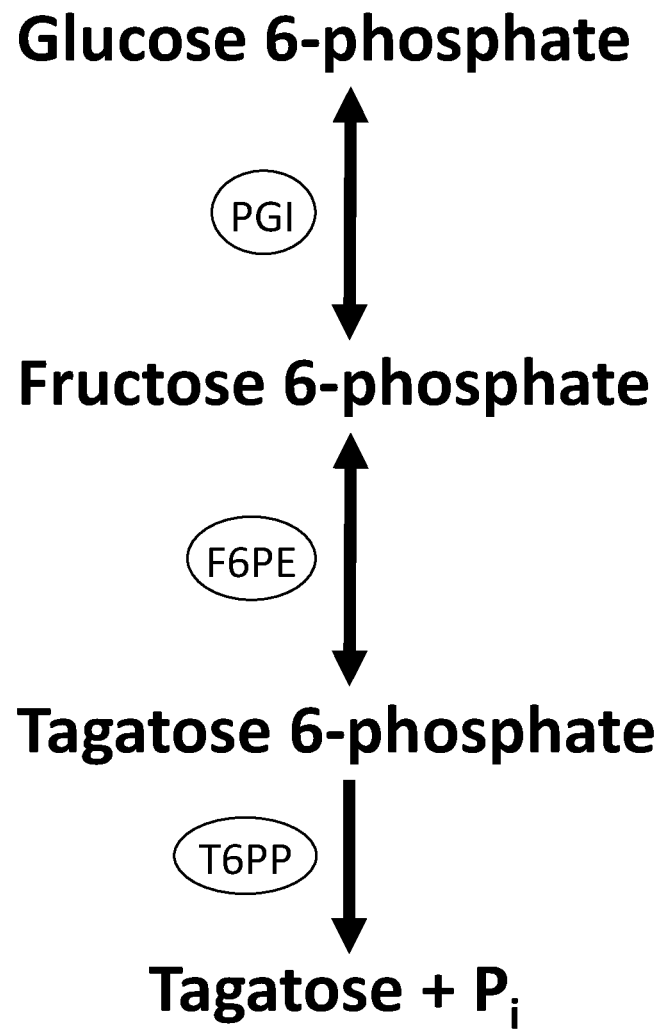
FIG. 13 is a schematic diagram showing an enzymatic pathway converting G6P to tagatose. The following abbreviations are used: PGI, phosphoglucoisomerase; F6PE, fructose 6-phosphate epimerase; T6PP, tagatose 6-phosphate phosphatase. For an enzymatic pathway for an improved process according to the invention, this pathway is combined with the pathway of FIG. 1, 2, or 3.
Figure 14:
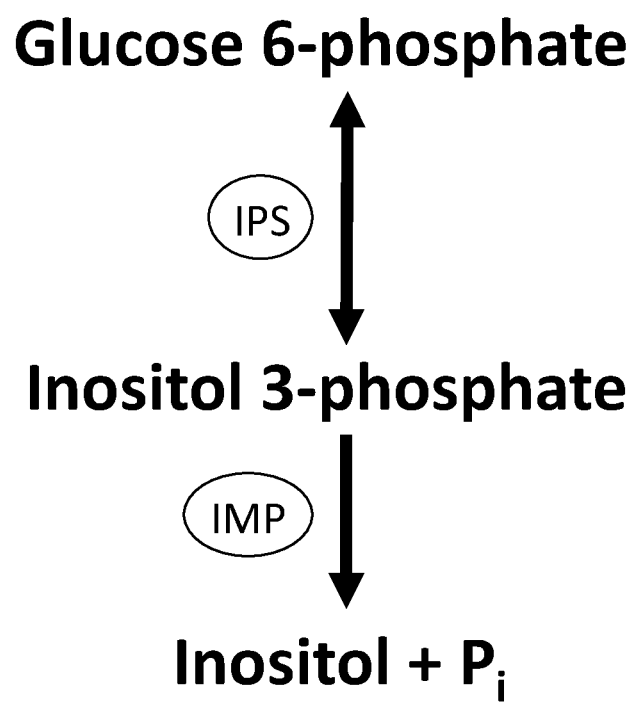
FIG. 14 a schematic diagram showing an enzymatic pathway converting G6P to inositol. The following abbreviations are used: IPS, inositol-phosphate synthase; IMP, inositol monophosphatase. For an enzymatic pathway for an improved process according to the invention, this pathway is combined with the pathway of FIG. 1, 2, or 3.
Figure 15:
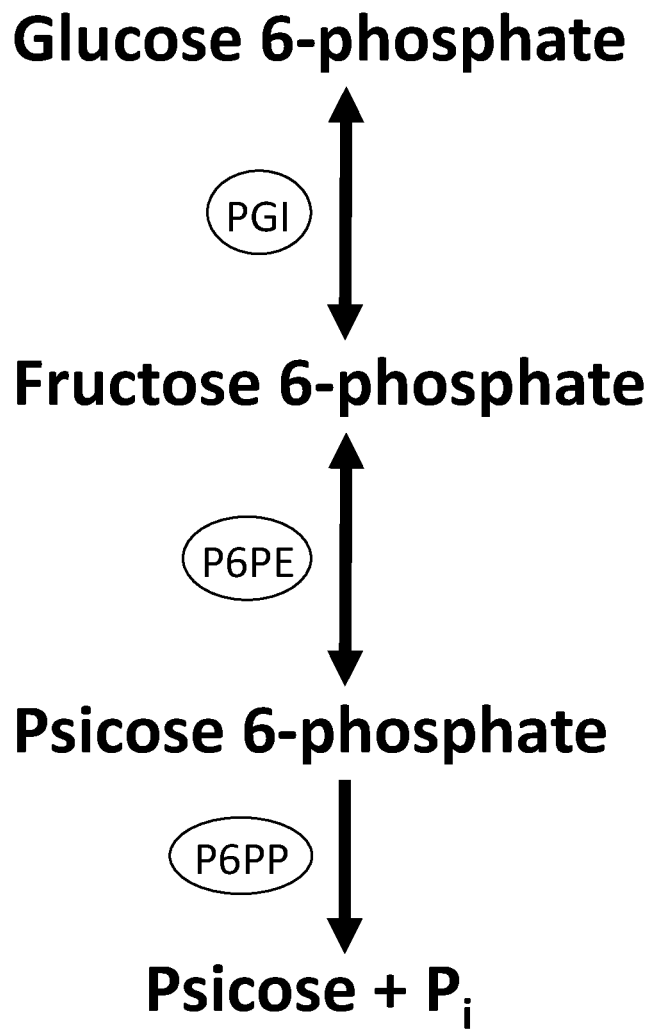
FIG. 15 is a schematic diagram illustrating an enzymatic pathway converting G6P to psicose (allulose). The following abbreviations are used: PGI, phosphoglucoisomerase; P6PE, psicose 6-phosphate epimerase; P6PP, psicose 6-phosphate phosphatase. For an enzymatic pathway for an improved process according to the invention, this pathway is combined with the pathway of FIG. 1, 2, or 3.
Figure 16:
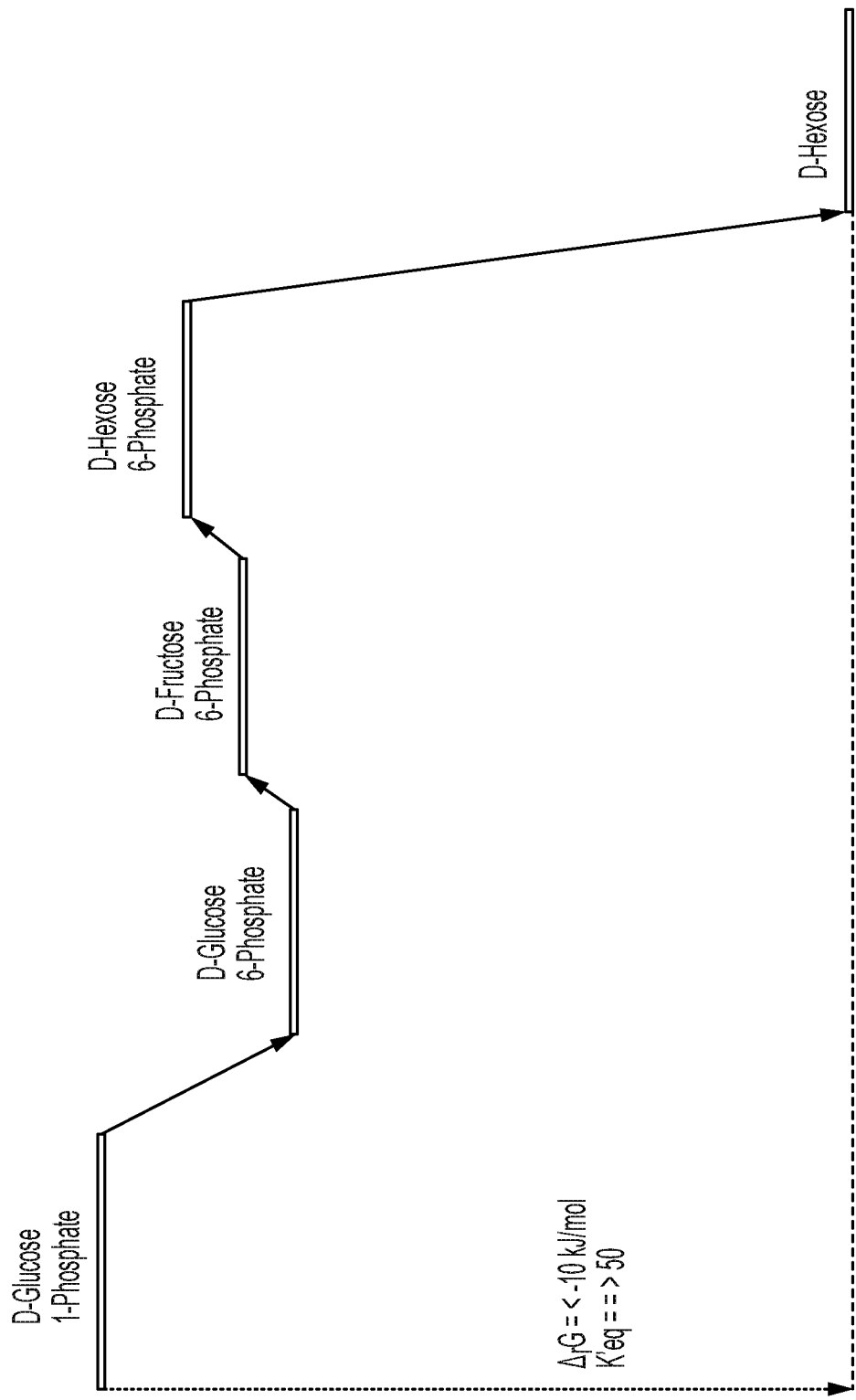
FIG. 16 shows the Reaction Gibbs Energy between intermediates based on formation Gibbs energy for the conversion of glucose 1-phosphate to another hexose.

In some processes of the invention for the preparation of a hexose, an additional step of dephosphorylating a hexose phosphate using a hexose phosphate phosphatase is included. The phosphatase used in the processes of the invention is specific for the hexose phosphate. For example, allose 6-phosphate is converted to allose by allose 6-phosphate phosphatase; mannose 6-phosphate is converted to mannose by mannose 6-phosphate phosphatase; galactose 6-phosphate is converted to galactose by galactose 6-phosphate phosphatase; fructose 6-phosphate is converted to fructose by fructose 6-phosphate phosphatase; altrose 6-phosphate is converted to altrose by altrose 6-phosphate phosphatase; talose 6-phosphate is converted to talose by talose 6-phosphate phosphatase; sorbose 6-phosphate is converted to sorbose by sorbose 6-phosphate phosphatase; gulose 6-phosphate is converted to gulose by gulose 6-phosphate phosphatase; tagatose 6-phosphate is converted to tagatose by tagatose 6-phosphate phosphatase; psicose 6-phosphate is converted to psicose by psicose 6-phosphate phosphatase; inositol 3-phosphate is converted to inositol by inositol monophosphatase; and idose 6-phosphate is converted to idose by idose 6-phosphate phosphatase. As used herein, specific means having a higher specific activity for the indicated hexose over other hexoses. For instance, allose 6-phosphate phosphatase has a higher specific activity on allose 6-phosphate than, for example, sorbose 6-phosphate or talose 6-phosphate. In processes of the invention, the hexose-phosphate phosphatase has a higher activity for the indicated hexose phosphate compared to other hexose phosphate intermediates in the process. As an illustrative example, in a process for converting maltodextrin to allose, the allose 6-phosphate phosphatase has a higher activity for allose 6-phosphate compared to the other hexose phosphate intermediates in the process, such as G1P, G6P, F6P, and psicose 6-phosphate. See FIG. 2 and FIG. 4.

Sugar alcohols can be made from the various hexose sugars produced by the improved processes of the invention. For example, mannitol and sorbitol could be made and are currently of commercial interest to the medical and food industries. The ketose or aldose product of these improved enzymatic processes can be reduced to the sugar alcohol form using a reducing agent such as hydrogen gas or sodium borohydride. Preferably, hydrogen gas would be used as the reducing agent as previously described in U.S. Pat. No. 6,570,043 B2; 8,816,068 B2; or 5,466,795 A.

In one embodiment, the improved process of the invention is directed to the production of allose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to psicose 6-phosphate (P6P) catalyzed by psicose 6-phosphate 3-epimerase (P6PE); converting the P6P to allose 6-phosphate (A6P) catalyzed by allose 6-phosphate isomerase (A6PI); and converting the A6P to allose catalyzed by allose 6-phosphate phosphatase (A6PP).

In one embodiment, the improved process of the invention is directed to the production of mannose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to mannose 6-phosphate (M6P) catalyzed by mannose 6-phosphate isomerase (M6PI) or phosphoglucose/phosphomannose isomerase (PGPMI); and converting the M6P to mannose catalyzed by mannose 6-phosphate phosphatase (M6PP).

In one embodiment, the improved process of the invention is directed to the production of galactose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to tagatose 6-phosphate (T6P) catalyzed by fructose 6-phosphate 4-epimerase (F6PE); converting the T6P to galactose 6-phosphate (Gal6P) catalyzed by galactose 6-phosphate isomerase (Gal6PI); and converting the Gal6P to galactose catalyzed by galactose 6-phosphate phosphatase (Gal6PP).

In one embodiment, the improved process of the invention is directed to the production of fructose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); and converting the F6P to fructose catalyzed by fructose 6-phosphate phosphatase (F6PP).

In one embodiment, the improved process of the invention is directed to the production of altrose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to converting the F6P to P6P catalyzed by P6PE; converting the P6P to altrose 6-phosphate (Alt6P) catalyzed by altrose 6-phosphate isomerase (Alt6PI); and converting the Alt6P produced to altrose catalyzed by altrose 6-phosphate phosphatase (Alt6PP).

In one embodiment, the improved process of the invention is directed to the production of talose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to T6P catalyzed by F6PE; converting the T6P to talose 6-phosphate (Tal6P) catalyzed by talose 6-phosphate isomerase (Tal6PI); and converting the Tal6P to talose catalyzed by talose 6-phosphate phosphatase (Tal6PP).

In one embodiment, the improved process of the invention is directed to the production of sorbose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to T6P catalyzed by F6PE; converting the T6P to sorbose 6-phosphate (S6P) catalyzed by sorbose 6-phosphate epimerase (S6PE); and converting the S6P to sorbose catalyzed by sorbose 6-phosphate phosphatase (S6PP).

In one embodiment, the improved process of the invention is directed to the production of gulose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to T6P catalyzed by F6PE; converting the S6P to gulose 6-phosphate (Gul6P) catalyzed by gulose 6-phosphate isomerase (Gul6PI); and converting the Gul6P to gulose catalyzed by gulose 6-phosphate phosphatase (Gul6PP).

In one embodiment, the improved process of the invention is directed to the production of idose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to T6P catalyzed by F6PE; converting the T6P to sorbose 6-phosphate (S6P) catalyzed by sorbose 6-phosphate epimerase (S6PE); converting the S6P to idose 6-phosphate (I6P) catalyzed by idose 6-phosphate isomerase (I6P1); and converting the I6P to idose catalyzed by idose 6-phosphate phosphatase (I6PP).

In one embodiment, the improved process of the invention is directed to the production of tagatose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to tagatose 6-phosphate (T6P) catalyzed by fructose 6-phosphate epimerase (F6PE); converting the T6P to tagatose catalyzed by tagatose 6-phosphate phosphatase (T6PP).

In one embodiment, the improved process of the invention is directed to the production of psicose. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to fructose 6-phosphate (F6P) catalyzed by phosphoglucoisomerase (PGI); converting the F6P to psicose 6-phosphate (P6P) catalyzed by psicose 6-phosphate epimerase (P6PE); converting the P6P to psicose catalyzed by psicose 6-phosphate phosphatase (P6PP).

In one embodiment, the improved process of the invention is directed to the production of inositol. When starch or a starch derivative is the starting material, the improvement is selected from one or more of the following steps: a) a step of converting G1P to G6P, catalyzed by a PGM having at least 90% sequence identity with any one of SEQ ID NOs: 2-8; b) a step of converting a starch derivative to G1P, catalyzed by an αGP having at least 90% sequence identity with any one of SEQ ID NOs: 10-13; and c) a step of transglycosylating a starch derivative, catalyzed by a 4GT having at least 90% sequence identity with any one of SEQ ID NOs: 15-17. When cellulose or a cellulose derivative is the starting material, the improvement is a step of converting G1P to G6P, catalyzed by a PGM having at least 90% sequence identity with any one of SEQ ID NOs: 2-8. When sucrose is the starting material, the improvement is selected from one or both of the following steps: a) a step of converting G1P to G6P, catalyzed by a PGM having at least 90% sequence identity with any one of SEQ ID NOs: 2-8; and b) a step of converting the sucrose to G1P, catalyzed by a SP having at least 90% sequence identity with any one of SEQ ID NOs: 19-25. Said process further comprises the steps of converting G6P to inositol 3-phosphate (I3P) using inositol phosphate synthase and converting I3P to inositol using inositol monophosphatase. In another embodiment, the improved process of the invention is directed to the production of inositol from sucrose.

FIG. 1 shows an enzymatic pathway for converting sucrose to the G6P intermediate. The improved processes of the invention contain one or more of the following improvements: SP comprises an amino acid sequence having at least 90% sequence identity with any one of SEQ ID NOs: 19-25, and PGM comprises an amino acid sequence having at least 90% sequence identity with any one of SEQ ID NOs: 2-8. In preferred processes of the invention, the SP comprises the amino acid sequence of any one of SEQ ID NOs: 19-25 and the PGM comprises the amino acid sequence of any one of SEQ ID NO: 2-8. In more preferred processes, the SP comprises the amino acid sequence of SEQ ID NO: 21 and the PGM comprises the amino acid sequence of SEQ ID NO: 8.

Figure 2:
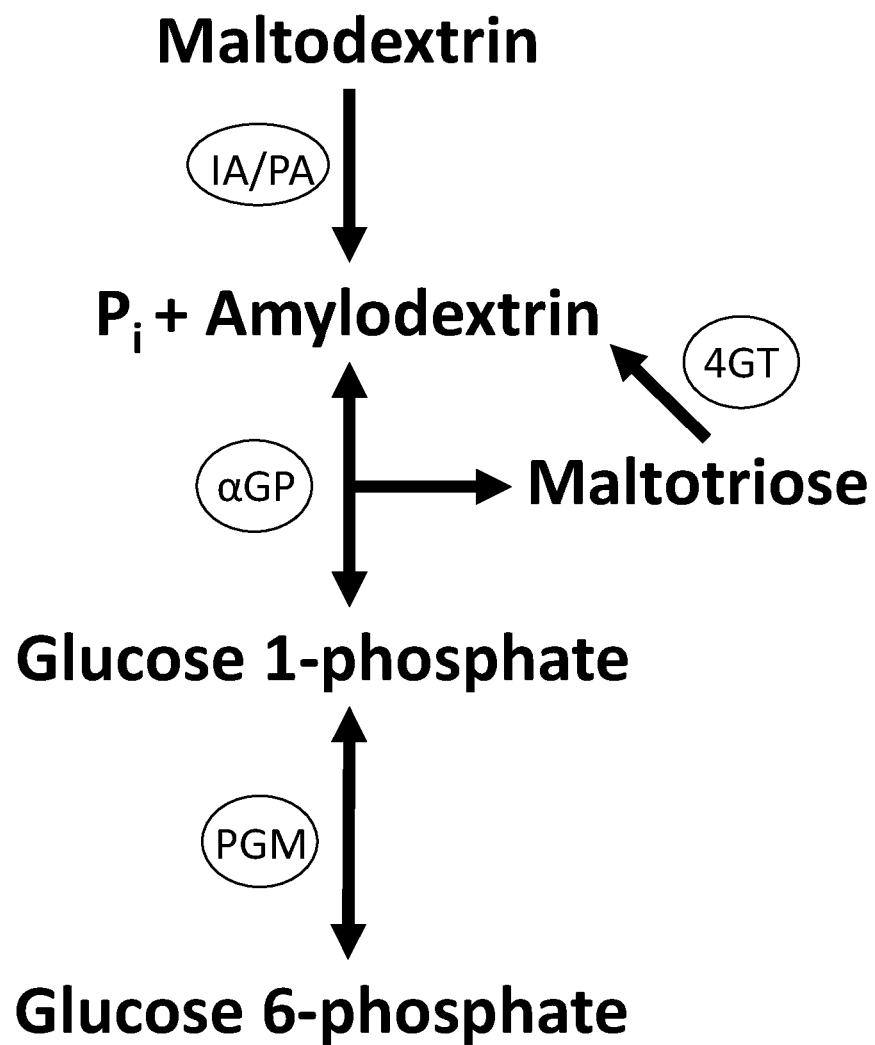
FIG. 2 is a schematic diagram showing an enzymatic pathway converting a starch derivative, maltodextrin, to G6P. The following abbreviations are used: IA, isoamylase; PA, pullulanase; αGP, alpha-glucan phosphorylase or starch phosphorylase; 4GT, 4-glucan transferase; and PGM, phosphoglucomutase. The improved processes of the invention contain one or more of the following improvements: PGM comprises an amino acid sequence having at least 90% sequence identity with any one of SEQ ID NOs: 2-8; αGP comprises an amino acid sequence having at least 90% sequence identity with any one of SEQ ID NOs: 10-13; and 4GT comprises an amino acid sequence having at least 90% sequence identity with any one of SEQ ID NOs: 15-17.

FIG. 2 is a schematic diagram showing an enzymatic pathway converting a starch derivative, maltodextrin, to the G6P intermediate. The following abbreviations are used: IA, isoamylase; PA, pullulanase; αGP, alpha-glucan phosphorylase or starch phosphorylase; 4GT, 4-glucan transferase; and PGM, phosphoglucomutase. The improved processes of the invention contain one or more of the following improvements: PGM comprises an amino acid sequence having at least 90% sequence identity with any one of SEQ ID NOs: 2-8; αGP comprises an amino acid sequence having at least 90% sequence identity with any one of SEQ ID NOs: 10-13; and 4GT comprises an amino acid sequence having at least 90% sequence identity with any one of SEQ ID NOs: 15-17. In preferred processes of the invention, the PGM comprises the amino acid sequence of any one of SEQ ID NOs: 2-8, the αGP comprises an amino acid sequence of any one of SEQ ID NOs: 10-13, and the 4GT comprises an amino acid sequence of any one of SEQ ID NOs: 15-17. In more preferred processes of the invention, the PGM comprises the amino acid sequence of SEQ ID NO: 8, the αGP comprises the amino acid sequence of SEQ ID NO: 11, and the 4GT comprises the amino acid sequence of SEQ ID NO: 17.

Figure 3:
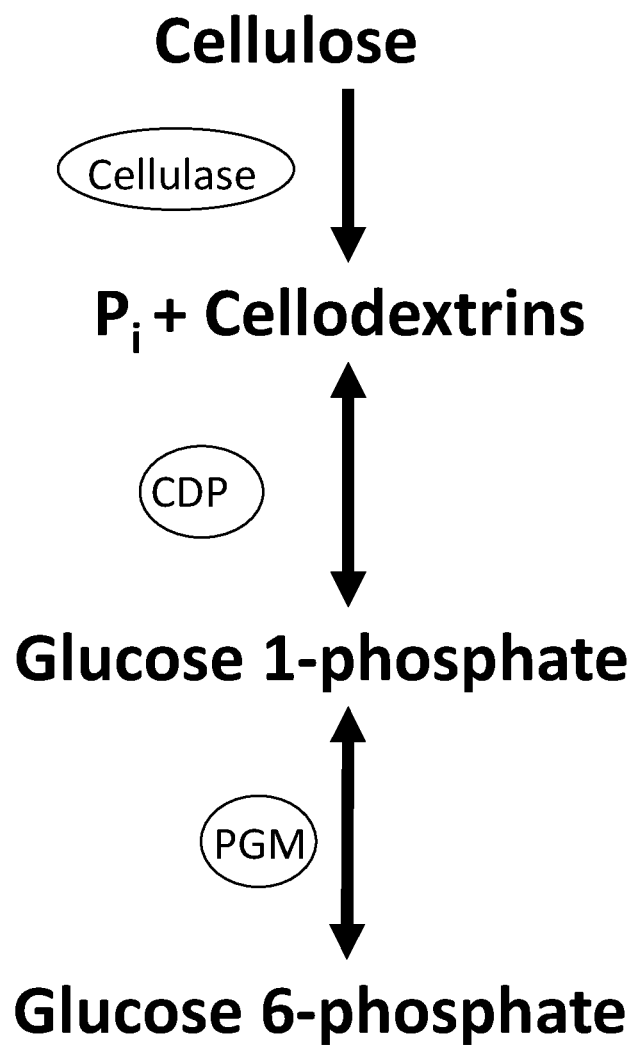
FIG. 3 is a schematic diagram showing an enzymatic pathway converting cellulose to G6P. The following abbreviations are used: CDP, cellodextrin phosphorylase; and PGM, phosphoglucomutase. In improved processes of the invention, PGM comprises an amino acid sequence having at least 90% sequence identity with any one of SEQ ID NOs: 2-8.

FIG. 3 shows an enzymatic pathway for converting cellulose to the G6P intermediate. In improved processes of the invention, PGM comprises an amino acid sequence having at least 90% sequence identity with any one of SEQ ID NOs: 2-8. Preferably, the PGM comprises the amino acid sequence of any one of SEQ ID NO: 2-8. More preferably, the PGM comprises the amino acid sequence of SEQ ID NO: 8. In some improved processes of the invention for the production of a hexose, the one or more of the process steps are conducted in a single reaction vessel. In other improved processes of the invention, the process steps are conducted in more than one reaction vessels. Phosphate ions produced by dephosphorylation of the hexose phosphate can then be recycled in the process step of converting the starch derivative to G1P, particularly when all process steps are conducted in a single bioreactor or reaction vessel. The ability to recycle phosphate allows for non-stoichiometric amounts of phosphate to be used, which keeps reaction phosphate concentrations low. This affects the overall pathway and the overall rate of the processes, but does not limit the activity of the individual enzymes and allows for overall efficiency of the hexose making processes.

In an improved process of the invention for the production of a hexose, the process steps are conducted ATP-free, NAD(P)(H)-free, at a phosphate concentration from about 0.1 mM to about 150 mM, the phosphate is recycled, and/or the step of dephosphorylation of the hexose phosphate involves an energetically favorable chemical reaction. In improved processes of the invention, the process steps are conducted under at least one of the following process conditions: at a temperature ranging from about 37° C. to about 85° C., at a pH ranging from about 5.0 to about 8.0, or for about 0.5 hours to about 48 hours, or as a continuous process.

For example, reaction phosphate concentrations in each of the processes can range from about 0 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration in each of the processes can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM. Low phosphate concentration results in decreased production costs due to low total phosphate and thus lowered cost of phosphate removal. It also prevents inhibition of phosphatases or other enzymes in the process by high concentrations of free phosphate and decreases the potential for phosphate pollution.

Furthermore, each of the processes disclosed herein can be conducted without added ATP as a source of phosphate, i.e., ATP-free. Each of the processes can also be conducted without having to add NAD(P)(H), i.e., NAD(P)(H)-free.

Any suitable biologically compatible buffering agent known in the art can be used in each of the processes of the invention, such as HEPES, PBS, BIS-TRIS, MOPS, DIPSO, Trizma, etc. The reaction buffer for the processes according to the invention can have a pH ranging from 5.0-8.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain divalent metal cations. In some processes, the steps are conducted in the presence of a divalent metal cation selected from the group consisting of $Mg^{2+}$, $Zn^{2+}$, $Ca^{2+}$, $Co^{2+}$, $Mn^{2+}$, and combinations thereof. As known in the art, suitable salts may be used to introduce the desired metal cation.

In each of the processes of the invention the reaction temperature at which the process steps are conducted can range from 37-85° C. More preferably, the steps can be conducted at a temperature ranging from about 40° C. to about 80° C. The temperature can be, for example, about 40° C., about 45° C., about 50° C., about 55° C., about 60° C., about 65° C., about 70° C., about 75° C., about 80° C., or about 85° C. Preferably, the reaction temperature is about 40° C., about 45° C., about 50° C., about 55° C., about 60° C., or about 65° C. More preferably the reaction temperature ranges from about about 50° C. to about 55° C.

For some of the improved processes of the invention, the reaction time can be adjusted as necessary, and can range from about 0.5 hours to about 48 hours. For example, the reaction time can be about 1 hour, about 2 hours, about 4 hours, about 8 hours, about 12 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The process can also be conducted in one or more reactors as a continuous process, with no set time limit. In a continuous process, for example, a solution maltodextrin would be pumped through a bed of immobilized enzyme at such a rate that conversion to tagatose would be complete when the solution leaves one or more columns for downstream processing. For example, 200 g/L of maltodextrin can be pumped through a column packed with immobilized enzymes (maintained at, for example, 50° C.) such that when the maltodextrin leaves the column maximum tagatose yield is achieved. This methodology offers greater volumetric productivity over batch methods. This limits the time the product is in contact with the column and reaction conditions, which decreases chances of product degradation (e.g., potential hydroxymethylfurfural formation). It also increases automation in production and therefore reduces operating expenses.

The enzymes used in the steps of invention may take the form of soluble, immobilized, assembled, entrapped, or aggregated proteins. These enzymes could be adsorbed on insoluble organic or inorganic supports commonly used to improve functionality, as known in the art. These include polymeric supports such as agarose, methacrylate, polystyrene, or dextran, as well as inorganic supports such as glass, metal, or carbon-based materials. These materials are often produced with large surface-to-volume ratios and specialized surfaces that promote attachment and activity of immobilized enzymes. The enzymes might be affixed to these solid supports through covalent, ionic, or hydrophobic interactions. The enzymes could also be affixed through genetically engineered interactions such as covalent fusion to another protein or peptide sequence with affinity to the solid support, most often a polyhistidine sequence. The enzymes might be affixed either directly to the surface or surface coating, or they might be affixed to other proteins already present on the surface or surface coating. The enzymes can be immobilized all on one carrier, on individual carriers, or a combination of the two (e.g., two enzyme per carrier then mix those carriers). These variations can be mixed evenly or in defined layers to optimize turnover in a continuous process. For example, the beginning of the reactor may have a layer of αGP to ensure a high initial G1P increase. Enzymes may be immobilized all on one carrier, on individual carriers, or in groups. These enzymes may be mixed evenly or in defined layers or zones to optimize turnover.

Each of the processes according to the invention can achieve high yields due to the very favorable equilibrium constant for the overall reaction. Theoretically, up to 99% yields can be achieved if the starting material is completely converted to a phosphorylated intermediate.

Processes of the invention use low-cost starting materials and reduce production costs by decreasing costs associated with the feedstock and product separation. Starch and its derivatives are less expensive feedstocks than, for example, lactose. When a hexose is produced from lactose, glucose and other hexose(s) are separated via chromatography, which leads to higher production costs. Also, the step of hexose dephosphorylation by a phosphatase is an irreversible phosphatase reaction, regardless of the feedstock. Therefore, hexose is produced with a very high yield while effectively minimizing the subsequent product separation costs.

Processes according to the invention allow for easy recovery of hexose, and separation costs are minimized. In some preferred processes of the invention, the recovery of the desired hexose is performed without chromatographic separation. Following production of the hexose in a continuous reaction, the product is instead passed through microfiltration, ion exchange (cation then anion, possible mixed bed for polishing), concentration, crystallization, crystal isolation, and drying. Due to high yields of the hexose, the crystallization step is all that is needed to purify the hexose. To further purify the hexose prior to crystallization, one can employ nanofiltration to eliminate the risk of enzyme being present in the crystallization process and to remove any unconverted dextrins that may co-crystallize with the hexose or limit the recyclability of the mother liquor (maltodextrin, maltotetraose, maltotriose, maltose, etc.).

Improved processes of the invention also include the production of G6P from sucrose, starch or a starch derivative, or cellulose or a cellulose derivative. G6P produced from the processes of the invention may be isolated and purified by techniques known in the art, such as for example, chromatography.

EXAMPLES

The following Examples describe the improved processes using enzymes with higher activities.

Materials and Methods

All chemicals, including glucose 1-phosphate, magnesium chloride, maltodextrin DE 4-7, sodium phosphate (mono and dibasic), are reagent grade or higher and purchased from Sigma-Aldrich (St. Louis, MO, USA) or Fisher Scientific (Pittsburgh, PA, USA), unless otherwise noted. Maltotriose was purchased from Carbosynth (Berkshire, United Kingdom). E. coli BL21 (DE3) (Sigma-Aldrich, St. Louis, MO, USA) was used as a host cell for recombinant protein expression. ZYM-5052 media including 50 mg L-1 kanamycin was used for E. coli cell growth and recombinant protein expression.

Production and Purification of Recombinant Enzymes

The E. coli BL21 (DE3) strain harboring a protein expression plasmid (pET28a) was incubated in a 1-L Erlenmeyer flask with 100 mL of ZYM-5052 media containing 50 mg L-1 kanamycin. Cells were grown at 30° C. with rotary shaking at 220 rpm for 16-24 hours. The cells were harvested by centrifugation at 12° C. and washed once with either 20 mM HEPES (pH 7.5) containing 20 mM HEPES (pH 7.5) containing 300 mM NaCl and 5 mM imidazole (Ni purification). The cell pellets were re-suspended in the same buffer and lysed by sonication. After centrifugation, the target proteins in the supernatants were purified via standard methods. His-tagged proteins were purified by the Profinity IMAC Ni-Charged Resin (Bio-Rad, Hercules, CA, USA) using a gradient of increasing imadazole in the previously described buffer. The purity of the recombinant proteins was examined by sodium dodecyl sulfate polyacrylamide gel electrophoresis (SDS-PAGE).

Example 1. Improved Processes with Higher Activity PGMs

Various phosphoglucomutases (PGMs) were isolated and assayed for converting G1P to G6P in a multi-step enzymatic reaction. The relative activity of each PGM was measured in the following manner. A reaction of 50 mM HEPES pH 7.2, 5 mM $MgCl_2$, 50 mM glucose 1-phosphate, 0.02 g/L PGM, 0.1 g/L PGI, and 0.1 g/L F6PP was prepared and incubated at 50° C. for 30 minutes. The reactions were stopped via filtration of enzyme with a Vivaspin 2 concentrator (10,000 MWCO). The product, fructose, was evaluated using a Hi-Plex H+ column and refractive index detector. The sample was run in 5 mM $H_2SO_4$ at 0.6 mL/min for 15.5 min at 65° C. The amount of fructose made in 30 minutes was used to determine the relative efficiencies of each PGM in the enzymatic process. The increase in activity was determined using an average of the increase in fructose peak area and peak height.

Figure 19:
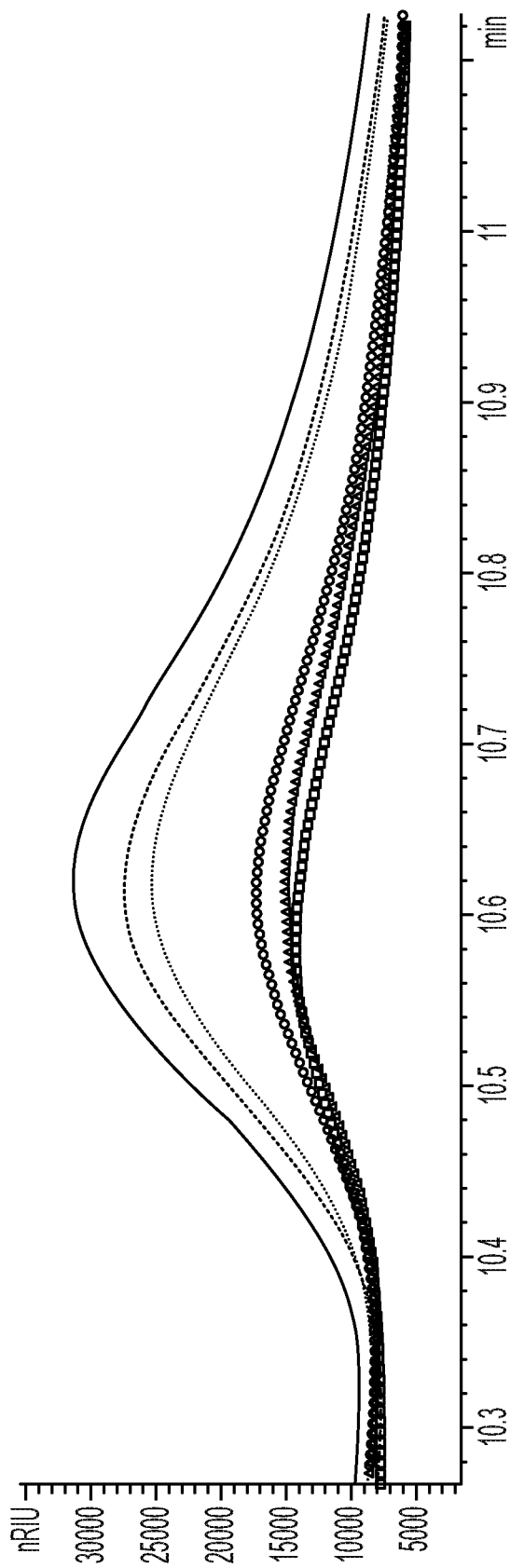
FIG. 19 is a chromatogram of reactions with Uniprot ID A0A150LLZ1 compared to even higher activity PGMs. The chromatogram shows the level of fructose made from glucose 1-phosphate after incubation with limiting PGM, excess phosphoglucoisomerase, and excess fructose 6-phosphate phosphatase. It is clearly seen that the use of all other PGMs, in equal amounts, results in improved fructose production and therefore enhanced PGM activity since it is the limiting enzyme of the enzymatic process. In the figure, Uniprot ID A0A0P6YKY9=solid line; Uniprot ID E8N4Y6=dashed line; Uniprot ID R7RR04=dotted line; Uniprot ID A0A023D195=line of circles; UniParc ID UPI0001D17AE3=line of triangles; and Uniprot ID A0A150LLZ1=line of squares. The activity of the reference PGM Uniprot ID Q68BJ6, which was much lower (see Table 1), is not shown.

FIG. 19 is a chromatogram showing activity of various PGMs. The chromatogram shows the level of fructose made from glucose 1-phosphate after incubation with various PGMs, excess phosphoglucoisomerase, and excess fructose 6-phosphate phosphatase. PGM is the limiting enzyme of the cascade. Table 1 shows that PGMs for use in the improved processes of the invention have improved activity relative to the previously disclosed PGM from *Thermococcus kodakaraensis* (Uniprot ID Q68BJ6). See International Patent Application Publication WO2017/059278.

TABLE 1

Relative activities of PGMs

| PGM Uniprot ID SEQ ID NO | % Activity Relative to Reference PGM |
|---|---|
| (Reference) Q68BJ6 SEQ ID NO: 1 | 100 |
| A0A023CRS6 SEQ ID NO: 2 | 800 |
| A0A150LLZ1 SEQ ID NO: 3 | 2000 |
| UPI0001D17AE3 (UniParc ID) SEQ ID NO: 4 | 2200 |
| A0A023DI95 SEQ ID NO: 5 | 2080 |
| R7RR04 SEQ ID NO: 6 | 5200 |
| E8N4Y6 SEQ ID NO: 7 | 5900 |
| A0A0P6YKY9 SEQ ID NO: 8 | 6600 |

Example 2. Improved Processes with Higher Activity αGPs

The relative activity of each αGP was measured in the following manner. A 200 μL reaction of 25 mM sodium phosphate pH 7.2, 5 mM $MgCl_2$, 20 g/L maltodextrin DE 4-7, 9 μg of αGP, and 0.1 g/L PGM was prepared and incubated at 50° C. Samples were mixed with 1.5 mM NAD+ and 3 U/mL glucose 6-phosphate dehydrogenase at various time points. The absorbance at 340 nm at each time point was used to get the rate of reaction. This rate was used to ascertain the specific activity of each αGP, which was used for relative activity comparisons.

Table 2 shows that αGPs for use in the improved processes of the invention have improved activity relative to the previously disclosed αGP from *Thermotoga maritima* (Uniprot ID G4FEH8). See International Patent Application Publication WO2017/059278.

TABLE 2

Relative activities of αGPs

| αGP Uniprot ID SEQ ID NO | % Activity relative to Reference αGP |
|---|---|
| (Reference) G4FEH8 SEQ ID NO: 9 | 100 |
| Q5SJ42 SEQ ID NO 10 | 171 |
| G8NCC0 SEQ ID NO: 11 | 286 |
| B0K7V8 SEQ ID NO 12 | 228 |
| D1B926 SEQ ID NO 13 | 211 |

Example 3. Improved Processes with Higher Activity 4GTs

The relative activity of each 4GT was measured in the following manner. A 200 μL reaction of 50 mM sodium phosphate pH 7.2, 5 mM MgCl2, 20 g/L maltotriose, and 9 µg of 4GT was prepared and incubated at 50° C. Samples were mixed with 1.5 mM NAD+, 1 mM ATP, 1 U/mL hexokinase, and 1 U/mL glucose 6-phosphate dehydrogenase at various time points. The absorbance at 340 nm at each time point was used to get the rate of reaction. This rate was used to a certain the specific activity of each 4GT, which was used for relative activity comparisons.

Table 3 shows that 4GTs for use in the improved processes of the invention have improved activity relative to the previously disclosed 4GT from *Thermococcus litoralis* (Uniprot ID O32462). See International Patent Application Publication WO2018/169957.

TABLE 3

Relative activities of 4GTs

| 4GT Uniprot ID SEQ ID NO | % Activity relative to Reference 4GT |
|---|---|
| (Reference) O32462 | 100 |
| SEQ ID NO: 14 E4U8S9 | 228 |
| SEQ ID NO: 15 D7BF07 | 312 |
| SEQ ID NO: 16 E8MXP8 | 284 |
| SEQ ID NO: 17 | |

Example 4. Improved Processes with Higher Activity SPs

Various sucrose phosphorylases, assumed by homology to Uniprot ID D9TT09 (Verhaeghe et al. The quest for a thermostable sucrose phosphorylase reveals sucrose 6'-phosphate phosphorylase as a novel specificity. Appl Microbiol Biotechnol. 2014 August; 98(16):7027-37), were isolated and assayed for converting sucrose to glucose 6-phosphate.

The relative efficiency of each SP was measured in the following manner. A reaction of 25 mM sodium phosphate pH 7.2, 5 mM MgCl$_2$, 200 g/L sucrose, 0.15 g/L SP, 0.1 g/L PGM, 0.1 g/L PGI, and 0.3 g/L F6PP was prepared and incubated at 50° C. Samples were taken at 0 hrs 2 hrs, 6 hrs, and 8 hrs. The reactions were stopped via filtration of enzyme with a Vivaspin 2 concentrator (10,000 MWCO). The product, fructose, was evaluated using a Supel Cogel Pb column and refractive index detector. The sample was run in ultrapure water at 0.6 mL/min for 25 min at 80° C. The amount of fructose made at 2 hours is used to determine the relative activities of each SP. The amount of fructose made at 6 hrs (completion verified at 8 hrs) shows the differences in maximum achievable yield for each SP.

Figure 18:
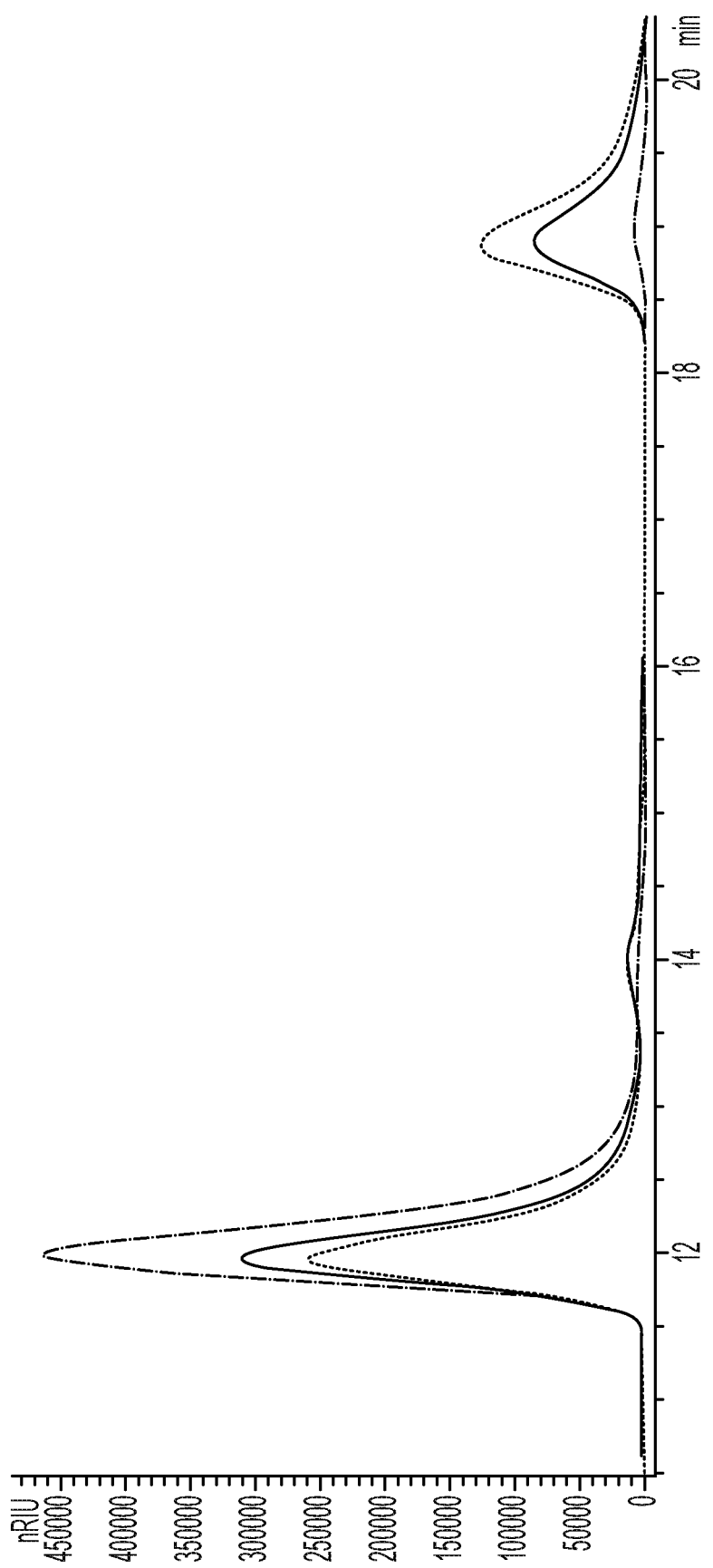
FIG. 18 shows chromatograms of sucrose phosphorylase activities. The top chromatogram shows reactions with Uniprot ID D9TT09 (reference SP) compared to the higher activity SP, Uniprot ID F6BJS0. The 0 hour reaction (sucrose to fructose) is in shown as the dashed line and 2 hour reactions using identical amounts of SP and other enzymes are shown for both reference (solid line) and higher activity SP (dotted line). At 2 hours, the higher activity SP creates approximately 150% the amount of fructose as the reference SP. The bottom chromatogram compares Uniprot ID D9TT09 (reference SP) to the higher activity Uniprot ID F6BJS0. The 0 hour reaction (sucrose to fructose) is in is shown as a dashed line and 6 hour reactions using identical amounts of SP and other enzymes are shown for both reference SP (solid line) and higher activity SP (dotted line). At 6 hours (maximum yield for both reactions), the higher activity SP creates approximately 130% the amount of fructose as the reference SP.
Figure 18:
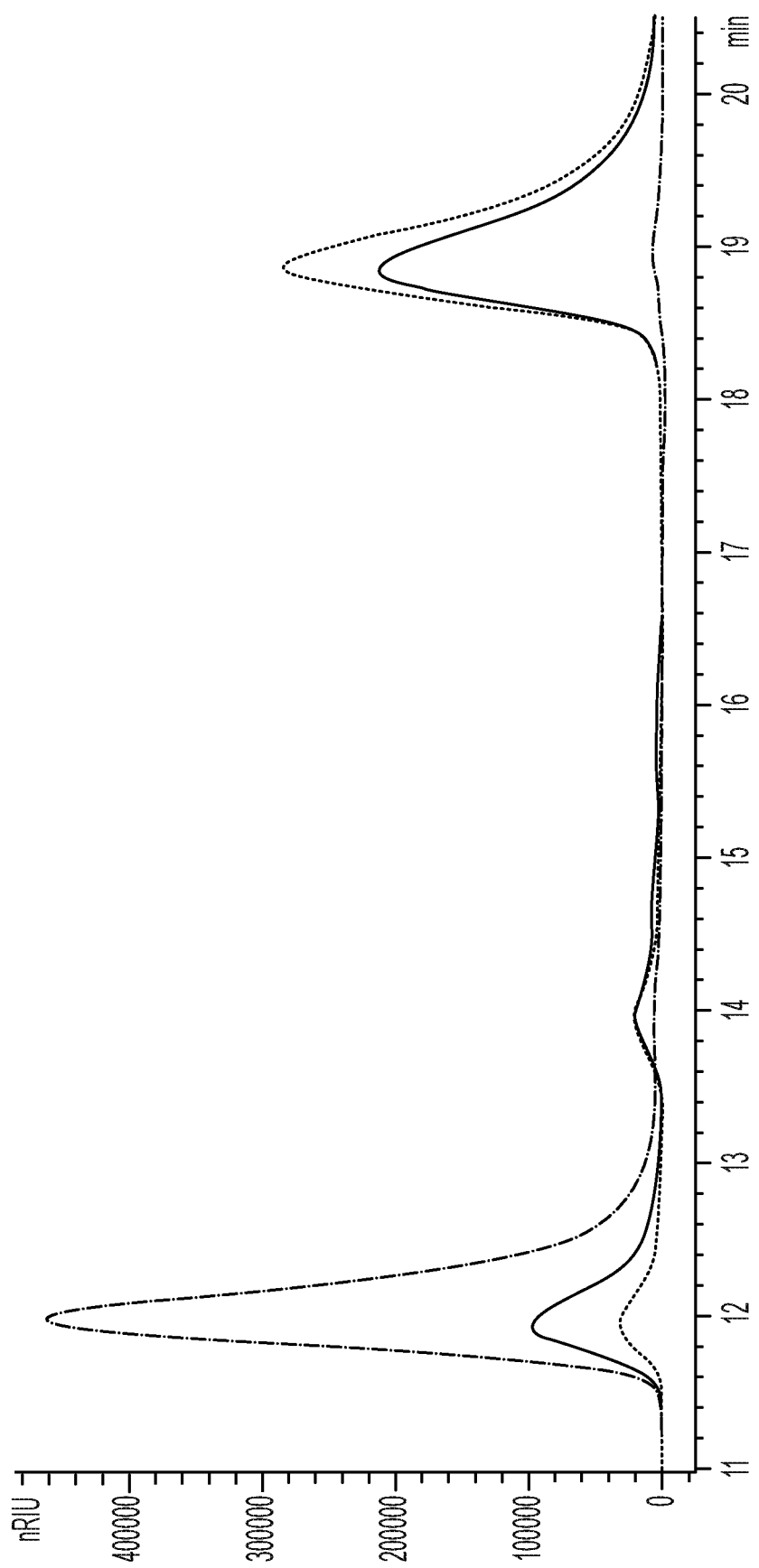

The effects on full conversion of sucrose to fructose were also investigated. Of the eight enzymes tested relative to the reference (below table), seven show improved activity over Uniprot ID D9TT09 and one shows unexpected advantages when making fructose from sucrose. FIG. 18 shows chromatograms of sucrose phosphorylase activities, comparing Uniprot ID D9TT09 (reference SP) to Uniprot ID F6BJS0. At 2 hours, the higher activity SP creates approximately 150% the amount of fructose as the reference SP. The bottom chromatogram compares Uniprot ID D9TT09 (reference SP) to Uniprot ID F6BJS0 in terms of maximum yield. At 6 hours (maximum yield for both reactions), the higher activity SP creates approximately 130% the amount of fructose as the reference SP. Interestingly, the relative yields do not directly correlate with relative activities. Presumably, contributing factors include product inhibition of sucrose phosphorylase by fructose, the rate of the reverse reaction (G1P+fructose⇔sucrose+P$_i$), and more broadly the equilibrium between the formation of fructose and the degradation of fructose at late stages of the reaction. The comparative SP from *Thermanaerothrix daxensis* (Uniprot ID A0A0N8GPZ6), with amino acid sequence as indicated in SEQ ID NO: 26, showed lower relative activity and lower maximal yield of fructose compared to the previously disclosed SP.

TABLE 4

Relative activities and acheivable yields of SPs

| SP Uniprot ID SEQ ID NO | % Activity relative to Reference SP | % Maximum Yield of Fructose relative to Reference SP |
|---|---|---|
| (Reference) D9TT09 SEQ ID NO: 18 | 100 | 100 |
| A0A1X2FWC2 SEQ ID NO: 19 | 111 | 109 |
| L0IL15 SEQ ID NO: 20 | 150 | 101 |
| F6BJS0 SEQ ID NO: 21 | 149 | 132 |
| A0A1Y3Q6Q6 SEQ ID NO: 22 | 150 | 103 |
| Q84HQ2 SEQ ID NO: 23 | 131 | 137 |
| A0A388NK91 SEQ ID NO: 24 | 122 | 119 |
| A0A135L6L9 SEQ ID NO: 25 | 144 | 116 |
| (Comparative) A0A0N8GPZ6 SEQ ID NO: 26 | 92 | 71 |

Example 5. Improved Enzymatic Production of G6P

Figure 17:
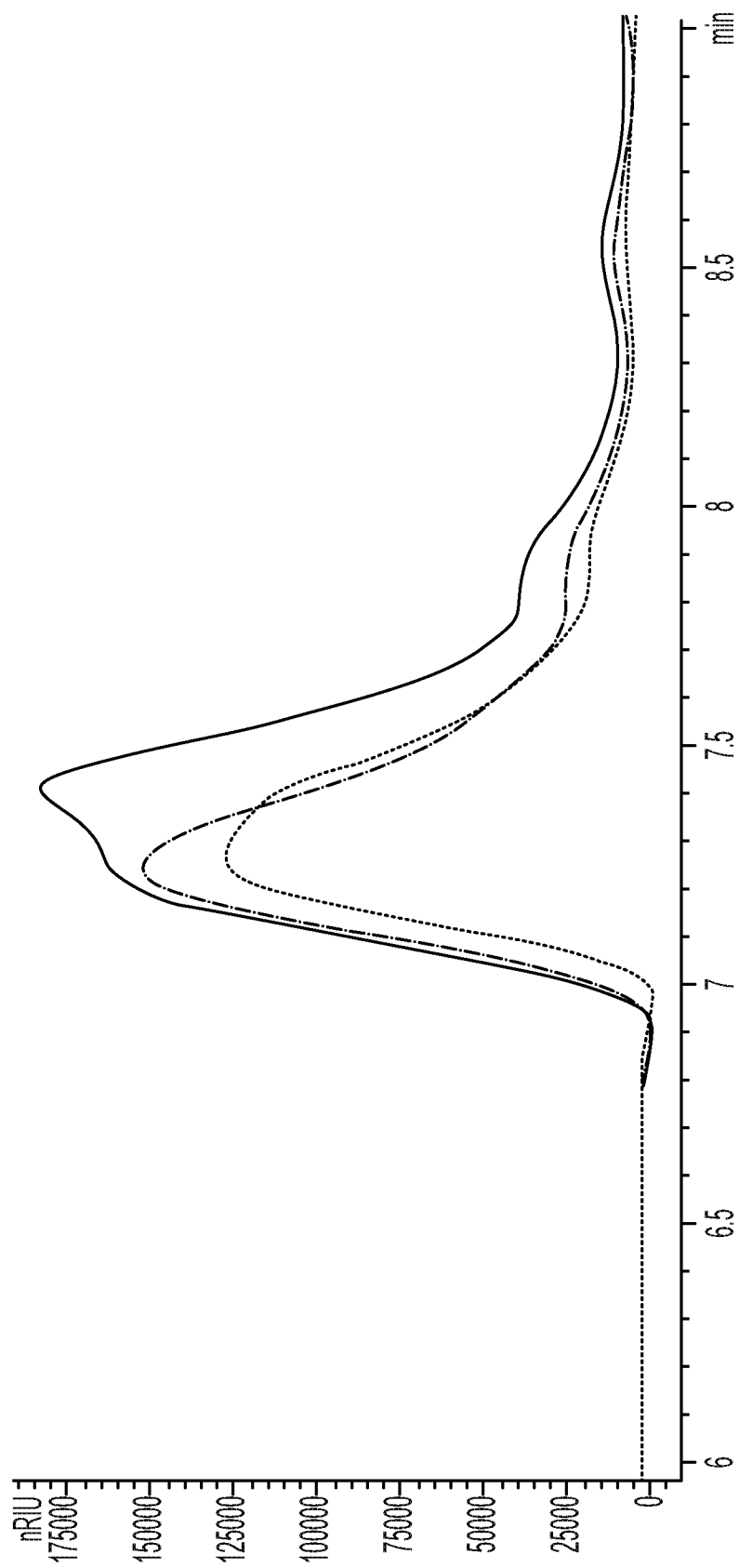
FIG. 17 shows the conversion of maltodextrin to G6P via HPLC chromatogram. (Dashed line) 0 hour chromatogram; (dotted line) 30 min process with previously disclosed αGP (Uniprot ID G4FEH8) and PGM (Uniprot ID Q68BJ6); and (solid line) 30 min "improved" process with higher activity αGP (Uniprot ID D1B926) and higher activity PGM (Uniprot ID A0A150LLZ1). (1) Void and maltodextrins, (2) G1P and G6P, (3) maltotriose, and (4) maltose.

To visualize improvements in enzymatic activity, the conversion of maltodextrin to G6P was carried out using previously disclosed αGP (Uniprot ID G4FEH8) and PGM (Uniprot ID Q68BJ6), and comparing that process a process using αGP (Uniprot ID D1B926) and PGM (Uniprot ID A0A150LLZ1), which have higher activities. A 200 µL reaction mixture containing 20 g/L maltodextrin DE 5, 50 mM phosphate buffer pH 7.2, 5 mM MgCl$_2$, 0.05 g/L αGP, and 0.005 g/L PGM was incubated at 50° C. for 30 minutes. The reaction was stopped via filtration of enzyme with a Vivaspin 2 concentrator (30,000 MWCO) and analyzed via HPLC (Agilent 1100 series) using an Agilent Hi-Plex H-column and refractive index detector. The sample was run in 5 mM H$_2$SO$_4$ at 0.6 mL/min for 15.5 minutes at 65° C. Results were not quantified as the peaks for the void, maltodextrin, and G6P are too close to quantify any individual component reliably (FIG. 17), but clearly much more G6P is created with the enzymes αGP (Uniprot ID D1B926) and PGM (Uniprot ID A0A150LLZ1).

The claimed invention is:

1. An improved process for the enzymatic production of a hexose, wherein the improved process comprises:
   a) converting glucose 1-phosphate (G1P) to glucose 6-phosphate (G6P), catalyzed by a higher activity phosphoglucomutase (PGM), wherein the higher activity PGM results in an improved process that, when the hexose is fructose, produces at least 800% more fructose relative to a process to produce fructose under equivalent process conditions in which the conversion of G1P to G6P is catalyzed by a PGM corresponding to Uniprot ID Q68BJ6 from *Thermococcus kodakaraensis*;
   b) converting the G6P to fructose 6-phosphate (F6P), catalyzed by a phosphoglucoisomerase (PGI); and
   c) enzymatically converting the F6P to the hexose, catalyzed by an epimerase, an isomerase, a phosphatase, or a combination thereof.

2. The improved process of claim 1, further comprising: one or more steps for converting a cellulose or a cellulose derivative to G1P catalyzed by a cellulase, a cellodextrin phosphorylase, or both.

3. The improved process of claim 1, further comprising: converting sucrose to G1P catalyzed by a sucrose phosphorylase (SP).

4. The improved process of claim 3, wherein the SP comprises an amino acid sequence having at least 90% sequence identity with any one of SEQ ID NOs: 19-25.

5. The improved process of claim 1, wherein the hexose is selected from the group consisting of allose, mannose, galactose, fructose, altrose, talose, sorbose, gulose idose, allulose, inositol, and tagatose.

6. The improved process of claim 5, further comprising a step of reduction of the hexose to its sugar alcohol.

7. The improved process of claim 1, further comprising:
   converting a starch derivative to G1P, catalyzed by an alpha-glucan phosphorylase (αGP); and
   transglycosylating a starch derivative, catalyzed by a 4-alpha-glucan transferase (4GT), wherein the starch derivative is selected from the group consisting of amylose, amylopectin, soluble starch, amylodextrin, maltotriose, maltose, and maltodextrin.

8. The improved process of claim 7, wherein the αGP comprises an amino acid sequence having at least 90% sequence identity with any one of SEQ ID NOs: 10-13.

9. The improved process of claim 7, wherein the 4GT comprises an amino acid sequence having at least 90% sequence identity with any one of SEQ ID NOs: 15-17.

10. The improved process of claim 1, further comprising a step of dephosphorylating a hexose-phosphate using a hexose phosphate phosphatase.

11. The improved process of claim 10, wherein the process steps are conducted in a single reaction vessel.

12. The improved process of claim 11, wherein the process steps are conducted ATP-free, NAD (P) (H)-free, at a phosphate concentration from about 0.1 mM to about 150 mM, the phosphate is recycled, and/or the step of dephosphorylation of the hexose phosphate involves an energetically favorable chemical reaction.

13. The improved process of claim 1, wherein the process steps are conducted under at least one of the following process conditions:
   at a temperature ranging from about 37° C. to about 85° C., at a pH ranging from about 5.0 to about 8.0, or
for about 0.5 hours to about 48 hours, or as a continuous reaction.

14. The improved process of claim 1, wherein the higher activity PGM comprises an amino acid sequence having at least 90% sequence identity with any one of SEQ ID NOS: 2-8.

15. An improved process for the enzymatic production of a hexose, wherein the improved process comprises:
  a) converting a starch derivative to glucose 1-phosphate (G1P), catalyzed by a higher activity alpha-glucan phosphorylase (αGP), wherein the higher activity αGP comprises an amino acid sequence having at least 90% sequence identity with any one of SEQ ID NOs: 10-13;
  b) converting the G1P to glucose 6-phosphate (G6P), catalyzed by a phosphoglucomutase (PGM);
  c) converting the G6P to fructose 6-phosphate (F6P), catalyzed by a phosphoglucoisomerase (PGI); and
  d) enzymatically converting the F6P to the hexose, catalyzed by an epimerase, an isomerase, a phosphatase, or a combination thereof,
wherein the improved process produces at least 170% more G6P relative to a process to produce G6P under equivalent process conditions in which the conversion of a starch derivative to G1P is catalyzed by an αGP corresponding to Uniprot ID G4FEH8 from *Thermotoga maritima*.

16. An improved process for the enzymatic production of a hexose, wherein the improved process comprises:
  a) converting a starch derivative to glucose 1-phosphate (G1P), catalyzed by an alpha-glucan phosphorylase (aGP);
  b) transglycosylating a starch derivative, catalyzed by a higher activity 4-alpha-glucan transferase (4GT), wherein the higher activity 4GT results in an improved process that, when the starch derivative is amylodextrin, produces at least 220% more glucose 6-phosphate (G6P) relative to a process to produce G6P under equivalent process conditions in which the transglycosylation of amylodextrin is catalyzed by an 4GT corresponding to Uniprot ID O32462 from *Thermococcus litoralis*;
  c) converting the G1P to G6P, catalyzed by a phosphoglucomutase (PGM);
  d) converting the G6P to fructose 6-phosphate (F6P), catalyzed by a phosphoglucoisomerase (PGI); and
  e) enzymatically converting the F6P to the hexose, catalyzed by an epimerase, an isomerase, a phosphatase, or a combination thereof.

17. The improved process of claim 16, wherein the higher activity 4GT comprises an amino acid sequence having at least 90% sequence identity with any one of SEQ ID NOs: 15-17.

18. An improved process for the enzymatic production of a hexose, wherein the improved process comprises:
  a) a step of converting sucrose to glucose 1-phosphate (G1P), catalyzed by a higher activity sucrose phosphorylase (SP), wherein the higher activity SP results in an improved process that, when the hexose is fructose, produces at least 110% more fructose relative to a process to produce fructose under equivalent process conditions in which the conversion of sucrose to G1P is catalyzed by a SP corresponding to Uniprot ID D9TT09 from *Thermoanaerobacterium thermosaccharolyticum*;
  b) converting the G1P to glucose 6-phosphate (G6P), catalyzed by a phosphoglucomutase (PGM);
  c) converting the G6P to fructose 6-phosphate (F6P), catalyzed by a phosphoglucoisomerase (PGI); and
  d) enzymatically converting the F6P to the hexose, catalyzed by an epimerase, an isomerase, a phosphatase, or a combination thereof.

19. The improved process of claim 18, wherein the higher activity SP comprises an amino acid sequence having at least 90% sequence identity with any one of SEQ ID NOs: 19-25.

* * * * *